US008556882B2

(12) United States Patent  (10) Patent No.: US 8,556,882 B2
Morgan et al.  (45) Date of Patent: Oct. 15, 2013

(54) INDUCIBLE INTERLEUKIN-12

(75) Inventors: Richard A. Morgan, Columbia, MD (US); Steven A. Rosenberg, Potomac, MD (US); Ling Zhang, Rockville, MD (US); Nicholas P. Restifo, Chevy Chase, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/266,280

(22) PCT Filed: Apr. 22, 2010

(86) PCT No.: PCT/US2010/031988
§ 371 (c)(1),
(2), (4) Date: Nov. 30, 2011

(87) PCT Pub. No.: WO2010/126766
PCT Pub. Date: Nov. 4, 2010

(65) Prior Publication Data
US 2012/0071859 A1  Mar. 22, 2012

Related U.S. Application Data

(60) Provisional application No. 61/174,046, filed on Apr. 30, 2009.

(51) Int. Cl.
*C12N 1/15* (2006.01)
*C12N 1/13* (2006.01)
*C12N 1/21* (2006.01)

(52) U.S. Cl.
USPC .................. 604/522; 536/23.5; 514/44 R

(58) Field of Classification Search
USPC .................. 604/522; 536/23.5; 514/44 R
See application file for complete search history.

(56) References Cited

U.S. PATENT DOCUMENTS

| 5,830,755 A | 11/1998 | Nishimura et al. |
| 2006/0160147 A1 | 7/2006 | Vandenbroeck et al. |
| 2009/0042798 A1 | 2/2009 | Wang et al. |
| 2009/0053184 A1 | 2/2009 | Morgan et al. |

FOREIGN PATENT DOCUMENTS

| WO | WO 97/46263 A1 | 12/1997 |
| WO | WO 98/17799 A1 | 4/1998 |
| WO | WO 2007/131092 A2 | 11/2007 |
| WO | WO 2008/039818 A2 | 4/2008 |
| WO | WO 2009/008912 A2 | 1/2009 |

OTHER PUBLICATIONS

Akiyama, Y., *Retroviral-Mediated IL-12 Gene Transduction into Human CD34+ Cell-Derived Dendritic Cells*, International Journal of Oncology, Demetrios A. Spandidos Ed. & Pub., GR, vol. 21, No. 3, pp. 509-514, Sep. 1, 2002.
Brunda, *Role of IL12 as an anti-tumor agent: current status and future directions*, Research in Immunology, Editions Scientifiques et Medicales Elsevier, FR LNKD-DOI:10.1016/0923-2494 (96)83040-9, vol. 146, No. 7-8, Sep. 1, 1995.
Cohen, J., *Science*, 270:(5238)908 (1995).
Del Vecchio, *Clinical Cancer Research*, 13(16):4677-85 (2007).
Goodridge, H., *J. Immunol.*, 178: 3107-15 (2007).
Lizee et al., *Human Gene Therapy*, 14:497-507 (2003).
Hooijberg, E., *NFAT-controlled expression of GFP permits visualization and isolation of antigen-stimulated primary human T cells*, Blood, vol. 96, No. 2, pp. 459-466, Jul. 15, 2000.
Hughes, *Human Gene Therapy*, 16:457-472 (2005).
Li, *Administration Route- and Immune Cell Activation-Dependent Tumor Eradication by IL12 electrotransfer*, Molecular Therapy, Academic Press, San Diego, CA, US LNKD-DOI:10-1016/J.Ymthe, vol. 12, No. 5, pp. 942-949, Nov. 1, 2005.
Neller, *Seminars in Immunol.*, 20: 286-295 (2008).
Parmiani, *J. Immunol.*, 178: 1975-79 (2007).
Rao, A., *Transcription factors of the NFAT family: regulation and function*, Annual Review of Immunology 1997 LNKD-PUBMED:9143705, vol. 15, pp. 707-747 (1997).
Schambach, *Molecular Therapy*, 13:391-400 (2006).
Schambach, *Molecular Therapy*, 15:1167-1173 (2007).
Shin, E. J., *Interleukin-12 expression enhances vesicular stomatitis virus oncolytic therapy in murine squamous cell carcinoma*, The Laryngoscope, Feb. 2007 LNKD-PUBMED:17204993, vol. 117, No. 2, pp. 210-214 Feb. 2007.
Tripathi, P., *An adenoviral vector for probing promoter activity in primary immune cells*, Journal of Immunological Methods, Elsevier Science Publishers B.V., Amsterdam, NL LNKD-DOI:10.1016/J.JIM.2006.01.009, vol. 311, No. 1-2, pp. 19-30, Apr. 20, 2006.
Zhang, L., *Improving Adoptive T Cell Therapy by Targeting and Controlling IL-12 Expression to the Tumor Environment*, Molecular Therapy, American Society of Gene & Cell Therapy, 19: 751-759 Apr. 2011.
Zhang, L., *Improving Adoptive T Cell Therapy Using NFAT Driven Human Single Chain IL-12 Expression Vector*, American Society of Gene Therapy 12th Annual Meeting May 1, 2009, Abstract.
Zhang, L., *Improving Adoptive T Cell Therapy Using an NFAT Driven Human Single Chain IL-12 Expression Vector*, Molecular Therapy, vol. 17, No. 228, Supplement 1, The American Society of Gene Therapy, May 1, 2009.
Zhu, C., *J. Biol. Chem.*, 278(41): 39372-82 (2003).
PCT/US2010/031988 International Search Report.

*Primary Examiner* — Marcia S Noble
(74) *Attorney, Agent, or Firm* — Leydig, Voit & Mayer

(57) ABSTRACT

The invention provides an isolated or purified nucleic acid comprising a nucleotide sequence encoding a nuclear factor of activated T-cells (NFAT) promoter operatively associated with a nucleotide sequence encoding IL-12. The invention also provides a nucleic acid comprising a nucleotide sequence encoding a nuclear factor of activated T-cells (NFAT) promoter operatively associated with a nucleotide sequence encoding IL-12, wherein the NFAT promoter is located 3' of the nucleotide sequence encoding IL-12. Also provided are related recombinant expression vectors, host cells, populations of cells, and pharmaceutical compositions. The invention further provides the use of the inventive nucleic acids or related materials in the treatment or prevention of cancer or an infectious disease in a mammal and in the induction of IL-12 expression in a mammal.

26 Claims, 3 Drawing Sheets

SEQUENCE LISTING

<160> NUMBER OF SEQ ID NOS: 21

<210> SEQ ID NO 1
<211> LENGTH: 1611
<212> TYPE: DNA
<213> ORGANISM: Artificial Sequence
<220> FEATURE:
<223> OTHER INFORMATION: Synthetic

<400> SEQUENCE: 1

```
catggccatg tgtcatcagc agctggtcat cagctggttc agcctggtgt tcctggccag      60
ccccctggtg gccatctggg agctgaagaa agacgtgtac gtggtggagc tggactggta     120
tcccgacgcc cctggcgaga tggtggtgct gacctgcgac accccgaag aggacggcat     180
cacctggacc ctggaccaga gcagcgaggt gctgggcagc ggcaagaccc tgaccatcca     240
ggtcaaagag ttcggcgacg ccggccagta cacctgccac aagggcggcg aagtgctgtc     300
ccacagcctg ctgctgctgc acaagaaaga ggatggcatc tggtccaccg acatcctgaa     360
ggaccagaaa gagcccaaga caagaccctt cctgcggtgc gaggccaaga actacagcgg     420
ccggttcacc tgttggtggc tgaccaccat cagcaccgac ctgaccttca gcgtgaagag     480
cagccggggc agcagcgacc ctcagggcgt gacctgcgga gccgccaccc tgagcgccga     540
gagagtgcgg ggcgacaaca agagtacga gtacagcgtc gagtgccagg aagatagcgc     600
ctgccctgcc gccgaggaaa gcctgcccat cgaggtgatg gtggacgccg tgcacaagct     660
gaagtacgag aactacacct ccagcttttt catccggac atcatcaagc ccgacccccc     720
caagaacctg cagctgaagc ccctgaagaa cagccggcag gtggaggtgt cctgggagta     780
ccctgacacc tggtccaccc ccacagcta cttcagcctg accttctgtg tgcaggtgca     840
gggcaagagc aagcgggaga gaaagaccg ggtgttcacc gacaagacca cgccaccgt     900
gatctgccgg aagaacgcca gcatcagcgt gcgggcccag gaccggtact acagcagctc     960
ctggtccgag tgggccagcg tgccctgcag cggcggaggg ggcggaggaa gccggaacct    1020
gcccgtggct accccgacc ccggcatgtt ccctgcctg caccacagcc agaacctgct    1080
gcgggccgtg agcaacatgc tgcagaaggc ccggcagacc ctggaattct accctgcac    1140
cagcgaggaa atcgaccacg aggacatcac caaggataag accagcaccg tggaggcctg    1200
cctgcccctg gaactgacca gaacgagag ctgtctgaac tctcgggaga caagcttcat    1260
caccaacggc tcttgcctgg ccagcagaaa gaccagcttc atgatggccc tgtgcctgag    1320
cagcatctac gaggacctga agatgtacca ggtggagttc aagaccatga acgccaagct    1380
gctgatggac cccaagcggc agatcttcct ggatcagaac atgctggccg tgatcgacga    1440
gctgatgcag gccctgaact tcaacagcga gacagtgccc cagaagtcca gcctggaaga    1500
gcccgacttc tacaagacca agatcaagct gtgcatcctc ctgcatgcct tccggatccg    1560
ggccgtgacc atcgaccggg tgatgagcta cctgaacgcc agctgatgag c             1611
```

<210> SEQ ID NO 2
<211> LENGTH: 1608
<212> TYPE: DNA
<213> ORGANISM: Homo sapiens

<400> SEQUENCE: 2

```
catggccatg tgtcaccagc agttggtcat ctcttggttt tccctggttt ttctggcatc      60
tccccctcgtg gccatatggg aactgaagaa agatgtttat gtcgtagaat tggattggta    120
tccggatgcc cctggagaaa tggtggtcct cacctgtgac acccctgaag aagatggtat    180
cacctggacc ttggaccaga gcagtgaggt cttaggctct ggcaaaaccc tgaccatcca    240
agtcaaagag tttggagatg ctggccagta cacctgtcac aaaggaggcg aggttctaag    300
ccattcgctc ctgctgcttc acaaaaagga agatggaatt tggtccactg atattttaaa    360
ggaccagaaa gaacccaaaa ataagacctt tctaagatgc gaggccaaga attattctgg    420
acgtttcacc tgctggtggc tgacgacaat cagtactgat ttgacattca gtgtcaaaag    480
cagcagaggc tcttctgacc cccaaggggt gacgtgcgga gctgctacac tctctgcaga    540
gagagtcaga ggggacaaca aggagtatga gtactcagtg gagtgccagg aggacagtgc    600
ctgcccagct gctgaggaga gtctgcccat tgaggtcatg gtggatgccg ttcacaagct    660
caagtatgaa aactacacca gcagcttctt catcagggac atcatcaaac ctgacccacc    720
caagaacttg cagctgaagc cattaaagaa ttctcggcag gtggaggtca gctgggagta    780
ccctgacacc tggagtactc cacattccta cttctccctg acattctgcg ttcaggtcca    840
gggcaagagc aagagagaaa agaaagatag agtcttcacg acaagacct cagccacggt    900
catctgccgc aaaaatgcca gcattagcgt gcgggcccag gaccgctact atagctcatc    960
ttggagcgaa tggcatctg tgccctgcag tggtggcggt ggcggcggat ctagaaacct   1020
ccccgtggcc actccagacc caggaatgtt cccatgcctt caccactccc aaaacctgct   1080
gagggccgtc agcaacatgc tccagaaggc cagacaaact ctagaatttt acccttgcac   1140
ttctgaagag attgatcatg aagatataca aaaagataaa accagcacag tggaggcctg   1200
tttaccattg gaattaacca agaatgagag ttgcctaaat tccagagaga cctcttcat   1260
aactaatggg agttgcctgg cctccagaaa gacctctttt atgatggccc tgtgccttag   1320
tagtatttat gaagacttga agatgtacca ggtggagttc aagaccatga atgcaaagct   1380
tctgatggat cctaagaggc agatctttct agatcaaaac atgctggcag ttattgatga   1440
gctgatgcag gccctgaatt tcaacagtga gactgtgcca caaaaatcct cccttgaaga   1500
accggatttt tataaaacta aaatcaagct ctgcatactt cttcatgctt tcagaattcg   1560
ggcagtgact attgatagag tgatgagcta tctgaatgct tcctaagc                 1608
```

<210> SEQ ID NO 3
<211> LENGTH: 1632
<212> TYPE: DNA
<213> ORGANISM: Mus musculus

<400> SEQUENCE: 3

```
atgtgtcctc agaagctaac catctcctgg tttgccatcg ttttgctggt gtctccactc      60
atggccatgt gggagctgga aaagacgtt tatgttgtag aggtggactg gactcccgat    120
gccccctggag aaacagtgaa cctcacctgt gacacgcctg aagaagatga catcacctgg    180
acctcagacc agagacatgg agtcataggc tctggaaaga ccctgaccat cactgtcaaa    240
gagtttctag atgctggcca gtacacctgc cacaaaggag cgagactct gagccactca    300
catctgctgc tccacaagaa ggaaaatgga atttggtcca ctgaaatttt aaaaaatttc    360
aaaaacaaga ctttcctgaa gtgtgaagca ccaaattact ccggacgtt cacgtgctca    420
tggctggtgc aaagaaacat ggacttgaag ttcaacatca agagcagtag cagttcccct    480
```

-continued

```
gactctcggg cagtgacctg tggaatggcg tctctgtctg cagagaaggt cacactggac      540
caaagggact atgagaagta ttcagtgtcc tgccaggagg atgtcacctg cccaactgcc      600
gaggagaccc tgcccattga actggcgttg gaagcacggc agcagaataa atatgagaac      660
tacagcacca gcttcttcat cagggacatc atcaaaccag acccgcccaa gaacttgcag      720
atgaagcctt tgaagaactc acaggtggag gtcagctggg agtaccctga ctcctggagc      780
actccccatt cctacttctc cctcaagttc tttgttcgaa tccagcgcaa gaaagaaaag      840
atgaaggaga cagaggaggg gtgtaaccag aaaggtgcgt tcctcgtaga gaagacatct      900
accgaagtcc aatgcaaagg cgggaatgtc tgcgtgcaag ctcaggatcg ctattacaat      960
tcctcgtgca gcaagtgggc atgtgttccc tgcagggtcc gatccggtgg cggtggctcg     1020
ggcggtggtg ggtcgggtgg cggcggatct agggtcattc cagtctctgg acctgccagg     1080
tgtcttagcc agtcccgaaa cctgctgaag accacagatg acatggtgaa gacggccaga     1140
gaaaaactga acattattc ctgcactgct gaagacatcg atcatgaaga catcacacgg     1200
gaccaaaccc gcacattgaa gacctgtttc ccactggaac tacacaagaa cgagagttgc     1260
ctggctacta gagagacttc ttccacaaca agagggagct gcctgccccc acagaagacg     1320
tctttgatga tgaccctgtg ccttggtagc atctatgagg acttgaagat gtaccagaca     1380
gagttccagg ccatcaacgc agcacttcag aatcacaacc atcagcagat cattctagac     1440
aagggcatgc tggtggccat cgatgagctg atgcagtctc tgaatcataa tggcgagact     1500
ctgcgccaga aacctcctgt gggagaagca gacccttaca gagtgaaaat gaagctctgc     1560
atcctgcttc acgccttcag cacccgcgtc gtgaccatca cagggtgat gggctatctg     1620 agctccgcct ga                                                        1632

<210> SEQ ID NO 4
<211> LENGTH: 390
<212> TYPE: DNA
<213> ORGANISM: Homo sapiens

<400> SEQUENCE: 4
tcgaggtcga cggtatcgat aagcttgata tcgaattagg aggaaaaact gtttcataca      60
gaaggcgtca attaggagga aaaactgttt catacagaag gcgtcaatta ggaggaaaaa     120
ctgtttcata cagaaggcgt caattggtcc catcgaatta ggaggaaaaa ctgtttcata     180
cagaaggcgt caattaggag gaaaaactgt tcatacaga aggcgtcaat taggaggaaa     240
aactgtttca tacagaaggc gtcaattggt cccgggacat tttgacaccc ccataatatt     300
tttccagaat taacagtata aattgcatct cttgttcaag agttccctat cactctcttt     360
aatcactact cacagtaacc tcaactcctg                                      390

<210> SEQ ID NO 5
<211> LENGTH: 7574
<212> TYPE: DNA
<213> ORGANISM: Artificial Sequence
<220> FEATURE:
<223> OTHER INFORMATION: Synthetic

<400> SEQUENCE: 5
tcgaggtcga cggtatcgat aagcttgata tcgaattagg aggaaaaact gtttcataca      60
gaaggcgtca attaggagga aaaactgttt catacagaag gcgtcaatta ggaggaaaaa     120
ctgtttcata cagaaggcgt caattggtcc catcgaatta ggaggaaaaa ctgtttcata     180
cagaaggcgt caattaggag gaaaaactgt tcatacaga aggcgtcaat taggaggaaa     240
```

```
aactgtttca tacagaaggc gtcaattggt cccgggacat tttgacaccc ccataatatt      300
tttccagaat taacagtata aattgcatct cttgttcaag agttccctat cactctcttt      360
aatcactact cacagtaacc tcaactcctg aattccatgg ccatgtgtca tcagcagctg      420
gtcatcagct ggttcagcct ggtgttcctg gccagccccc tggtggccat ctgggagctg      480
aagaaagacg tgtacgtggt ggagctggac tggtatcccg acgccctgg cgagatggtg       540 gtgctgacct gcgacacccc cgaagaggac ggcatcacct ggaccctgga ccagagcagc      600
gaggtgctgg gcagcggcaa gacccctgacc atccaggtca agagttcgg cgacgccggc      660 cagtacacct gccacaaggg cggcgaagtg ctgtcccaca gcctgctgct gctgcacaag      720
aaagaggatg gcatctggtc caccgacatc ctgaaggacc agaaagagcc caagaacaag      780
accttcctgc ggtgcgaggc caagaactac agcggccggt tcacctgttg gtggctgacc      840
accatcagca ccgacctgac cttcagcgtg aagagcagcc ggggcagcag cgaccctcag      900
ggcgtgacct gcggagccgc cacccctgagc gccgagagag tgcggggcga caacaaagag      960
tacgagtaca gcgtcgagtg ccaggaagat agccgcctgcc ctgccgccga ggaaagcctg     1020
cccatcgagg tgatggtgga cgccgtgcac aagctgaagt acgagaacta cacctccagc     1080 ttttcatcc gggacatcat caagcccgac cccccaaga acctgcagct gaagcccctg       1140
aagaacagcc ggcaggtgga ggtgtcctgg gagtaccctg acacctggtc cacccccac      1200 agctacttca gcctgacctt ctgtgtgcag gtgcagggca agagcaagcg ggagaagaaa     1260
gaccgggtgt tcaccgacaa gaccagcgcc ccgtgatct gccggaagaa cgccagcatc     1320
agcgtgcggg cccaggaccg gtactacagc agctcctggt ccgagtgggc cagcgtgccc     1380
tgcagcggcg ggggggcgg aggaagccgg aacctgcccg tggctacccc cgaccccggc      1440
atgttcccct gcctgcacca cagccagaac ctgctgcggg ccgtgagcaa catgctgcag     1500
aaggcccggc agaccctgga attctacccc tgcaccagcg aggaaatcga ccacgaggac     1560
atcaccaagg ataagaccag caccgtggag gcctgcctgc ccctggaact gaccaagaac     1620
gagagctgtc tgaactctcg ggagacaagc ttcatcacca acggctcttg cctggccagc     1680
agaaagacca gcttcatgat ggccctgtgc ctgagcagca tctacgagga cctgaagatg     1740
taccaggtgg agttcaagac catgaacgcc aagctgctga tggaccccaa gcggcagatc     1800
ttcctggatc agaacatgct ggccgtgatc gacgagctga tgcaggccct gaacttcaac     1860
agcgagacag tgccccagaa gtccagcctg gaagagcccg acttctacaa gaccaagatc     1920
aagctgtgca tcctcctgca tgccttccgg atccgggccg tgaccatcga ccgggtgatg     1980
agctacctga acgccagctg atgagcggcc gctacgtaga tcgacggatc cctcgagctc     2040
aagcttcgaa ttctgcagtc gacggtaccg cgggcccaat tcgagctcgg tacctttaag     2100
accaatgact acaaggcag ctgtagatct tagccacttt ttaaaagaaa agggggact       2160 ggaagggcta attcactccc aacgaagaca agatctgctt tttgcttgta ctgggtctct     2220
ctggttagac cagatctgag cctgggagct ctctggctaa ctaggaacc cactgcttaa      2280 gcctcaataa agcttgcctt gagtgcttca agtagtgtgt gcccgtctgt tgtgtgactc     2340
tggtaactag agatccctca gacccttttta gtcagtgtgg aaaatctcta gcagtagtag     2400
ttcatgtcat cttattattc agtatttata acttgcaaag aaatgaatat cagagagtga     2460
gaggaacttg tttattgcag cttataatgg ttacaaataa agcaatagca tcacaaattt     2520
cacaaataaa gcatttttt cactgcattc tagttgtggt ttgtccaaac tcatcaatgt      2580
atcttatcat gtctggctct agctatcccg cccctaactc cgcccagttc cgcccattct     2640
```

```
ccgccccatg gctgactaat ttttttatt tatgcagagg ccgaggccgc ctcggcctct    2700
gagctattcc agaagtagtg aggaggcttt tttggaggcc taggcttttg cgtcgagacg    2760
tacccaattc gccctatagt gagtcgtatt acgcgcgctc actggccgtc gttttacaac    2820
gtcgtgactg ggaaaaccct ggcgttaccc aacttaatcg ccttgcagca catccccctt    2880
tcgccagctg gcgtaatagc gaagaggccc gcaccgatcg cccttcccaa cagttgcgca    2940
gcctgaatgg cgaatggcgc gacgcgccct gtagcggcgc attaagcgcg gcgggtgtgg    3000
tggttacgcg cagcgtgacc gctacacttg ccagcgccct agcgcccgct cctttcgctt    3060
tcttcccttc ctttctcgcc acgttcgccg gctttccccg tcaagctcta atcggggc    3120 tcccttagg gttccgattt agtgctttac ggcacctcga ccccaaaaaa cttgattagg    3180
gtgatggttc acgtagtggg ccatcgccct gatagacggt ttttcgccct ttgacgttgg    3240
agtccacgtt ctttaatagt ggactcttgt tccaaactgg aacaacactc aaccctatct    3300
cggtctattc ttttgattta aagggattt tgccgatttc ggcctattgg ttaaaaaatg    3360
agctgattta acaaaaattt aacgcgaatt ttaacaaaat attaacgttt acaatttccc    3420
aggtggcact tttcggggaa atgtgcgcgg aaccccctatt tgtttatttt tctaaataca    3480
ttcaaatatg tatccgctca tgagacaata accctgataa atgcttcaat aatattgaaa    3540
aaggaagagt atgagtattc aacatttccg tgtcgccctt attcccttt ttgcggcatt    3600 ttgccttcct gtttttgctc acccagaaac gctggtgaaa gtaaaagatg ctgaagatca    3660
gttgggtgca cgagtgggtt acatcgaact ggatctcaac agcggtaaga tccttgagag    3720
ttttcgcccc gaagaacgtt ttccaatgat gagcactttt aaagttctgc tatgtggcgc    3780
ggtattatcc cgtattgacg ccgggcaaga gcaactcggt cgccgcatac actattctca    3840
gaatgacttg gttgagtact caccagtcac agaaaagcat cttacggatg gcatgacagt    3900
aagagaatta tgcagtgctg ccataaccat gagtgataac actgcggcca acttacttct    3960
gacaacgatc ggaggaccga aggagctaac cgcttttttg cacaacatgg gggatcatgt    4020
aactcgcctt gatcgttggg aaccggagct gaatgaagcc ataccaaacg acgagcgtga    4080
caccacgatg cctgtagcaa tggcaacaac gttgcgcaaa ctattaactg gcgaactact    4140
tactctagct tcccggcaac aattaataga ctggatggag gcggataaag ttgcaggacc    4200
acttctgcgc tcggcccttc cggctggctg gtttattgct gataaatctg gagccggtga    4260
gcgtgggtct cgcggtatca ttgcagcact ggggccagat ggtaagccct cccgtatcgt    4320
agttatctac acgacgggga gtcaggcaac tatgatgaa cgaaatagac agatcgctga    4380
gataggtgcc tcactgatta agcattggta actgtcagac caagtttact catatatact    4440
ttagattgat ttaaaacttc attttaatt taaaaggatc taggtgaaga tcctttttga    4500
taatctcatg accaaaatcc cttaacgtga gttttcgttc cactgagcgt cagaccccgt    4560
agaaaagatc aaaggatctt cttgagatcc ttttttctg cgcgtaatct gctgcttgca    4620
aacaaaaaaa ccaccgctac cagcggtggt ttgtttgccg gatcaagagc taccaactct    4680
ttttccgaag gtaactggct tcagcagagc gcagatacca aatactgtcc ttctagtgta    4740
gccgtagtta ggccaccact tcaagaactc tgtagcaccg cctacatacc tcgctctgct    4800
aatcctgtta ccagtggctg ctgccagtgg cgataagtcg tgtcttaccg ggttggactc    4860
aagacgatag ttaccggata aggcgcagcg tcgggctga acggggggtt cgtgcacaca    4920
gcccagcttg gagcgaacga cctacaccga actgagatac ctacagcgtg agctatgaga    4980
aagcgccacg cttcccgaag ggagaaaggc ggacaggtat ccggtaagcg cagggtcgg    5040
```

```
aacaggagag cgcacgaggg agcttccagg gggaaacgcc tggtatcttt atagtcctgt    5100
cgggtttcgc cacctctgac ttgagcgtcg attttgtga tgctcgtcag gggggcggag    5160
cctatggaaa aacgccagca acgcggcctt tttacggttc ctggccttt gctggctttt    5220 tgctcacatg ttctttcctg cgttatcccc tgattctgtg gataaccgta ttaccgcctt    5280
tgagtgagct gataccgctc gccgcagccg aacgaccgag cgcagcgagt cagtgagcga    5340
ggaagcggaa gagcgcccaa tacgcaaacc gcctctcccc gcgcgttggc cgattcatta    5400
atgcagctgg cacgacaggt ttcccgactg gaaagcgggc agtgagcgca acgcaattaa    5460
tgtgagttag ctcactcatt aggcacccca ggctttacac tttatgcttc cggctcgtat    5520
gttgtgtgga attgtgagcg gataacaatt tcacacagga aacagctatg accatgatta    5580
cgccaagcgc gcaattaacc ctcactaaag ggaacaaaag ctggagctgc aagcttaatg    5640
tagtcttatg caatactctt gtagtcttgc aacatggtaa cgatgagtta gcaacatgcc    5700
ttacaaggag agaaaaagca ccgtgcatgc cgattggtgg aagtaaggtg gtacgatcgt    5760
gccttattag gaaggcaaca gacgggtctg acatggattg gacgaaccac tgaattgccg    5820
cattgcagag atattgtatt taagtgccta gctcgataca ataaacgggt ctctctggtt    5880
agaccagatc tgagcctggg agctctctgg ctaactaggg aacccactgc ttaagcctca    5940
ataaagcttg ccttgagtgc ttcaagtagt gtgtgcccgt ctgttgtgtg actctggtaa    6000
ctagagatcc ctcagaccct tttagtcagt gtggaaaatc tctagcagtg gcgcccgaac    6060
agggacctga agcgaaagg gaaaccgag ctctctcgac gcaggactcg gcttgctgaa    6120
gcgcgcacgg caagaggcga ggggcggcga ctggtgagta cgccaaaaat tttgactagc    6180
ggaggctaga aggagagaga tgggtgcgag agcgtcagta ttaagcgggg gagaattaga    6240
tcgcgatggg aaaaaattcg gttaaggcca ggggggaaaga aaaatataa attaaaacat    6300 atagtatggg caagcaggga gctagaacga ttcgcagtta atcctggcct gttagaaaca    6360
tcagaaggct gtagacaaat actgggacag ctacaaccat cccttcagac aggatcagaa    6420
gaacttagat cattatataa tacagtagca acctctctatt gtgtgcatca aaggatagag    6480
ataaaagaca ccaaggaagc tttagacaag atagaggaag agcaaaacaa aagtaagacc    6540
accgcacagc aagcggccgc tgatcttcag acctggagga ggagatatga gggacaattg    6600
gagaagtgaa ttatataaat ataaagtagt aaaaattgaa ccattaggag tagcacccac    6660
caaggcaaag agaagagtgg tgcagagaga aaaaagagca gtgggaatag gagctttgtt    6720
ccttgggttc ttgggagcag caggaagcac tatgggcgca gcctcaatga cgctgacggt    6780
acaggccaga caattattgt ctggtatagt gcagcagcag aacaatttgc tgagggctat    6840
tgaggcgcaa cagcatctgt tgcaactcac agtctgggc atcaagcagc tccaggcaag    6900
aatcctggct gtggaaagat acctaaagga tcaacagctc ctggggattt ggggttgctc    6960
tggaaaactc atttgcacca ctgctgtgcc ttggaatgct agttggagta ataaatctct    7020
ggaacagatt tggaatcaca cgacctggat ggagtgggac agagaaatta acaattacac    7080
aagcttaata cactccttaa ttgaagaatc gcaaaccag caagaaaaga atgaacaaga    7140
attattggaa ttagataaat gggcaagttt gtggaattgg tttaacataa caaattggct    7200
gtggtatata aaattattca taatgatagt aggaggcttg gtaggtttaa gaatagtttt    7260
tgctgtactt tctatagtga atagagttag gcagggatat tcaccattat cgtttcagac    7320
ccacctccca accccgaggg gacccgacag gcccgaagga atagaagaag aaggtggaga    7380
gagagacaga gacagatcca ttcgattagt gaacggatct cgacggtatc ggttaacttt    7440
```

```
taaaagaaaa gggggattg gggggtacag tgcagggaa agaatagtag acataatagc    7500
aacagacata caaactaaag aattacaaaa acaaattaca aaaattcaaa attttatcga    7560
tcacgagact agcc                                                      7574

<210> SEQ ID NO 6
<211> LENGTH: 6712
<212> TYPE: DNA
<213> ORGANISM: Artificial Sequence
<220> FEATURE:
<223> OTHER INFORMATION: Synthetic

<400> SEQUENCE: 6
ggccgcgtcg tcggatcccc cgggctgcag gaattcgagc atcttaccgc catttatacc      60
catatttgtt ctgtttttct tgatttgggt atacatttaa atgttaataa acaaaatgg     120 tgggcaatc atttacattt ttagggatat gtaattacta gttcaggtgt attgccacaa     180
gacaaacatg ttaagaaact ttcccgttat ttacgctctg ttcctgttaa tcaacctctg     240
gattacaaaa tttgtgaaag attgactgat attcttaact atgttgctcc ttttacgctg     300
tgtggatatg ctgctttaat gcctctgtat catgctattg cttcccgtac ggctttcgtt     360
ttctcctcct tgtataaatc tggttgctg tctctttatg aggagttgtg gcccgttgtc     420
cgtcaacgtg gcgtggtgtg ctctgtgttt gctgacgcaa cccccactgg ctggggcatt     480
gccaccacct gtcaactcct ttctgggact ttcgctttcc cctcccgat cgccacggca     540 gaactcatcg ccgcctgcct tgcccgctgc tggacagggg ctaggttgct gggcactgat     600
aattccgtgg tgttgtcggg gaagctgacg tcctttcgaa ttcgatatca gcttaacac     660 gagccataga tagaataaaa gattttattt agtctccaga aaagggggg aatgaaagac     720 cccaccgcta gcgatatcga attcacaacc cctcactcgg cgcgccagtc tccgacaga     780 ctgagtcgcc cgggtacccg tgttctcaat aaaccctctt gcagttgcat ccgactcgtg     840
gtctcgctgt tccttgggag gtctcctct gagtgattga ctgcccacct cggggggtctt     900 tcattctcga gagctttggc gtaatcatgg tcatagctgt ttcctgtgtg aaattgttat     960
ccgctcacaa ttccacacaa catacgagcc ggaagcataa agtgtaaagc ctggggtgcc    1020
taatgagtga gctaactcac attaattgcg ttgcgctcac tgcccgcttt ccagtcggga    1080
aacctgtcgt gccagctgca ttaatgaatc ggccaacgcg cggggagagg cggtttgcgt    1140
attgggcgct cttccgcttc ctcgctcact gactcgctgc gctcggtcgt tcggctgcgg    1200
cgagcggtat cagctcactc aaaggcggta atacggttat ccacagaatc aggggataac    1260
gcaggaaaga acatgtgagc aaaaggccag caaaaggcca ggaaccgtaa aaaggccgcg    1320
ttgctggcgt ttttccatag gctccgcccc cctgacgagc atcacaaaaa tcgacgctca    1380
agtcagaggt ggcgaaaccc gacaggacta taaagatacc aggcgtttcc ccctggaagc    1440
tccctcgtgc gctctcctgt tccgaccctg ccgcttaccg gatacctgtc cgcctttctc    1500
ccttcgggaa gcgtggcgct ttctcaatgc tcacgctgta ggtatctcag ttcggtgtag    1560
gtcgttcgct ccaagctggg ctgtgtgcac gaaccccccg ttcagcccga ccgctgcgcc    1620
ttatccggta actatcgtct tgagtccaac ccggtaagac acgacttatc gccactggca    1680
gcagccactg gtaacaggat tagcagagcg aggtatgtag cggtgctac agagttcttg    1740 aagtggtggc ctaactacgg ctacactaga aggacagtat ttggtatctg cgctctgctg    1800
aagccagtta ccttcggaaa aagagttggt agctcttgat ccggcaaaca accaccgct    1860 ggtagcggtg gtttttttgt ttgcaagcag cagattacgc gcagaaaaaa aggatctcaa    1920
```

```
gaagatcctt tgatctttc tacggggtct gacgctcagt ggaacgaaaa ctcacgttaa    1980
gggattttgg tcatgagatt atcaaaaagg atcttcacct agatcctttt aaattaaaaa    2040
tgaagtttta aatcaatcta agtatatat gagtaaactt ggtctgacag ttaccaatgc    2100
ttaatcagtg aggcacctat ctcagcgatc tgtctatttc gttcatccat agttgcctga    2160
ctccccgtcg tgtagataac tacgatacg gagggcttac catctggccc cagtgctgca    2220
atgataccgc gagacccacg ctcaccggct ccagatttat cagcaataaa ccagccagcc    2280
ggaagggccg agcgcagaag tggtcctgca actttatccg cctccatcca gtctattaat    2340
tgttgccggg aagctagagt aagtagttcg ccagttaata gtttgcgcaa cgttgttgcc    2400
attgctgctg gcatcgtggt gtcacgctcg tcgtttggta tggcttcatt cagctccggt    2460
tcccaacgat caaggcgagt tacatgatcc cccatgttgt gcaaaaaagc ggttagctcc    2520
ttcggtcctc cgatcgttgt cagaagtaag ttggccgcag tgttatcact catggttatg    2580
gcagcactgc ataattctct tactgtcatg ccatccgtaa gatgctttc tgtgactggt    2640
gagtactcaa ccaagtcatt ctgagaatag tgtatgcggc gaccgagttg ctcttgcccg    2700
gcgtcaatac gggataatac cgcgccacat agcagaactt taaaagtgct catcattgga    2760
aaacgttctt cggggcgaaa actctcaagg atcttaccgc tgttgagatc cagttcgatg    2820
taacccactc gtgcacccaa ctgatcttca gcatctttta ctttcaccag cgtttctggg    2880
tgagcaaaaa caggaaggca aaatgccgca aaaagggaa taagggcgac acggaaatgt    2940
tgaatactca tactcttcct ttttcaatat tattgaagca tttatcaggg ttattgtctc    3000
atgagcggat acatatttga atgtatttag aaaaataaac aaatagggt tccgcgcaca    3060
tttccccgaa aagtgccacc tgacgtctaa gaaaccatta ttatcatgac attaacctat    3120
aaaaatagc gtatcacgag gccctttcgt cttcaagctg cctcgcgcgt ttcggtgatg    3180
acggtgaaaa cctctgacac atgcagctcc cggagacggt cacagcttgt ctgtaagcgg    3240
atgccgggag cagacaagcc cgtcagggcg cgtcagcggg tgttggcggg tgtcggggcg    3300
cagccatgac ccagtcacgt agcgatagtt actatgcggc atcagagcag attgtactga    3360
gagtgcacca tatgcggtgt gaaataccgc acagatgcgt aaggagaaaa taccgcatca    3420
ggcgccattc gccattcagg ctgcgcaact gttgggaagg gcgatcggtg cgggcctctt    3480
cgctattacg ccagctggcg aaagggggat gtgctgcaag gcgattaagt tgggtaacgc    3540
cagggttttc ccagtcacga cgttgtaaaa cgacggccag tgaattagta ctctagctta    3600
agacgcgtgg cctgaaataa cctctgaaag aggaacttgg ttaggtacct tctgaggcgg    3660
aaagaaccag ctgtggaatg tgtgtcagtt agggtgtgga aagtcccag gctccccagc    3720
aggcagaagt atgcaaagca tgcatctcaa ttagtcagca accaggtgtg gaaagtcccc    3780
aggctcccca gcaggcagaa gtatgcaaag catgcatctc aattagtcag caaccatagt    3840
cccttaagaa tgtagtctta tgcaatactc ttgtagtctt gcaacatggt aacgatgagt    3900
tagcaacatg ccttacaagg agagaaaaag caccgtgcat gccgattggt ggaagtaagg    3960
tggtacgatc gtgccttatt aggaaggcaa cagacgggtc tgacatggat tggacgaacc    4020
actgaattgc cgcattgcag agatattgta tttaagtgcc tagctcgata caataaacgc    4080
gccagtcctc cgattgactg cgtcgcccgg gtacccgtat tcccaataaa gcctcttgct    4140
gtttgcatcc gaatcgtgga ctcgctgatc cttgggaggg tctcctcaga ttgattgact    4200
gcccacctcg ggggtctttc atttggaggt tccaccgaga tttggagacc cctgcccagg    4260
gaccaccgac ccccccgccg ggaggtaagc tggccagcgg tcgtttcgtg tctgtctctg    4320
```

```
tctttgggcg tgtttgtgcc ggcatctagt gtttgcgcct gcgtctgtac tagttggcta   4380
actagatctg tatctggcgg tcccgcggaa gaactgacga gttcgtattc cggccgcag    4440
cccctgggag acgtcccagc ggcctcgggg gcccgttttg tggcccattc tgtatcagtt   4500
aacctacccg agtcggactt tttggagctc cgccactgtc cgaggggtac gtggctttgt   4560
tgggggacga gagacagaga cacttcccgc ccccgtctga attttttgctt tcggttttac   4620
gccgaaaccg cgccgcgcgt cttgtctgct gcagcatcgt tctgtgttgt ctctgtctga   4680
cgtggttctg tattgtctga aaatagtcga ggtcgacggt atcgataagc ttgatatcga   4740
attaggagga aaaactgttt catacagaag gcgtcaatta ggaggaaaaa ctgtttcata   4800
cagaaggcgt caattaggag gaaaaactgt tcatacaga aggcgtcaat tggtcccatc    4860
gaattaggag gaaaaactgt tcatacaga aggcgtcaat taggaggaaa aactgtttca    4920
tacagaaggc gtcaattagg aggaaaaact gtttcataca gaaggcgtca attggtcccg   4980
ggacattttg acccccccat aatattttc cagaattaac agtataaatt gcatctcttg    5040
ttcaagagtt ccctatcact ctctttaatc actactcaca gtaacctcaa ctcctgaatt   5100
ccatggccat gtgtcatcag cagctggtca tcagctggtt cagcctggtg ttcctggcca   5160
gcccctggt ggccatctgg gagctgaaga agacgtgta cgtggtggag ctggactggt     5220
atcccgacgc ccctggcgag atggtggtgc tgacctgcga caccccgaa gaggacggca    5280
tcacctggac cctggaccag agcagcgagg tgctgggcag cggcaagacc ctgaccatcc   5340
aggtcaaaga gttcggcgac gccggccagt acacctgcca aagggcggc gaagtgctgt    5400
cccacagcct gctgctgctg cacaagaaag aggatggcat ctggtccacc gacatcctga   5460
aggaccagaa agagcccaag aacaagacct tcctgcggtg cgaggccaag aactacagcg   5520
gccggttcac ctgttggtgg ctgaccacca tcagcaccga cctgaccttc agcgtgaaga   5580
gcagccgggg cagcagcgac cctcagggcg tgacctgcgg agccgccacc ctgagcgccg   5640
agagagtgcg gggcgacaac aaagagtacg agtacagcgt cgagtgccag gaagatagcg   5700
cctgccctgc cgccgaggaa agcctgccca tcgaggtgat ggtggacgcc gtgcacaagc   5760
tgaagtacga gaactacacc tccagctttt tcatccggga catcatcaag cccgaccccc   5820
ccaagaacct gcagctgaag cccctgaaga cagccggca ggtggaggtg tcctgggagt    5880
accctgacac ctggtccacc cccacagct acttcagcct gaccttctgt gtgcaggtgc    5940
agggcaagag caagcgggag aagaaagacc gggtgttcac cgacaagacc agcgccaccg   6000
tgatctgccg gaagaacgcc agcatcagcg tgcgggccca ggaccggtac tacagcagct   6060
cctggtccga gtgggccagc gtgccctgca gcggcggagg gggcggagga agccggaacc   6120
tgcccgtggc tacccccgac cccggcatgt tcccctgcct gcaccacagc cagaacctgc   6180
tgcgggccgt gagcaacatg ctgcagaagg cccggcagac cctggaattc taccccctgca   6240
ccagcgagga aatcgaccac gaggacatca ccaaggataa gaccagcacc gtggaggcct   6300
gcctgccct ggaactgacc aagaacgaga gctgtctgaa ctctcgggag acaagcttca    6360
tcaccaacgg ctcttgcctg gccagcagaa agaccagctt catgatggcc ctgtgcctga   6420
gcagcatcta cgaggacctg aagatgtacc aggtggagtt caagaccatg aacgccaagc   6480
tgctgatgga ccccaagcgg cagatcttcc tggatcagaa catgctggcc gtgatcgacg   6540
agctgatgca ggccctgaac ttcaacagcg agacagtgcc ccagaagtcc agcctggaag   6600
agcccgactt ctacaagacc aagatcaagc tgtgcatcct cctgcatgcc ttccggatcc   6660
gggccgtgac catcgaccgg gtgatgagct acctgaacgc cagctgatga gc           6712
```

<210> SEQ ID NO 7
<211> LENGTH: 6120
<212> TYPE: DNA
<213> ORGANISM: Artificial Sequence
<220> FEATURE:
<223> OTHER INFORMATION: Synthetic

<400> SEQUENCE: 7

| | | | | | |
|---|---|---|---|---|---|
| catggaattc | aggagttgag | gttactgtga | gtagtgatta | agagagtga | tagggaactc | 60 |
| ttgaacaaga | gatgcaattt | atactgttaa | ttctggaaaa | atattatggg | ggtgtcaaaa | 120 |
| tgtcccggga | ccaattgacg | ccttctgtat | gaaacagttt | ttcctcctaa | ttgacgcctt | 180 |
| ctgtatgaaa | cagttttttcc | tcctaattga | cgccttctgt | atgaaacagt | ttttcctcct | 240 |
| aattcgatgg | gaccaattga | cgccttctgt | atgaaacagt | ttttcctcct | aattgacgcc | 300 |
| ttctgtatga | acagttttt | cctcctaatt | gacgccttct | gtatgaaaca | gttttcctc | 360 |
| ctaattcgat | atcaagctta | acacgagcca | tagatagaat | aaaagatttt | atttagtctc | 420 |
| cagaaaaagg | ggggaatgaa | agaccccacc | gctagcgata | tcgaattcac | aacccctcac | 480 |
| tcggcgcgcc | agtcctccga | cagactgagt | cgcccgggta | cccgtgttct | caataaaccc | 540 |
| tcttgcagtt | gcatccgact | cgtggtctcg | ctgttccttg | ggagggtctc | ctctgagtga | 600 |
| ttgactgccc | acctcggggg | tctttcattc | tcgagagctt | tggcgtaatc | atggtcatag | 660 |
| ctgtttcctg | tgtgaaattg | ttatccgctc | acaattccac | acaacatacg | agccggaagc | 720 |
| ataaagtgta | aagcctgggg | tgcctaatga | gtgagctaac | tcacattaat | tgcgttgcgc | 780 |
| tcactgcccg | ctttccagtc | gggaaacctg | tcgtgccagc | tgcattaatg | aatcggccaa | 840 |
| cgcgcgggga | gaggcggttt | gcgtattggg | cgctcttccg | cttcctcgct | cactgactcg | 900 |
| ctgcgctcgg | tcgttcggct | gcggcgagcg | gtatcagctc | actcaaaggc | ggtaatacgg | 960 |
| ttatccacag | aatcagggga | taacgcagga | aagaacatgt | gagcaaaagg | ccagcaaaag | 1020 |
| gccaggaacc | gtaaaaaggc | cgcgttgctg | gcgttttttcc | ataggctccg | cccccctgac | 1080 |
| gagcatcaca | aaaatcgacg | ctcaagtcag | aggtggcgaa | acccgacagg | actataaaga | 1140 |
| taccaggcgt | ttccccctgg | aagctccctc | gtgcgctctc | ctgttccgac | cctgccgctt | 1200 |
| accggatacc | tgtccgcctt | tctcccttcg | ggaagcgtgg | cgctttctca | atgctcacgc | 1260 |
| tgtaggtatc | tcagttcggt | gtaggtcgtt | cgctccaagc | tgggctgtgt | gcacgaaccc | 1320 |
| cccgttcagc | ccgaccgctg | cgccttatcc | ggtaactatc | gtcttgagtc | caacccggta | 1380 |
| agacacgact | tatcgccact | ggcagcagcc | actggtaaca | ggattagcag | agcgaggtat | 1440 |
| gtaggcggtg | ctacagagtt | cttgaagtgg | tggcctaact | acggctacac | tagaaggaca | 1500 |
| gtatttggta | tctgcgctct | gctgaagcca | gttaccttcg | gaaaaagagt | tggtagctct | 1560 |
| tgatccggca | aacaaaccac | cgctggtagc | ggtggttttt | ttgtttgcaa | gcagcagatt | 1620 |
| acgcgcagaa | aaaaggatc | tcaagaagat | cctttgatct | tttctacggg | gtctgacgct | 1680 |
| cagtggaacg | aaaactcacg | ttaagggatt | ttggtcatga | gattatcaaa | aaggatcttc | 1740 |
| acctagatcc | ttttaaatta | aaaatgaagt | tttaaatcaa | tctaaagtat | atatgagtaa | 1800 |
| acttggtctg | acagttacca | atgcttaatc | agtgaggcac | ctatctcagc | gatctgtcta | 1860 |
| tttcgttcat | ccatagttgc | ctgactcccc | gtcgtgtaga | taactacgat | acgggagggc | 1920 |
| ttaccatctg | gccccagtgc | tgcaatgata | ccgcgagacc | cacgctcacc | ggctccagat | 1980 |
| ttatcagcaa | taaaccagcc | agccggaagg | gccgagcgca | gaagtggtcc | tgcaacttta | 2040 |
| tccgcctcca | tccagtctat | taattgttgc | cgggaagcta | gagtaagtag | ttcgccagtt | 2100 |

```
aatagtttgc gcaacgttgt tgccattgct gctggcatcg tggtgtcacg ctcgtcgttt      2160
ggtatggctt cattcagctc cggttcccaa cgatcaaggc gagttacatg atcccccatg      2220
ttgtgcaaaa aagcggttag ctccttcggt cctccgatcg ttgtcagaag taagttggcc      2280
gcagtgttat cactcatggt tatggcagca ctgcataatt ctcttactgt catgccatcc      2340
gtaagatgct tttctgtgac tggtgagtac tcaaccaagt cattctgaga atagtgtatg      2400
cggcgaccga gttgctcttg cccggcgtca atacgggata ataccgcgcc acatagcaga      2460
actttaaaag tgctcatcat tggaaaacgt tcttcggggc gaaaactctc aaggatctta      2520
ccgctgttga gatccagttc gatgtaaccc actcgtgcac ccaactgatc ttcagcatct      2580
tttactttca ccagcgtttc tgggtgagca aaaacaggaa ggcaaaatgc cgcaaaaaag      2640
ggaataaggg cgacacggaa atgttgaata ctcatactct tcctttttca atattattga      2700
agcatttatc agggttattg tctcatgagc ggatacatat ttgaatgtat ttagaaaaat      2760
aaacaaatag gggttccgcg cacatttccc cgaaaagtgc cacctgacgt ctaagaaacc      2820
attattatca tgacattaac ctataaaaat aggcgtatca cgaggccctt tcgtcttcaa      2880
gctgcctcgc gcgtttcggt gatgacgtg aaaacctctg acacatgcag ctcccggaga      2940
cggtcacagc ttgtctgtaa gcggatgccg ggagcagaca agcccgtcag ggcgcgtcag      3000
cgggtgttgg cgggtgtcgg ggcgcagcca tgacccagtc acgtagcgat agttactatg      3060
cggcatcaga gcagattgta ctgagagtgc accatatgcg gtgtgaaata ccgcacagat      3120
gcgtaaggag aaaataccgc atcaggcgcc attcgccatt caggctgcgc aactgttggg      3180
aagggcgatc ggtgcgggcc tcttcgctat tacgccagct ggcgaaaggg ggatgtgctg      3240
caaggcgatt aagttgggta acgccagggt tttcccagtc acgacgttgt aaaacgacgg      3300
ccagtgaatt agtactctag cttaagacgc gtggcctgaa ataacctctg aaagaggaac      3360
ttggttaggt accttctgag gcggaaagaa ccagctgtgg aatgtgtgtc agttagggtg      3420
tggaaagtcc ccaggctccc cagcaggcag aagtatgcaa agcatgcatc tcaattagtc      3480
agcaaccagg tgtggaaagt ccccaggctc cccagcaggc agaagtatgc aaagcatgca      3540
tctcaattag tcagcaacca tagtccctta gaatgtagt cttatgcaat actcttgtag      3600
tcttgcaaca tggtaacgat gagttagcaa catgccttac aaggagagaa aaagcaccgt      3660
gcatgccgat tggtggaagt aaggtggtac gatcgtgcct tattaggaag gcaacagacg      3720
ggtctgacat ggattggacg aaccactgaa ttgccgcatt gcagagatat tgtatttaag      3780
tgcctagctc gatacaataa acgcgccagt cctccgattg actgcgtcgc ccgggtaccc      3840
gtattcccaa taaagcctct tgctgtttgc atccgaatcg tggactcgct gatccttggg      3900
agggtctcct cagattgatt gactgcccac ctcgggggtc tttcatttgg aggttccacc      3960
gagatttgga gaccctgcc cagggaccac cgaccccccc gccggaggt aagctggcca      4020 gcggtcgttt cgtgtctgtc tctgtctttg ggcgtgtttg tgccggcatc tagtgtttgc      4080
gcctgcgtct gtactagttg gctaactaga tctgtatctg gcggtcccgc ggaagaactg      4140
acgagttcgt attcccggcc gcagcccctg ggagacgtcc cagcggcctc gggggcccgt      4200
tttgtggccc attctgtatc agttaaccta cccgagtcgg acttttggaa gctccgccac      4260
tgtccgaggg gtacgtggct tgttgggggg acgagagaca gagacacttc ccgccccgt      4320 ctgaattttt gctttcggtt ttacgccgaa accgcgccgc gcgtcttgtc tgctgcagca      4380
tcgttctgtg ttgtctctgt ctgacgtggt tctgtattgt ctgaaaatag tcgaggatat      4440
ccccgtcacg tggatcctca cacaaaaaac caacacacag atgtaatgaa aataaagata      4500
```

```
ttttattgcg gccgctcatc agctggcgtt caggtagctc atcacccggt cgatggtcac    4560
ggcccggatc cggaaggcat gcaggaggat gcacagcttg atcttggtct tgtagaagtc    4620
gggctcttcc aggctggact tctggggcac tgtctcgctg ttgaagttca gggcctgcat    4680
cagctcgtcg atcacggcca gcatgttctg atccaggaag atctgccgct tggggtccat    4740
cagcagcttg gcgttcatgg tcttgaactc cacctggtac atcttcaggt cctcgtagat    4800
gctgctcagg cacagggcca tcatgaagct ggtctttctg ctggccaggc aagagccgtt    4860
ggtgatgaag cttgtctccc gagagttcag acagctctcg ttcttggtca gttccagggg    4920
caggcaggcc tccacggtgc tggtcttatc cttggtgatg tcctcgtggt cgatttcctc    4980
gctggtgcag gggtagaatt ccagggtctg ccgggccttc tgcagcatgt tgctcacggc    5040
ccgcagcagg ttctggctgt ggtgcaggca ggggaacatg ccggggtcgg gggtagccac    5100 ggcaggttc cggcttcctc cgcccctcc gccgctgcag gcacgctgg cccactcgga    5160 ccaggagctg ctgtagtacc ggtcctgggc ccgcacgctg atgctggcgt tcttccggca    5220
gatcacggtg gcgctggtct tgtcggtgaa cacccggtct ttcttctccc gcttgctctt    5280
gccctgcacc tgcacacaga aggtcaggct gaagtagctg tgggggggtgg accaggtgtc    5340 agggtactcc caggacacct ccacctgccg gctgttcttc aggggcttca gctgcaggtt    5400 cttgggggg tcgggcttga tgatgtcccg gatgaaaaag ctggaggtgt agttctcgta    5460
cttcagcttg tgcacggcgt ccaccatcac ctcgatgggc aggctttcct cggcggcagg    5520
gcaggcgcta tcttcctggc actcgacgct gtactcgtac tctttgttgt cgccccgcac    5580
tctctcggcg ctcagggtgg cggctccgca ggtcacgccc tgagggtcgc tgctgccccg    5640
gctgctcttc acgctgaagg tcaggtcggt gctgatggtg gtcagccacc aacaggtgaa    5700
ccggccgctg tagttcttgg cctcgcaccg caggaaggtc ttgttcttgg gctctttctg    5760
gtccttcagg atgtcggtgg accagatgcc atcctctttc ttgtgcagca gcagcaggct    5820
gtgggacagc acttcgccgc ccttgtggca ggtgtactgg ccggcgtcgc cgaactcttt    5880
gacctggatg tcagggtct tgccgctgcc cagcacctcg ctgctctggt ccagggtcca    5940
ggtgatgccg tcctcttcgg gggtgtcgca ggtcagcacc accatctcgc caggggcgtc    6000
gggataccag tccagctcca ccacgtacac gtctttcttc agctcccaga tggccaccag    6060
ggggctggcc aggaacacca ggctgaacca gctgatgacc agctgctgat gacacatggc    6120
```

<210> SEQ ID NO 8
<211> LENGTH: 5800
<212> TYPE: DNA
<213> ORGANISM: Artificial Sequence
<220> FEATURE:
<223> OTHER INFORMATION: Synthetic

<400> SEQUENCE: 8

```
ggccgctcga gcatgcatct agagggccct attctatagt gtcacctaaa tgctagagct     60
cgctgatcag cctcgactgt gccttctagt tgccagccat ctgttgtttg cccctccccc    120
gtgccttcct tgaccctgga agtgccact cccactgtcc tttcctaata aaatgaggaa    180
attgcatcgc attgtctgag taggtgtcat tctattctgg ggggtggggt ggggcaggac    240
agcaaggggg aggattggga agacaatagc aggcatgctg gggatgcggt gggctctatg    300
gcttctgagg cggaaagaac cagctgcatt aatggatccc cttgaaatac atccacaggt    360
acacctccaa ttgactcaaa tgatgtcaat tagtctatca gaagcttcta aagccatgac    420
atcattttct ggaattttcc aagctgttta aaggcacagt caacttagtg tatgtaaact    480
```

```
tctgacccac tggaattgtg atacagtgaa ttataagtga aataatctgt ctgtaaacaa    540
ttgttggaaa aatgacttgt gtcatgcaca aagtagatgt cctaactgac ttgccaaaac    600
tattgtttgt taacaagaaa tttgtggagt agttgaaaaa cgagttttaa tgactccaac    660
ttaagtgtat gtaaacttcc gacttcaact gtatatctag agtcgacctg caggcatgca    720
agcttggcgt aatcatggtc atagctgttt cctgtgtgaa attgttatcc gctcacaatt    780
ccacacaaca tacgagccgg aagcataaag tgtaaagcct ggggtgccta atgagtgagc    840
taactcacat taattgcgtt gcgctcactg cccgctttcc agtcgggaaa cctgtcgtgc    900
cagctgcatt aatgaatcgg ccaacgcgcg gggagaggcg gtttgcgtat tgggcgctct    960
tccgcttcct cgctcactga ctcgctgcgc tcggtcgttc ggctgcgcg agcggtatca    1020 gctcactcaa aggcggtaat acggttatcc acagaatcag gggataacgc aggaaagaac    1080
atgtgagcaa aaggccagca aaaggccagg aaccgtaaaa aggccgcgtt gctggcgttt    1140
ttccataggc tccgcccccc tgacgagcat cacaaaaatc gacgctcaag tcagaggtgg    1200
cgaaacccga caggactata aagataccag gcgtttcccc ctggaagctc cctcgtgcgc    1260
tctcctgttc cgaccctgcc gcttaccgga tacctgtccg cctttctccc ttcgggaagc    1320
gtggcgcttt ctcaatgctc acgctgtagg tatctcagtt cggtgtaggt cgttcgctcc    1380
aagctgggct gtgtgcacga accccccgtt cagcccgacc gctgcgcctt atccggtaac    1440
tatcgtcttg agtccaaccc ggtaagacac gacttatcgc cactggcagc agccactggt    1500
aacaggatta gcagagcgag gtatgtaggc ggtgctacag agttcttgaa gtggtggcct    1560
aactacggct acactagaag gacagtattt ggtatctgcg ctctgctgaa gccagttacc    1620
ttcggaaaaa gagttggtag ctcttgatcc ggcaaacaaa ccaccgctgg tagcggtggt    1680
ttttttgttt gcaagcagca gattacgcgc agaaaaaaag gatctcaaga agatcctttg    1740
atcttttcta cggggtctga cgctcagtgg aacgaaaact cacgttaagg attttggtc    1800 atgagattat caaaaaggat cttcacctag atccttttaa attaaaaatg aagttttaaa    1860
tcaatctaaa gtatatatga gtaaacttgg tctgacagtt accaatgctt aatcagtgag    1920
gcacctatct cagcgatctg tctatttcgt tcatccatag ttgcctgact ccccgtcgtg    1980
tagataacta cgatacggga gggcttacca tctggcccca gtgctgcaat gataccgcga    2040
gacccacgct caccggctcc agatttatca gcaataaacc agccagccgg aagggccgag    2100
cgcagaagtg gtcctgcaac tttatccgcc tccatccagt ctattaattg ttgccgggaa    2160
gctagagtaa gtagttcgcc agttaatagt ttgcgcaacg ttgttgccat tgctacaggc    2220
atcgtggtgt cacgctcgtc gtttggtatg gcttcattca gctccggttc caacgatca    2280 aggcgagtta catgatcccc catgttgtgc aaaaaagcgg ttagctcctt cggtcctccg    2340
atcgttgtca gaagtaagtt ggccgcagtg ttatcactca tggttatggc agcactgcat    2400
aattctctta ctgtcatgcc atccgtaaga tgcttttctg tgactggtga gtactcaacc    2460
aagtcattct gagaatagtg tatgcggcga ccgagttgct cttgcccggc gtcaatacgg    2520
gataataccg cgccacatag cagaacttta aaagtgctca tcattggaaa acgttcttcg    2580
gggcgaaaac tctcaaggat cttaccgctg ttgagatcca gttcgatgta acccactcgt    2640
gcacccaact gatcttcagc atcttttact ttcaccagcg tttctgggtg agcaaaaaca    2700
ggaaggcaaa atgccgcaaa aaagggaata agggcgacac ggaaatgttg aatactcata    2760
ctcttccttt ttcaatatta ttgaagcatt tatcagggtt attgtctcat gagcggatac    2820
atatttgaat gtatttagaa aaataaacaa ataggggttc cgcgcacatt tccccgaaaa    2880
```

```
gtgccacctg acgtctaaga aaccattatt atcatgacat taacctataa aaataggcgt   2940
atcacgaggc cctttcgtct cgcgcgtttc ggtgatgacg gtgaaaacct ctgacacatg   3000
cagctcccgg agacggtcac agcttgtctg taagcggatg ccgggagcag acaagcccgt   3060
cagggcgcgt cagcgggtgt tggcgggtgt cggggctggc ttaactatgc ggcatcagag   3120
cagattgtac tgagagtgca ccatatgcgg tgtgaaatac cgcacagatg cgtaaggaga   3180
aaataccgca tcaggcgcca ttcgccattc aggctgcgca actgttggga agggcgatcg   3240
gtgcgggcct cttcgctatt acgccagctg gcgaaagggg gatgtgctgc aaggcgatta   3300
agttgggtaa cgccagggtt ttcccagtca cgacgttgta aaacgacggc cagtgaattc   3360
gagctcggta ccctacagtt gaagtcggaa gtttacatac acttaagttg gagtcattaa   3420
aactcgtttt tcaactactc cacaaatttc ttgttaacaa acaatagttt tggcaagtca   3480
gttaggacat ctactttgtg catgacacaa gtcattttc caacaattgt ttacagacag   3540
attatttcac ttataattca ctgtatcaca attccagtgg gtcagaagtt tacatacact   3600
aagttgactg tgcctttaaa cagcttggaa aattccagaa aatgatgtca tggctttaga   3660
agcttctgat agactaattg acatcatttg agtcaattgg aggtgtacct gtggatgtat   3720
ttcaagggaa ttctgtggaa tgtgtgtcag ttagggtgtg gaaagtcccc aggctcccca   3780
ggcaggcaga agtatgcaaa gcatgcatat cgataagctt gatatcgaat taggaggaaa   3840
aactgtttca tacagaaggc gtcaattagg aggaaaaact gtttcataca gaaggcgtca   3900
attaggagga aaaactgttt catacagaag gcgtcaattg gtcccatcga attaggagga   3960
aaaactgttt catacagaag gcgtcaatta ggaggaaaaa ctgtttcata cagaaggcgt   4020
caattaggag gaaaaactgt ttcatacaga aggcgtcaat tggtcccggg acattttgac   4080 accccccataa tattttttcca gaattaacag tataaattgc atctcttgtt caagagttcc   4140
ctatcactct ctttaatcac tactcacagt aacctcaact cctgaattcc atggccatgt   4200
gtcatcagca gctggtcatc agctggttca gcctggtgtt cctggccagc cccctggtgg   4260
ccatctggga gctgaagaaa gacgtgtacg tggtggagct ggactggtat cccgacgccc   4320
ctggcgagat ggtggtgctg acctgcgaca ccccgaagaa ggacggcatc acctggaccc   4380
tggaccagag cagcgaggtg ctgggcagcg gcaagaccct gaccatccag gtcaaagagt   4440
tcggcgacgc cggccagtac acctgccaca agggcggcga agtgctgtcc cacagcctgc   4500
tgctgctgca caagaaagag gatggcatct ggtccaccga catcctgaag gaccagaaag   4560
agcccaagaa caagaccttc ctgcggtgcg aggccaagaa ctacagcggc cggttcacct   4620
gttggtggct gaccaccatc agcaccgacc tgaccttcag cgtgaagagc agccggggca   4680
gcagcgaccc tcagggcgtg acctgcggag ccgccaccct gagcgccgag agagtgcggg   4740
gcgacaacaa agagtacgag tacagcgtcg agtgccagga agatagcgcc tgccctgccg   4800
ccgaggaaag cctgcccatc gaggtgatgg tggacgccgt gcacaagctg aagtacgaga   4860
actacaccct cagcttttc atccgggaca tcatcaagcc cgaccccccc aagaacctgc   4920
agctgaagcc cctgaagaac agccggcagg tggaggtgtc ctgggagtac cctgacacct   4980
ggtccacccc ccacagctac ttcagcctga ccttctgtgt gcaggtgcag ggcaagagca   5040
agcgggagaa gaaagaccgg gtgttcaccg acaagaccag cgccaccgtg atctgccgga   5100
agaacgccag catcagcgtg cgggcccagg accggtacta cagcagctcc tggtccgagt   5160 gggcagcgt gccctgcagc ggcggagggg cggaggaag ccggaacctg cccgtggcta   5220
cccccgaccc cggcatgttc ccctgcctgc accacagcca gaacctgctg cgggccgtga   5280
```

| | |
|---|---|
| gcaacatgct gcagaaggcc cggcagaccc tggaattcta ccoctgcacc agcgaggaaa | 5340 |
| tcgaccacga ggacatcacc aaggataaga ccagcaccgt ggaggcctgc ctgccoctgg | 5400 |
| aactgaccaa gaacgagagc tgtctgaact ctcgggagac aagcttcatc accaacggct | 5460 |
| cttgcctggc cagcagaaag accagcttca tgatggccct gtgcctgagc agcatctacg | 5520 |
| aggacctgaa gatgtaccag gtggagttca gaccatgaa cgccaagctg ctgatggacc | 5580 |
| ccaagcggca gatcttcctg gatcagaaca tgctggccgt gatcgacgag ctgatgcagg | 5640 |
| ccctgaactt caacagcgag acagtgcccc agaagtccag cctggaagag cccgacttct | 5700 |
| acaagaccaa gatcaagctg tgcatcctcc tgcatgcctt ccggatccgg gccgtgacca | 5760 |
| tcgaccgggt gatgagctac ctgaacgcca gctgatgagc | 5800 |

<210> SEQ ID NO 9
<211> LENGTH: 1851
<212> TYPE: DNA
<213> ORGANISM: Homo sapiens

<400> SEQUENCE: 9

| | |
|---|---|
| atgaaatcct tgagtgtttc cctagtggtc ctgtggctcc agttaaactg ggtgaacagc | 60 |
| cagcagaagg tgcagcagag cccagaatcc ctcattgtcc cagagggagc catgacctct | 120 |
| ctcaactgca ctttcagcga cagtgcttct cagtattttg catggtacag acagcattct | 180 |
| gggaaagccc ccaaggcact gatgtccatc ttctccaatg gtgaaaaaga agaaggcaga | 240 |
| ttcacaattc acctcaataa agccagtctg catttctcgc tacacatcag agactcccag | 300 |
| cccagtgact ctgctctcta cctctgtgca gccaataact atgcccaggg attaaccttc | 360 |
| ggtcttggca ccagagtatc tgtgtttccc tacatccaga acccagaacc tgctgtgtac | 420 |
| cagttaaaag atcctcggtc tcaggacagc accctctgcc tgttcaccga ctttgactcc | 480 |
| caaatcaatg tgccgaaaac catggaatct ggaacgttca cactgacaa actgtgctg | 540 |
| gacatgaaag ctatggatc caagagcaat ggggccattg cctggagcaa ccagacaagc | 600 |
| ttcacctgcc aagatatctt caagagacc aacgccacct accccagttc agacgttccc | 660 |
| tgtgatgcca cgttgactga gaaaagcttt gaaacagata tgaacctaaa ctttcaaaac | 720 |
| ctgtcagtta tgggactccg aatcctcctg ctgaaagtag ccggatttaa cctgctcatg | 780 |
| acgctgaggc tgtggtccag tcgtgccaag cgaggtaagc ctatccctaa ccctctcctc | 840 |
| ggtctcgatt ctacgtccgg aagcggagcc cctgtaaagc agactttgaa ttttgacctt | 900 |
| ctcaagttgg cgggagacgt cgagtccaac cctgggccca tgggctccag actcttcttt | 960 |
| gtggttttga ttctcctgtg tgcaaaacac atggaggctg cagtcaccca agtccaaga | 1020 |
| agcaaggtgg cagtaacagg aggaaaggtg acattgagct gtcaccagac taataaccat | 1080 |
| gactatatgt actggtatcg gcaggacacg gggcatgggc tgaggctgat ccattactca | 1140 |
| tatgtcgctg acagcacgga gaaggagat atccctgatg gtacaaggc ctccagacca | 1200 |
| agccaagaga atttctctct cattctggag ttggcttccc tttctcagac agctgtatat | 1260 |
| ttctgtgcca gcagccctgg ggggggggg gaacagtact cggtcccgg caccaggctc | 1320 |
| acggttttag aggatctgag aaatgtgact ccacccaagg tctccttgtt tgagccatca | 1380 |
| aaagcagaga ttgcaaacaa cgaaaggct accctcgtgt gcttggccag ggcttcttc | 1440 |
| cctgaccacg tggagctgag ctggtgggtg aatggcaagg aggtccacag tggggtcagc | 1500 |
| acggaccctc aggcctacaa ggagagcaat tatagctact gcctgagcag ccgcctgagg | 1560 |
| gtctctgcta ccttctggca caatcctcga aaccacttcc gctgccaagt gcagttccat | 1620 |

```
gggctttcag aggaggacaa gtggccagag ggctcaccca aacctgtcac acagaacatc    1680
agtgcagagg cctggggccg agcagactgt gggattacct cagcatccta tcaacaaggg    1740
gtcttgtctg ccaccatcct ctatgagatc ctgctaggga agccacccct gtatgctgtg    1800
cttgtcagta cactggtggt gatggctatg gtcaaaagaa agaattcatg a             1851

<210> SEQ ID NO 10
<211> LENGTH: 2403
<212> TYPE: DNA
<213> ORGANISM: Homo sapiens

<400> SEQUENCE: 10
atgttgcttg aacatttatt aataatcttg tggatgcagc tgacatgggt cagtggtcaa     60
cagctgaatc agagtcctca atctatgttt atccaggaag agaagatgt ctccatgaac     120 tgcacttctt caagcatatt aacacctgg ctatggtaca agcaggaccc tggggaaggt     180
cctgtcctct tgatagcctt atataaggct ggtgaattga cctcaaatgg aagactgact     240
gctcagtttg gtataaccag aaaggacagc ttcctgaata tctcagcatc catacctagt     300
gatgtaggca tctacttctg tgctggtggg accggtaacc agttctattt ggggacaggg     360
acaagtttga cggtcattcc aaatatccag aaccctgacc ctgccgtgta ccagctgaga     420
gactctaaat ccagtgacaa gtctgtctgc ctattcaccg attttgattc tcaaacaaat     480
gtgtcacaaa gtaaggattc tgatgtgtat atcacagaca aaactgtgct agacatgagg     540
tctatggact tcaagagcaa cagtgctgtg gcctggagca caaatctga ctttgcatgt     600 gcaaacgcct tcaacaacag cattattcca gaagacacct tcttccccag cccagaaagt     660
tcctgtgatg tcaagctggt cgagaaaagc tttgaaacag atacgaacct aaactttcaa     720
aacctgtcag tgattgggtt ccgaatcctc ctcctgaagg tggccgggtt taatctgctc     780
atgacgctgc ggctgtggtc cagctgaact agaactagtg atctccacg tggcggctag     840 tactccggta ttgcggtacc cttgtacgcc tgttttatac tcccttcccg taacttagac     900
gcacaaaacc aagttcaata gaagggggta caaaccagta ccaccacgaa caagcacttc     960
tgtttccccg gtgatgtcgt atagactgct tgcgtggttg aaagcgacgg atccgttatc    1020
cgcttatgta cttcgagaag cccagtacca cctcggaatc ttcgatgcgt tgcgctcagc    1080
actcaacccc agagtgtagc ttaggctgat gagtctggac atccctcacc ggtgacggtg    1140
gtccaggctg cgttggcggc ctacctatgg ctaacgccat gggacgctag ttgtgaacaa    1200
ggtgtgaaga gccattgag ctacataaga atcctccggc ccctgaatgc ggctaatccc    1260
aacctcggag caggtggtca caaaccagtg attggcctgt cgtaacgcgc aagtccgtgg    1320
cggaaccgac tactttgggt gtccgtgttt cctttatttt tattgtggct gcttatggtg    1380
acaatcacag attgttatca taagcgaat tggataggat caagcttatc gataccgtcg    1440
acctcgagct caagcttcga attcgccctt cccatgggca caaggttgtt cttctatgtg    1500 gcccttgtc tcctgtggac aggacacatg gatgctggaa tcacccagag cccaagacac    1560
aaggtcacag agacaggaac accagtgact ctgagatgtc accagactga gaaccaccgc    1620
tatatgtact ggtatcgaca gacccgggg catgggctga ggctgatcca ttactcatat    1680
ggtgttaaag atactgacaa aggagaagtc tcagatggct atagtgtctc tagatcaaag    1740
acagaggatt tcctcctcac tctggagtcc gctaccagct cccagacatc tgtgtacttc    1800
tgtgccatca gtgaggtagg ggttgggcag ccccagcatt tggtgatgg gactcgactc    1860 tccatcctag aggacctgaa caaggtgttc ccaccccgagg tcgctgtgtt tgagccatca    1920
```

| | |
|---|---|
| gaagcagaga tctcccacac ccaaaaggcc acactggtgt gcctggccac aggcttcttc | 1980 |
| cctgaccacg tggagctgag ctggtgggtg aatgggaagg aggtgcacag tggggtcagc | 2040 |
| acggacccgc agcccctcaa ggagcagccc gccctcaatg actccagata ctgcctgagc | 2100 |
| agccgcctga gggtctcggc caccttctgg cagaaccccc gcaaccactt ccgctgtcaa | 2160 |
| gtccagttct acgggctctc ggagaatgac gagtggaccc aggatagggc caaacccgtc | 2220 |
| acccagatcg tcagcgccga ggcctggggt agagcagact gtggctttac ctcggtgtcc | 2280 |
| taccagcaag gggtcctgtc tgccaccatc ctctatgaga tcctgctagg gaaggccacc | 2340 |
| ctgtatgctg tgctggtcag cgcccttgtg ttgatggcca tggtcaagag aaaggatttc | 2400 |
| tga | 2403 |

<210> SEQ ID NO 11
<211> LENGTH: 6735
<212> TYPE: DNA
<213> ORGANISM: Artificial Sequence
<220> FEATURE:
<223> OTHER INFORMATION: Synthetic

<400> SEQUENCE: 11

| | |
|---|---|
| tcgacggatc ccccgggctg caggaattcg agcatcttac cgccatttat acccatattt | 60 |
| gttctgtttt tcttgatttg ggtatacatt taaatgttaa taaaacaaaa tggtggggca | 120 |
| atcatttaca ttttagggat atgtaattac tagttcaggt gtattgccaa caagacaaac | 180 |
| atgttaagaa actttcccgt tatttacgct ctgttcctgt taatcaacct ctggattaca | 240 |
| aaatttgtga agattgacta gatattctta actatgttgc tccttttacg ctgtgtggat | 300 |
| atgctgcttt aatgcctctg tatcatgcta ttgcttcccg tacggctttc gttttctcct | 360 |
| ccttgtataa atcctggttg ctgtctcttt atgaggagtt gtggcccgtt gtccgtcaac | 420 |
| gtggcgtggt gtgctctgtg tttgctgacg caaccccac tggctgggc attgccacca | 480 |
| cctgtcaact cctttctggg actttcgctt tcccctcc gatcgccacg gcagaactca | 540 |
| tcgccgcctg ccttgcccgc tgctggacag gggctaggt gctgggcact gataattccg | 600 |
| tggtgttgtc ggggaagctg acgtcctttc gaattcgata tcaagcttaa cacgagccat | 660 |
| agatagaata aaagatttta tttagtctcc agaaaaggg gggaatgaaa gaccccaccg | 720 |
| ctagcgatat cgaattcaca acccctcact cggcgcgcca gtcctccgac agactgagtc | 780 |
| gcccgggtac ccgtgttctc aataaaccct cttgcagttg catccgactc gtggtctcgc | 840 |
| tgttccttgg gagggtctcc tctgagtgat tgactgccca cctcgggggt ctttcattct | 900 |
| cgagagcttt ggcgtaatca tggtcatagc tgtttcctgt gtgaaattgt tatccgctca | 960 |
| caattccaca acatacga gccggaagca taaagtgtaa agcctgggt gcctaatgag | 1020 |
| tgagctaact cacattaatt gcgttgcgct cactgcccgc tttccagtcg ggaaacctgt | 1080 |
| cgtgccagct gcattaatga atcggccaac gcgcgggag aggcggtttg cgtattgggc | 1140 |
| gctcttccgc ttcctcgctc actgactcgc tgcgctcggt cgttcggctg cggcgagcgg | 1200 |
| tatcagctca ctcaaaggcg gtaatacggt tatccacaga atcaggggat aacgcaggaa | 1260 |
| agaacatgtg agcaaaaggc cagcaaaagg ccaggaaccg taaaaaggcc gcgttgctgg | 1320 |
| cgttttccca taggctccgc cccctgacg agcatcacaa aaatcgacgc tcaagtcaga | 1380 |
| ggtggcgaaa cccgacagga ctataaagat accaggcgtt cccccctgga agctccctcg | 1440 |
| tgcgctctcc tgttccgacc ctgccgctta ccggatacct gtccgccttt ctcccttcgg | 1500 |
| gaagcgtggc gctttctcaa tgctcacgct gtaggtatct cagttcggtg taggtcgttc | 1560 |

```
gctccaagct gggctgtgtg cacgaacccc ccgttcagcc cgaccgctgc gccttatccg   1620
gtaactatcg tcttgagtcc aacccggtaa gacacgactt atcgccactg gcagcagcca   1680
ctggtaacag gattagcaga gcgaggtatg taggcggtgc tacagagttc ttgaagtggt   1740
ggcctaacta cggctacact agaaggacag tatttggtat ctgcgctctg ctgaagccag   1800
ttaccttcgg aaaagagtt ggtagctctt gatccggcaa acaaaccacc gctggtagcg   1860
gtggtttttt tgtttgcaag cagcagatta cgcgcagaaa aaaggatct caagaagatc   1920 ctttgatctt ttctacgggg tctgacgctc agtggaacga aaactcacgt taagggattt   1980
tggtcatgag attatcaaaa aggatcttca cctagatcct tttaaattaa aaatgaagtt   2040
ttaaatcaat ctaaagtata tatgagtaaa cttggtctga cagttaccaa tgcttaatca   2100
gtgaggcacc tatctcagcg atctgtctat ttcgttcatc catagttgcc tgactcccccg   2160 tcgtgtagat aactacgata cgggagggct taccatctgg ccccagtgct gcaatgatac   2220
cgcgagaccc acgctcaccg gctccagatt tatcagcaat aaaccagcca gccggaaggg   2280
ccgagcgcag aagtggtcct gcaactttat ccgcctccat ccagtctatt aattgttgcc   2340
gggaagctag agtaagtagt tcgccagtta atagtttgcg caacgttgtt gccattgctg   2400
ctggcatcgt ggtgtcacgc tcgtcgtttg gtatggcttc attcagctcc ggttcccaac   2460
gatcaaggcg agtacatga tcccccatgt tgtgcaaaaa agcggttagc tccttcggtc   2520
ctccgatcgt tgtcagaagt aagttggccg cagtgttatc actcatggtt atggcagcac   2580
tgcataattc tcttactgtc atgccatccg taagatgctt ttctgtgact ggtgagtact   2640
caaccaagtc attctgagaa tagtgtatgc ggcgaccgag ttgctcttgc ccggcgtcaa   2700
tacgggataa taccgcgcca catagcagaa ctttaaaagt gctcatcatt ggaaaacgtt   2760
cttcggggcg aaaactctca aggatcttac cgctgttgag atccagttcg atgtaaccca   2820
ctcgtgcacc caactgatct tcagcatctt ttactttcac cagcgtttct gggtgagcaa   2880
aaacaggaag gcaaaatgcc gcaaaaaagg gaataagggc gacacggaaa tgttgaatac   2940
tcatactctt ccttttttcaa tattattgaa gcatttatca gggttattgt ctcatgagcg   3000
gatacatatt tgaatgtatt tagaaaaata aacaaatagg ggttccgcgc acatttcccc   3060
gaaaagtgcc acctgacgtc taagaaacca ttattatcat gacattaacc tataaaaata   3120
ggcgtatcac gaggcccttt cgtcttcaag ctgcctcgcg cgtttcggtg atgacggtga   3180
aaacctctga cacatgcagc tcccggagac ggtcacagct tgtctgtaag cggatgccgg   3240
gagcagacaa gcccgtcagg gcgcgtcagc gggtgttggc gggtgtcggg gcgcagccat   3300
gacccagtca cgtagcgata gttactatgc ggcatcagag cagattgtac tgagagtgca   3360
ccatatgcgg tgtgaaatac cgcacagatg cgtaaggaga aaataccgca tcaggcgcca   3420
ttcgccattc aggctgcgca actgttggga agggcgatcg gtgcgggcct cttcgctatt   3480
acgccagctg gcgaaagggg gatgtgctgc aaggcgatta agttgggtaa cgccagggtt   3540
ttcccagtca cgacgttgta aaacgacggc cagtgaatta gtactctagc ttaagacgcg   3600
tggcctgaaa taacctctga agaggaact tggttaggta ccttctgagg cggaaagaac   3660
cagctgtgga atgtgtgtca gttagggtgt ggaaagtccc caggctcccc agcaggcaga   3720
agtatgcaaa gcatgcatct caattagtca gcaaccaggt gtggaaagtc ccaggctcc   3780 ccagcaggca gaagtatgca aagcatgcat ctcaattagt cagcaaccat agtcccttaa   3840
gaatgtagtc ttatgcaata ctcttgtagt cttgcaacat ggtaacgatg agttagcaac   3900
atgccttaca aggagagaaa aagcaccgtg catgccgatt ggtggaagta aggtggtacg   3960
```

```
atcgtgcctt attaggaagg caacagacgg gtctgacatg gattggacga accactgaat    4020
tgccgcattg cagagatatt gtatttaagt gcctagctcg atacaataaa cgcgccagtc    4080
ctccgattga ctgcgtcgcc cgggtacccg tattcccaat aaagcctctt gctgtttgca    4140
tccgaatcgt ggactcgctg atccttggga gggtctcctc agattgattg actgcccacc    4200 tcggggtct ttcatttgga ggttccaccg agatttggag acccctgccc agggaccacc     4260 gaccccccg ccgggaggta agctggccag cggtcgtttc gtgtctgtct ctgtctttgg     4320
gcgtgtttgt gccggcatct agtgtttgcg cctgcgtctg tactagttgg ctaactagat    4380
ctgtatctgg cggtcccgcg aagaactga cgagttcgta ttcccggccg cagcccctgg     4440
gagacgtccc agcggcctcg ggggcccgtt ttgtggccca ttctgtatca gttaacctac    4500
ccgagtcgga ctttttggag ctccgccact gtccgagggg tacgtggctt tgttggggga    4560
cgagagacag agacacttcc cgcccccgtc tgaattttg ctttcggttt tacgccgaaa     4620
ccgcgccgcg cgtcttgtct gctgcagcat cgttctgtgt tgtctctgtc tgacgtggtt    4680
ctgtattgtc tgaaaatagt cgaggtcgac ggtatcgata agcttgatat cgaattagga    4740
ggaaaaactg tttcatacag aaggcgtcaa ttaggaggaa aaactgtttc atacagaagg    4800
cgtcaattag gaggaaaaac tgtttcatac agaaggcgtc aattggtccc atcgaattag    4860
gaggaaaaac tgtttcatac agaaggcgtc aattaggagg aaaaactgtt tcatacagaa    4920
ggcgtcaatt aggaggaaaa actgtttcat acagaaggcg tcaattggtc ccgggacatt    4980
ttgacccccc cataatattt ttccagaatt aacagtataa attgcatctc ttgttcaaga    5040
gttccctatc actctcttta atcactactc acagtaacct caactcctga attcatgtgt    5100
cctcagaagc taaccatctc ctggtttgcc atcgttttgc tggtgtctcc actcatggcc    5160
atgtgggagc tggagaaaga cgtttatgtt gtagaggtgg actggactcc cgatgcccct    5220
ggagaaacag tgaacctcac ctgtgacacg cctgaagaag atgacatcac ctggaccta    5280 gaccagagac atggagtcat aggctctgga aagaccctga ccatcactgt caaagagttt    5340
ctagatgctg gccagtacac ctgccacaaa ggaggcgaga ctctgagcca ctcacatctg    5400
ctgctccaca agaaggaaaa tggaatttgg tccactgaaa ttttaaaaaa tttcaaaaac    5460
aagactttcc tgaagtgtga agcaccaaat tactccggac ggttcacgtg ctcatggctg    5520
gtgcaaagaa acatggactt gaagttcaac atcaagagca gtagcagttc ccctgactct    5580
cgggcagtga cctgtggaat ggcgtctctg tctgcagaga aggtcacact ggaccaaagg    5640
gactatgaga agtattcagt gtcctgccag gaggatgtca cctgcccaac tgccgaggag    5700
accctgccca ttgaactggc gttggaagca cggcagcaga ataaatatga aactacagc     5760 accagcttct tcatcaggga catcatcaaa ccagaccccg ccaagaactt gcagatgaag    5820
cctttgaaga actcacaggt ggaggtcagc tgggagtacc ctgactcctg gagcactccc    5880
cattcctact tctccctcaa gttctttgtt cgaatccagc gcaagaaaga aagatgaag     5940 gagacagagg aggggtgtaa ccagaaaggt gcgttcctcg tagagaagac atctaccgaa    6000
gtccaatgca aaggcgggaa tgtctgcgtg caagctcagg atcgctatta caattcctcg    6060
tgcagcaagt gggcatgtgt tcctgcagg gtccgatccg gtggcggtgg ctcgggcggt     6120
ggtgggtcgg gtggcggcgg atctagggtc attccagtct ctggacctgc caggtgtctt    6180
agccagtccc gaaacctgct gaagaccaca gatgacatgg tgaagacggc cagagaaaaa    6240
ctgaaacatt attcctgcac tgctgaagac atcgatcatg aagacatcac acgggaccaa    6300
accagcacat tgaagacctg tttaccactg gaactacaca gaacgagag ttgcctggct      6360
```

-continued

| | |
|---|---|
| actagagaga cttcttccac aacaagaggg agctgcctgc ccccacagaa gacgtctttg | 6420 |
| atgatgaccc tgtgccttgg tagcatctat gaggacttga agatgtacca gacagagttc | 6480 |
| caggccatca acgcagcact tcagaatcac aaccatcagc agatcattct agacaagggc | 6540 |
| atgctggtgg ccatcgatga gctgatgcag tctctgaatc ataatggcga gactctgcgc | 6600 |
| cagaaacctc ctgtgggaga agcagaccct tacagagtga aaatgaagct ctgcatcctg | 6660 |
| cttcacgcct tcagcacccg cgtcgtgacc atcaacaggg tgatgggcta tctgagctcc | 6720 |
| gcctgagcgg ccgcg | 6735 |

<210> SEQ ID NO 12
<211> LENGTH: 5230
<212> TYPE: DNA
<213> ORGANISM: Artificial Sequence
<220> FEATURE:
<223> OTHER INFORMATION: Synthetic

<400> SEQUENCE: 12

| | |
|---|---|
| gatcctcaca caaaaaacca acacacagat gtaatgaaaa taaagatatt ttattgcggc | 60 |
| cgctttactt gtacagctcg tccatgccga gagtgatccc ggcggcggtc acgaactcca | 120 |
| gcaggaccat gtgatcgcgc ttctcgttgg ggtctttgct cagggcggac tgggtgctca | 180 |
| ggtagtggtt gtcgggcagc agcacggggc cgtcgccgat gggggtgttc tgctggtagt | 240 |
| ggtcggcgag ctgcacgctg ccgtcctcga tgttgtggcg gatcttgaag ttcaccttga | 300 |
| tgccgttctt ctgcttgtcg gccatgatat agacgttgtg gctgttgtag ttgtactcca | 360 |
| gcttgtgccc caggatgttg ccgtcctcct tgaagtcgat gcccttcagc tcgatgcggt | 420 |
| tcaccagggt gtcgccctcg aacttcacct cggcgcgggt cttgtagttg ccgtcgtcct | 480 |
| tgaagaagat ggtgcgctcc tggacgtagc cttcgggcat ggcggacttg aagaagtcgt | 540 |
| gctgcttcat gtggtcgggg tagcggctga agcactgcac gccgtaggtc agggtggtca | 600 |
| cgagggtggg ccagggcacg ggcagcttgc cggtggtgca gatgaacttc agggtcagct | 660 |
| tgccgtaggt ggcatcgccc tcgccctcgc cggacacgct gaacttgtgg ccgtttacgt | 720 |
| cgccgtccag ctcgaccagg atgggcacca ccccggtgaa cagctcctcg cccttgctca | 780 |
| ccatggaatt caggagttga ggttactgtg agtagtgatt aaagagagtg atagggaact | 840 |
| cttgaacaag agatgcaatt tatactgtta attctggaaa aatattatgg gggtgtcaaa | 900 |
| atgtcccggg accaattgac gccttctgta tgaaacagtt tttcctccta attgacgcct | 960 |
| tctgtatgaa acagtttttc ctcctaattg acgccttctg tatgaaacag ttttttcctcc | 1020 |
| taattcgatg ggaccaattg acgccttctg tatgaaacag ttttttcctcc taattgacgc | 1080 |
| cttctgtatg aaacagtttt tcctcctaat tgacgccttc tgtatgaaac agttttttcct | 1140 |
| cctaattcga tatcaagctt aacacgagcc atagatagaa taaagatttt tatttagtct | 1200 |
| ccagaaaaag gggggaatga agaccccac cgctagcgat atcgaattca caacccctca | 1260 |
| ctcggcgcgc cagtcctccg acagactgag tcgcccgggt accgtgttc tcaataaacc | 1320 |
| ctcttgcagt tgcatccgac tcgtggtctc gctgttcctt ggagggtct cctctgagtg | 1380 |
| attgactgcc cacctcgggg gtctttcatt ctcgagagct ttggcgtaat catggtcata | 1440 |
| gctgtttcct gtgtgaaatt gttatccgct cacaattcca cacaacatac gagccggaag | 1500 |
| cataaagtgt aaagcctggg gtgcctaatg agtgagctaa ctcacattaa ttgcgttgcg | 1560 |
| ctcactgccc gctttccagt cgggaaacct gtcgtgccag ctgcattaat gaatcggcca | 1620 |
| acgcgcgggg agaggcggtt tgcgtattgg gcgctcttcc gcttcctcgc tcactgactc | 1680 |

```
gctgcgctcg tcgttcggc tgcggcgagc ggtatcagct cactcaaagg cggtaatacg    1740
gttatccaca gaatcagggg ataacgcagg aaagaacatg tgagcaaaag gccagcaaaa    1800
ggccaggaac cgtaaaaagg ccgcgttgct ggcgtttttc cataggctcc gcccccctga    1860
cgagcatcac aaaaatcgac gctcaagtca gaggtggcga acccgacag  gactataaag    1920 ataccaggcg tttccccctg gaagctccct cgtgcgctct cctgttccga ccctgccgct    1980
taccggatac ctgtccgcct ttctcccttc gggaagcgtg gcgctttctc aatgctcacg    2040
ctgtaggtat ctcagttcgg tgtaggtcgt tcgctccaag ctgggctgtg tgcacgaacc    2100
ccccgttcag cccgaccgct gcgccttatc cggtaactat cgtcttgagt ccaacccggt    2160
aagacacgac ttatcgccac tggcagcagc cactggtaac aggattagca gagcgaggta    2220
tgtaggcggt gctacagagt tcttgaagtg gtggcctaac tacggctaca ctagaaggac    2280
agtatttggt atctgcgctc tgctgaagcc agttaccttc ggaaaaagag ttggtagctc    2340
ttgatccggc aaacaaacca ccgctggtag cggtggtttt tttgtttgca agcagcagat    2400
tacgcgcaga aaaaaggat  ctcaagaaga tcctttgatc ttttctacgg gtctgacgc    2460 tcagtggaac gaaaactcac gttaagggat tttggtcatg agattatcaa aaaggatctt    2520
cacctagatc cttttaaatt aaaaatgaag ttttaaatca atctaaagta tatatgagta    2580
aacttggtct gacagttacc aatgcttaat cagtgaggca cctatctcag cgatctgtct    2640
atttcgttca tccatagttg cctgactccc cgtcgtgtag ataactacga tacgggaggg    2700
cttaccatct ggccccagtg ctgcaatgat accgcgagac ccacgctcac cggctccaga    2760
tttatcagca ataaaccagc cagccggaag ggccgagcgc agaagtggtc ctgcaacttt    2820
atccgcctcc atccagtcta ttaattgttg ccgggaagct agagtaagta gttcgccagt    2880
taatagtttg cgcaacgttg ttgccattgc tgctggcatc gtggtgtcac gctcgtcgtt    2940
tggtatggct tcattcagct ccggttccca acgatcaagg cgagttacat gatccccat    3000 gttgtgcaaa aaagcggtta gctccttcgg tcctccgatc gttgtcagaa gtaagttggc    3060
cgcagtgtta tcactcatgg ttatggcagc actgcataat tctcttactg tcatgccatc    3120
cgtaagatgc ttttctgtga ctggtgagta ctcaaccaag tcattctgag aatagtgtat    3180
gcggcgaccg agttgctctt gcccggcgtc aatacgggat aataccgcgc cacatagcag    3240
aactttaaaa gtgctcatca ttggaaaacg ttcttcgggg cgaaaactct caaggatctt    3300
accgctgttg agatccagtt cgatgtaacc cactcgtgca cccaactgat cttcagcatc    3360
ttttactttc accagcgttt ctgggtgagc aaaaacagga aggcaaaatg ccgcaaaaaa    3420
gggaataagg gcgacacgga aatgttgaat actcatactc ttcctttttc aatattattg    3480
aagcatttat cagggttatt gtctcatgag cggatacata tttgaatgta tttagaaaaa    3540
taaacaaata ggggttccgc gcacatttcc ccgaaaagtg ccacctgacg tctaagaaac    3600
cattattatc atgacattaa cctataaaaa taggcgtatc acgaggccct ttcgtcttca    3660
agctgcctcg cgcgtttcgg tgatgacggt gaaaacctct gacacatgca gctcccggag    3720
acggtcacag cttgtctgta agcggatgcc gggagcagac aagcccgtca gggcgcgtca    3780
gcgggtgttg gcgggtgtcg gggcgcagcc atgacccagt cacgtagcga tagttactat    3840
gcggcatcag agcagattgt actgagagtg caccatatgc ggtgtgaaat accgcacaga    3900
tgcgtaagga gaaaataccg catcaggcgc cattcgccat tcaggctgcg caactgttgg    3960
gaagggcgat cggtgcgggc ctcttcgcta ttacgccagc tggcgaaagg gggatgtgct    4020
gcaaggcgat taagttgggt aacgccaggg ttttcccagt cacgacgttg taaaacgacg    4080
```

| | |
|---|---|
| gccagtgaat tagtactcta gcttaagacg cgtggcctga aataacctct gaaagaggaa | 4140 |
| cttggttagg taccttctga ggcggaaaga accagctgtg gaatgtgtgt cagttagggt | 4200 |
| gtggaaagtc cccaggctcc ccagcaggca gaagtatgca aagcatgcat ctcaattagt | 4260 |
| cagcaaccag gtgtggaaag tccccaggct ccccagcagg cagaagtatg caaagcatgc | 4320 |
| atctcaatta gtcagcaacc atagtccctt aagaatgtag tcttatgcaa tactcttgta | 4380 |
| gtcttgcaac atggtaacga tgagttagca acatgcctta caggagagag aaaagcaccg | 4440 |
| tgcatgccga ttggtggaag taaggtggta cgatcgtgcc ttattaggaa ggcaacagac | 4500 |
| gggtctgaca tggattggac gaaccactga attgccgcat tgcagagata ttgtatttaa | 4560 |
| gtgcctagct cgatacaata aacgcgccag tcctccgatt gactgcgtcg cccgggtacc | 4620 |
| cgtattccca ataaagcctc ttgctgtttg catccgaatc gtggactcgc tgatccttgg | 4680 |
| gagggtctcc tcagattgat tgactgccca cctcgggggt cttttcatttg gaggttccac | 4740 |
| cgagatttgg agaccccctgc ccagggacca ccgaccccc cgccgggagg taagctggcc | 4800 |
| agcggtcgtt tcgtgtctgt ctctgtcttt gggcgtgttt gtgccggcat ctagtgtttg | 4860 |
| cgcctgcgtc tgtactagtt ggctaactag atctgtatct ggcggtcccg cggaagaact | 4920 |
| gacgagttcg tattcccggc cgcagcccct gggagacgtc ccagcggcct cgggggcccg | 4980 |
| ttttgtggcc cattctgtat cagttaacct acccgagtcg acttttttgg agctccgcca | 5040 |
| ctgtccgagg ggtacgtggc tttgttgggg gacgagagac agagacactt cccgcccccg | 5100 |
| tctgaattt tgctttcggt tttacgccga aaccgcgccg cgcgtcttgt ctgctgcagc | 5160 |
| atcgttctgt gttgtctctg tctgacgtgg ttctgtattg tctgaaaata gtcgaggata | 5220 |
| tccccacgtg | 5230 |

<210> SEQ ID NO 13
<211> LENGTH: 1776
<212> TYPE: DNA
<213> ORGANISM: Artificial Sequence
<220> FEATURE:
<223> OTHER INFORMATION: Synthetic

<400> SEQUENCE: 13

| | |
|---|---|
| atgatgaaat ccttgagagt tttactagtg atcctgtggc ttcagttgag ctgggtttgg | 60 |
| agccaacaga aggaggtgga gcagaattct ggacccctca gtgttccaga gggagccatt | 120 |
| gcctctctca actgcactta cagtgaccga ggttcccagt ccttcttctg gtacagacaa | 180 |
| tattctggga aaagccctga gttgataatg ttcatatact ccaatggtga caaagaagat | 240 |
| ggaaggttta cagcacagct caataaagcc agccagtatg tttctctgct catcagagac | 300 |
| tcccagccca gtgattcagc cacctacctc tgtgccgtga acttcggagg aggaaagctt | 360 |
| atcttcggac agggaacgga gttatctgtg aaacccaata tccagaaccc agaacctgct | 420 |
| gtgtaccagt taaagatcc tcggtctcag acagcaccc tctgcctgtt caccgacttt | 480 |
| gactcccaaa tcaatgtgcc gaaaaccatg gaatctggaa cgttcatcac tgacaaaact | 540 |
| gtgctggaca tgaaagctat ggattccaag agcaatgggg ccattgcctg gagcaaccag | 600 |
| acaagcttca cctgccaaga tatcttcaaa gagaccaacg ccacctaccc cagttcagac | 660 |
| gttccctgtg atgccacgtt gactgagaaa agctttgaaa cagatatgaa cctaaacttt | 720 |
| caaaacctgt cagttatggg actccgaatc ctcctgctga aagtagccgg atttaacctg | 780 |
| ctcatgacgc tgaggctgtg gtccagtgag ggcagaggaa gtcttctaac atgcggtgac | 840 |
| gtggaggaga atcccggccc tatgagaatc aggctcctgt gctgtgtggc ctttctctc | 900 |

| | |
|---|---|
| ctgtgggcag gtccagtgat tgctgggatc acccaggcac caacatctca gatcctggca | 960 |
| gcaggacggc gcatgacact gagatgtacc caggatatga gacataatgc catgtactgg | 1020 |
| tatagacaag atctaggact ggggctaagg ctcatccatt attcaaatac tgcaggtacc | 1080 |
| actggcaaag gagaagtccc tgatggttat agtgtctcca gagcaaacac agatgatttc | 1140 |
| cccctcacgt tggcgtctgc tgtaccctct cagacatctg tgtacttctg tgccagcagc | 1200 |
| ctaagtttcg gcactgaagc tttctttgga caaggcacca gactcacagt tgtagaggat | 1260 |
| ctgagaaatg tgactccacc caaggtctcc ttgtttgagc catcaaaagc agagattgca | 1320 |
| aacaaacaaa aggctaccct cgtgtgcttg gccaggggct tcttccctga ccacgtggag | 1380 |
| ctgagctggt gggtgaatgg caaggaggtc cacagtgggg tcagcacgga ccctcaggcc | 1440 |
| tacaaggaga gcaattatag ctactgcctg agcagccgcc tgagggtctc tgctaccttc | 1500 |
| tggcacaatc ctcgcaacca cttccgctgc caagtgcagt ccatgggct ttcagaggag | 1560 |
| gacaagtggc cagagggctc acccaaacct gtcacacaga acatcagtgc agaggcctgg | 1620 |
| ggccgagcag actgtgggat tacctcagca tcctatcaac aaggggtctt gtctgccacc | 1680 |
| atcctctatg agatcctgct agggaaagcc accctgtatg ctgtgcttgt cagtacactg | 1740 |
| gtggtgatgg ctatggtcaa agaaagaat tcatga | 1776 |

<210> SEQ ID NO 14
<211> LENGTH: 7636
<212> TYPE: DNA
<213> ORGANISM: Artificial Sequence
<220> FEATURE:
<223> OTHER INFORMATION: Synthetic

<400> SEQUENCE: 14

| | |
|---|---|
| ggccgctcat cagctggcgt tcaggtagct catcacccgg tcgatggtca cggcccggat | 60 |
| ccggaaggca tgcaggagga tgcacagctt gatcttggtc ttgtagaagt cgggctcttc | 120 |
| caggctggac ttctggggca ctgtctcgct gttgaagttc agggcctgca tcagctcgtc | 180 |
| gatcacggcc agcatgttct gatccaggaa gatctgccgc ttggggtcca tcagcagctt | 240 |
| ggcgttcatg gtcttgaact ccacctggta catcttcagg tcctcgtaga tgctgctcag | 300 |
| gcacagggcc atcatgaagc tggtcttcct gctggccagg caagagccgt tggtgatgaa | 360 |
| gcttgtctcc cgagagttca gacagctctc gttcttggtc agttccaggg gcaggcaggc | 420 |
| ctccacggtg ctggtcttat ccttggtgat gtcctcgtgg tcgatttcct cgctggtgca | 480 |
| ggggtagaat tccagggtct gccgggcctt ctgcagcatg ttgctcacgg cccgcagcag | 540 |
| gttctggctg tggtgcaggc aggggaacat gccggggtcg ggggtagcca cgggcaggtt | 600 |
| ccggcttcct ccgcccctc cgccgctgca gggcacgctg gcccactcgg accaggagct | 660 |
| gctgtagtac cggtcctggg cccgcacgct gatgctggcg ttcttccggc agatcacggt | 720 |
| ggcgctggtc ttgtcggtga acacccggtc tttcttctcc cgcttgctct tgccctgcac | 780 |
| ctgcacacag aaggtcaggc tgaagtagct gtgggggtg gaccaggtgt cagggtactc | 840 |
| ccaggacacc tccacctgcc ggctgttctt caggggcttc agctgcaggt tcttgggggg | 900 |
| gtcgggcttg atgatgtccc ggatgaaaaa gctggaggtg tagttctcgt acttcagctt | 960 |
| gtgcacggcg tccaccatca cctcgatggg caggctttcc tcggcggcag gcaggcgct | 1020 |
| atcttcctgg cactcgacgc tgtactcgta ctctttgttg tcgccccgca ctctctcggc | 1080 |
| gctcagggtg gcggctccgc aggtcacgcc ctgagggtcg ctgctgcccc ggctgctctt | 1140 |
| cacgctgaag gtcaggtcgg tgctgatggt ggtcagccac caacaggtga accggccgct | 1200 |

```
gtagttcttg gcctcgcacc gcaggaaggt cttgttcttg ggctcttcct ggtccttcag   1260
gatgtcggtg gaccagatgc catcctcttt cttgtgcagc agcagcaggc tgtgggacag   1320
cacttcgccg cccttgtggc aggtgtactg gccggcgtcg ccgaactctt tgacctggat   1380
ggtcagggtc ttgccgctgc ccagcacctc gctgctctgg tccagggtcc aggtgatgcc   1440
gtcctcttcg ggggtgtcgc aggtcagcac caccatctcg ccaggggcgt cgggatacca   1500
gtccagctcc accacgtaca cgtctttctt cagctcccag atggccacca ggggctggc   1560 caggaacacc aggctgaacc agctgatgac cagctgctga tgacacatgg ccatggaatt   1620
caggagttga ggttactgtg agtagtgatt aaagagagtg atagggaact cttgaacaag   1680
agatgcaatt tatactgtta attctggaaa aatattatgg gggtgtcaaa atgtcccggg   1740
accaattgac gccttctgta tgaaacagtt tttcctccta attgacgcct tctgtatgaa   1800 acagttttc ctcctaattg acgccttctg tatgaaacag ttttcctcc taattcgatg   1860 ggaccaattg acgccttctg tatgaaacag ttttcctcc taattgacgc cttctgtatg   1920
aaacagtttt tcctcctaat tgacgccttc tgtatgaaac agttttcct cctaattcga   1980 tatcaagctt cgaattctgc agtcgacggt accgcgggcc cgggatccga taaataaaa   2040 gatttatttt agtctccaga aaagggggg aatgaaagac cccacctgta ggtttggcaa   2100
gctagcttaa gtaacgccat tttgcaaggc atggaaaata cataactgag aatagagaag   2160
ttcagatcaa ggttaggaac agagagacag cagaatatgg gccaaacagg atatctgtgg   2220
taagcagttc ctgccccggc tcagggccaa gaacagatgg tccccagatg cggtcccgcc   2280
ctcagcagtt tctagagaac catcagatgt ttccagggtg ccccaaggac ctgaaatgac   2340
cctgtgcctt atttgaacta accaatcagt tcgcttctcg cttctgttcg cgcgcttctg   2400
ctccccgagc tcaataaaag agcccacaac ccctcactcg gcgcgccagt cctccgatag   2460
actgcgtcgc ccgggtaccc gtgtatccaa taaaccctct tgcagttgca tccgacttgt   2520
ggtctcgctg ttccttggga gggtctcctc tgagtgattg actaccccgtc agcggggtc   2580 tttcatgggt aacagtttct gaagttggaa gaacaacatt ctgagggtag gagtcgaata   2640
ttaagtaatc ctgactcaat tagccactgt tttgaatcca catactccaa tactcctgaa   2700
atccatcgat ggagttcatt atggacagcg cagaaagagc tggggagaat tgtgaaattg   2760
ttatccgctc acaattccac acaacatacg agccggaagc ataaagtgta aagcctgggg   2820
tgcctaatga gtgagctaac tcacattaat tgcgttgcgc tcactgcccg ctttccagtc   2880
gggaaacctg tcgtgccagc tgcattaatg aatcggccaa cgcgcgggga gaggcggttt   2940
gcgtattggg cgctcttccg cttcctcgct cactgactcg ctgcgctcgg tcgttcggct   3000
gcggcgagcg gtatcagctc actcaaaggc ggtaatacgg ttatccacag aatcaggga   3060 taacgcagga aagaacatgt gagcaaaagg ccagcaaaag gccaggaacc gtaaaaaggc   3120
cgcgttgctg gcgttttcc ataggctccg ccccctgac gagcatcaca aaaatcgacg   3180
ctcaagtcag aggtggcgaa acccgacagg actataaaga taccaggcgt ttccccctgg   3240
aagctccctc gtgcgctctc ctgttccgac cctgccgctt accggatacc tgtccgcctt   3300
tctcccttcg ggaagcgtgg cgctttctca tagctcacgc tgtaggtatc tcagttcggt   3360
gtaggtcgtt cgctccaagc tgggctgtgt gcacgaaccc ccgttcagc ccgaccgctg   3420 cgccttatcc ggtaactatc gtcttgagtc aacccggta agacacgact tatcgccact   3480
ggcagcagcc actggtaaca ggattagcag agcgaggtat gtaggcggtg ctacagagtt   3540
cttgaagtgg tggcctaact acggctacac tagaaggaca gtatttggta tctgcgctct   3600
```

```
gctgaagcca gttaccttcg gaaaaagagt tggtagctct tgatccggca aacaaaccac  3660
cgctggtagc ggtggttttt ttgtttgcaa gcagcagatt acgcgcagaa aaaaggatc   3720 tcaagaagat cctttgatct tttctacggg gtctgacgct cagtggaacg aaaactcacg  3780
ttaagggatt ttggtcatga gattatcaaa aaggatcttc acctagatcc ttttaaatta  3840
aaaatgaagt tttaaatcaa tctaaagtat atatgagtaa acttggtctg acagttacca  3900
atgcttaatc agtgaggcac ctatctcagc gatctgtcta tttcgttcat ccatagttgc  3960
ctgactcccc gtcgtgtaga taactacgat acgggagggc ttaccatctg gccccagtgc  4020
tgcaatgata ccgcgagacc cacgctcacc ggctccagat ttatcagcaa taaaccagcc  4080
agccggaagg gccgagcgca gaagtggtcc tgcaacttta tccgcctcca tccagtctat  4140
taattgttgc cgggaagcta gagtaagtag ttcgccagtt aatagtttgc gcaacgttgt  4200
tgccattgct acaggcatcg tggtgtcacg ctcgtcgttt ggtatggctt cattcagctc  4260
cggttcccaa cgatcaaggc gagttacatg atcccccatg ttgtgcaaaa aagcggttag  4320
ctccttcggt cctccgatcg ttgtcagaag taagttggcc gcagtgttat cactcatggt  4380
tatggcagca ctgcataatt ctcttactgt catgccatcc gtaagatgct tttctgtgac  4440
tggtgagtac tcaaccaagt cattctgaga atagtgtatg cggcgaccga gttgctcttg  4500
cccggcgtca atacgggata ataccgcgcc acatagcaga actttaaaag tgctcatcat  4560
tggaaaacgt tcttcggggc gaaaactctc aaggatctta ccgctgttga tccagttc    4620 gatgtaaccc actcgtgcac ccaactgatc ttcagcatct tttactttca ccagcgtttc  4680
tgggtgagca aaaacaggaa ggcaaaatgc cgcaaaaaag gaataagggc gacacggaa   4740 atgttgaata ctcatactct tcctttttca atattattga agcatttatc agggttattg  4800
tctcatgagc ggatacatat ttgaatgtat ttagaaaaat aaacaaatag gggttccgcg  4860
cacatttccc cgaaaagtgc cacctgacgt ctaagaaacc attattatca tgacattaac  4920
ctataaaaat aggcgtatca cgaggccctt tcgtctcgcg cgtttcggtg atgacggtga  4980
aaacctctga cacatgcagc tcccggagac ggtcacagct tgtctgtaag cggatgccgg  5040
gagcagacaa gcccgtcagg gcgcgtcagc gggtgttggc gggtgtcggg gctggcttaa  5100
ctatgcggca tcagagcaga ttgtactgag agtgcaccat atgcggtgtg aaataccgca  5160
cagatgcgta aggagaaaat accgcatcag gcgccattcg ccattcaggc tgcgcaactg  5220
ttgggaaggg cgatcggtgc gggcctcttc gctattacgc cagctggcga aggggggatg  5280
tgctgcaagg cgattaagtt gggtaacgcc agggttttcc cagtcacgac gttgtaaaac  5340
gacggccagt gccacgctct cccttatgcg actcctgcat taggaagcag cccagtagta  5400
ggttgaggcc gttgagcacc gccgccgcaa ggaatggtgc atgcaaggag atggcgccca  5460
acagtccccc ggccacgggg cctgccacca tacccacgcc gaaacaagcg ctcatgagcc  5520
cgaagtggcg agcccgatct tccccatcgg tgatgtcggc gatataggcg ccagcaaccg  5580
cacctgtggc gccggtgatg ccggccacga tgcgtccggc gtagaggcga tttaagaca   5640 ggatatcagt ggtccaggct ctagttttga ctcaacaata tcaccagctg aagcctatag  5700
agtacgagcc atagataaaa taaaagattt tatttagtct ccagaaaaag ggggaatga   5760 aagaccccac ctgtaggttt ggcaagctag cttaagtaac gccattttgc aaggcatgga  5820
aaatacataa ctgagaatag agaagttcag atcaaggtta ggaacagaga gacagcagaa  5880
tatgggccaa acaggatatc tgtggtaagc agttcctgcc ccggctcagg gccaagaaca  5940
gatggtcccc agatgcggtc ccgccctcag cagtttctag agaaccatca gatgtttcca  6000
```

```
gggtgcccca aggacctgaa aatgaccctg tgccttattt gaactaacca atcagttcgc     6060
ttctcgcttc tgttcgcgcg cttctgctcc ccgagctcaa taaaagagcc cacaacccct     6120
cactcggcgc gccagtcctc cgatagactg cgtcgcccgg gtacccgtat tcccaataaa     6180
gcctcttgct gtttgcatcc gaatcgtgga ctcgctgatc cttgggaggg tctcctcaga     6240
ttgattgact gcccacctcg ggggtctttc atttggaggt tccaccgaga tttggagacc     6300
cctgcctagg gaccaccgac cccccgccg ggaggtaagc tggccagcgg tcgtttcgtg      6360
tctgtctctg tctttgtgcg tgtttgtgcc ggcatctaat gtttgcgcct gcgtctgtac     6420
tagttagcta actagctctg tatctggcgg acccgtggtg gaactgacga gttcggaaca     6480
cccggccgca accctgggag acgtcccagg gacttcgggg gccgttttg tggcccgacc      6540 tgagtccaaa atcccgatc gttttggact ctttggtgca cccccttag aggagggata      6600 tgtggttctg gtaggagacg agaacctaaa acagttcccg cctccgtctg aattttgct     6660 ttcggtttgg gaccgaagcc gcgccgcgcg tcttgtctgc tgcagcatcg ttctgtgttg     6720
tctctgtctg actgtgtttc tgtatttgtc tgagaatatg ggcccgggct agcctgttac     6780
cactccctta agtttgacct taggtcactg gaaagatgtc gagcggatcg ctcacaacca     6840
gtcggtagat gtcaagaaga gacgttgggt taccttctgc tctgcagaat ggccaacctt     6900
taacgtcgga tggccgcgag acggcacctt taaccgagac ctcatcaccc aggttaagat     6960 caaggtctttt tcacctggcc cgcatggaca cccagaccag gtcccctaca tcgtgacctg    7020
ggaagccttg gcttttgacc cccctccctg ggtcaagccc tttgtacacc ctaagcctcc     7080
gcctcctctt cctccatccg ccccgtctct ccccccttgaa cctcctcgtt cgaccccgcc    7140
tcgatcctcc ctttatccag ccctcactcc ttctctaggc gccccatat ggccatatga      7200 gatcttatat ggggcacccc cgccccttgt aaacttccct gaccctgaca tgacaagagt     7260
tactaacagc ccctctctcc aagctcactt acaggctctc tacttagtcc agcacgaagt     7320
ctggagacct ctggcggcag cctaccaaga acaactggac cgaccggtgg tacctcaccc     7380
ttaccgagtc ggcgacacag tgtgggtccg ccgacaccag actaagaacc tagaaccctcg    7440 ctggaaagga ccttacacag tcctgctgac cacccccacc gccctcaaag tagacggcat     7500
cgcagcttgg atacacgccg cccacgtgag gctgccgacc ccgggggtgg accatcctct     7560
agaccgcctt ggcgcggccg atcctcacac aaaaaaccaa cacacagatg taatgaaaat     7620
aaagatattt tattgc                                                    7636
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15

```
ctgccatgga tgtgtcctca gaagcta                                          27
```

<210> SEQ ID NO 16
<211> LENGTH: 24
<212> TYPE: DNA
<213> ORGANISM: Artificial Sequence
<220> FEATURE:
<223> OTHER INFORMATION: Synthetic

<400> SEQUENCE: 16

```
attctcgagc ggccgctcag gcgg                                             24
```

```
<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
cggccgcgtc gtcggatccc ccg                                          23

<210> SEQ ID NO 18
<211> LENGTH: 23
<212> TYPE: DNA
<213> ORGANISM: Artificial Sequence
<220> FEATURE:
<223> OTHER INFORMATION: Synthetic

<400> SEQUENCE: 18
cgggggatcc gacgacgcgg ccg                                          23

<210> SEQ ID NO 19
<211> LENGTH: 48
<212> TYPE: DNA
<213> ORGANISM: Artificial Sequence
<220> FEATURE:
<223> OTHER INFORMATION: Synthetic

<400> SEQUENCE: 19
ggttctgtat tgtctgaaaa tagtcgaccg agctagctta agtaacgc               48

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
gcgttactta agctagctcg gtcgactatt ttcagacaat acagaacc               48

<210> SEQ ID NO 21
<211> LENGTH: 57
<212> TYPE: DNA
<213> ORGANISM: Artificial Sequence
<220> FEATURE:
<223> OTHER INFORMATION: Synthetic

<400> SEQUENCE: 21
ggccgcaata aaatatcttt attttcatta catctgtgtg ttggtttttt gtgtgag     57
```

INDUCIBLE INTERLEUKIN-12

CROSS-REFERENCE TO RELATED APPLICATIONS

Figure 1:
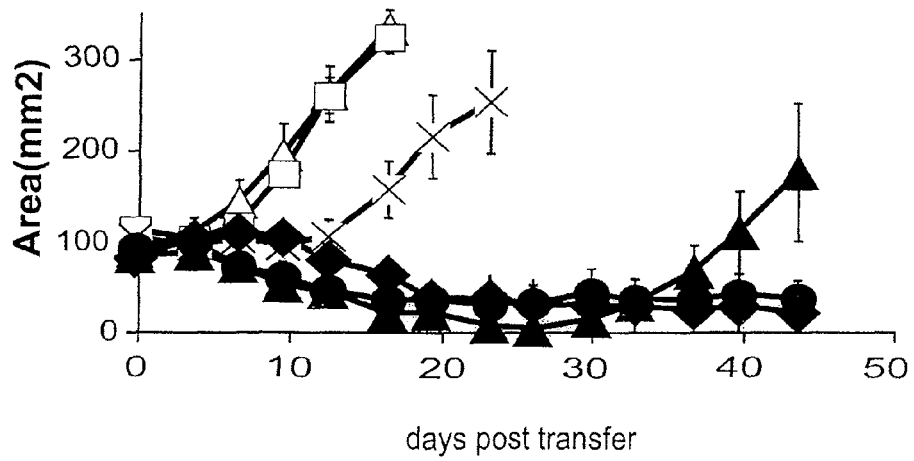
Figure 1:
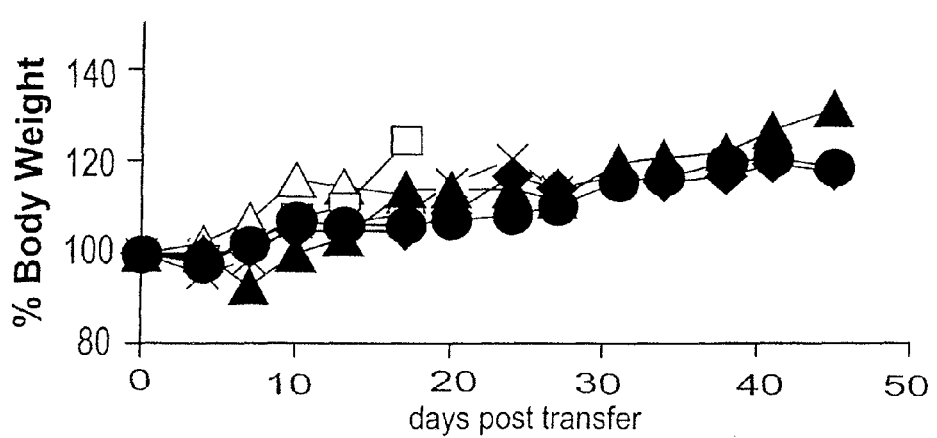
Figure 1:
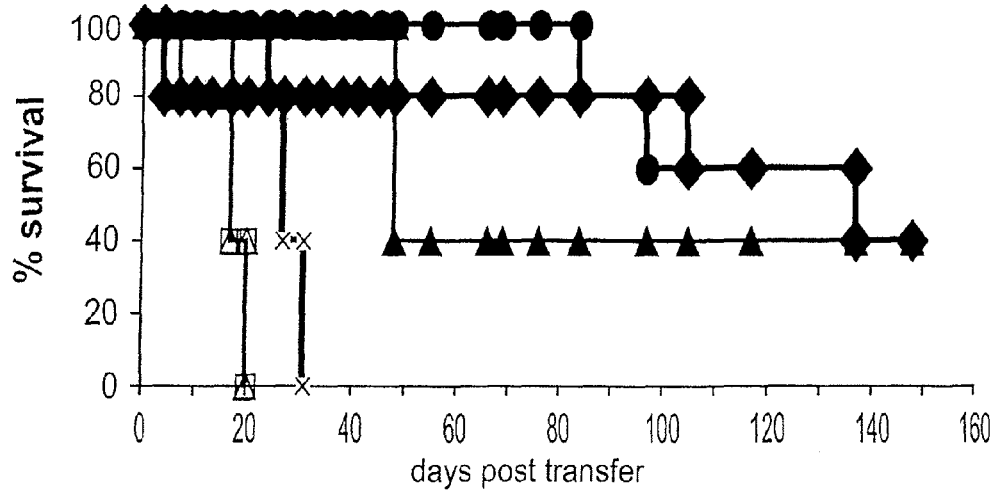

This patent application is a U.S. National Phase of International Patent Application No. PCT/US10/31988, filed Apr. 22, 2010, which claims the benefit of U.S. Provisional Patent Application No. 61/174,046, filed Apr. 30, 2009, which are incorporated by reference in their entirety herein.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 77,633 Byte ASCII (Text) file named "709090ST25.TXT," created on Oct. 12, 2011.

BACKGROUND OF THE INVENTION

Interleukin 12 (IL-12) is a heterodimeric, pro-inflammatory cytokine with varied functions in the immune system. For example, IL-12 enhances cytolytic activity by inducing the production of effector cytokines, e.g., interferon-γ (IFN-γ), TNF-α, and/or granulocyte macrophage colony stimulating factor (GM-CSF). IL-12 also enhances the production of T helper 1 (Th1) immunoglobulins by B cells and induces the differentiation of (Th1) cells.

Although recombinant IL-12 has demonstrated potent anti-cancer activity in animal models, recombinant IL-12 has provided only limited results in clinical trials (Del Vecchio et al. *Clin. Cancer Res.* 13(16):4677-85 (2007)). In addition, systemic administration of IL-12 in a phase II clinical trial for renal cell carcinoma resulted in severe toxicity for most of the enrolled patients and the deaths of two patients (Cohen, J. *Science* 270:(5238)908 (1995)).

In spite of considerable research into cancer treatments, there is a need for improved compositions and methods for treating and/or preventing cancer.

BRIEF SUMMARY OF THE INVENTION

An embodiment of the invention provides an isolated or purified nucleic acid comprising a nucleotide sequence encoding a nuclear factor of activated T-cells (NFAT) promoter operatively associated with a nucleotide sequence encoding IL-12.

Another embodiment of the invention provides a nucleic acid comprising a nucleotide sequence encoding a nuclear factor of activated T-cells (NFAT) promoter operatively associated with a nucleotide sequence encoding IL-12, wherein the NFAT promoter is located 3' of the nucleotide sequence encoding IL-12.

The invention further provides embodiments including recombinant expression vectors, host cells, populations of cells, and pharmaceutical compositions relating to the nucleic acids of the invention.

Methods of treating or preventing cancer in a mammal, methods of treating or preventing an infectious disease in a mammal, and methods of inducing IL-12 expression in a mammal are further provided by the invention. The inventive method of treating or preventing cancer in a mammal comprises administering to the mammal any nucleic acid, recombinant expression vector, host cell, population of host cells, or pharmaceutical composition described herein, in an amount effective to treat or prevent cancer in the mammal. The inventive method of treating or preventing an infectious disease in a mammal comprises administering to the mammal any nucleic acid, recombinant expression vector, host cell, population of host cells, or pharmaceutical composition described herein, in an amount effective to treat or prevent the infectious disease in the mammal.

An embodiment provides a pharmaceutically active agent selected from the group consisting of any of the nucleic acids, recombinant expression vectors, host cells, populations of cells, or pharmaceutical compositions described herein, for the treatment or prevention of cancer or an infectious disease.

An embodiment provides a method of inducing IL-12 expression in a mammal comprising a) isolating autologous T cells from a mammal; b) transducing the isolated T cells with any of the recombinant expression vectors of the invention; c) transducing the isolated T cells with a recombinant expression vector encoding a T cell receptor (TCR) to obtain expression of a TCR; d) administering the transduced cells to the mammal; and e) stimulating the TCR to induce IL-12 expression.

BRIEF DESCRIPTION OF THE SEVERAL VIEWS OF THE DRAWING(S)

FIG. 1A is a graph of tumor size (area $mm^2$) (y axis) at the indicated number of days post transfer of transduced cells (x axis). Treatments include: no treatment (-Δ-), $1\times10^6$ untransduced pmel T cells with vaccine and IL-2 treatment (-X-), $1\times10^6$ untransduced pmel T cells with no vaccine or IL-2 treatment (-□-), $5\times10^5$ cells transduced with mscIL-12 without NFAT (-▲-), $5\times10^5$ cells transduced with SEQ ID NO: 11 (-●-), and $5\times10^5$ cells transduced with SEQ ID NO: 12 (-◆-).

FIG. 1B is a graph of body weight (%) (y axis) at the indicated number of days post transfer of transduced cells (x axis). Treatments include: no treatment (-Δ-), $1\times10^6$ untransduced pmel T cells with vaccine and IL-2 treatment (-X-), $1\times10^6$ untransduced pmel T cells with no vaccine or IL-2 treatment (-□-), $5\times10^5$ cells transduced with mscIL-12 without NFAT (-▲-), $5\times10^5$ cells transduced with SEQ ID NO: 11 (-●-), and $5\times10^5$ cells transduced with SEQ ID NO: 12 (-◆-).

FIG. 1C is a graph of survival (%) (y axis) at the indicated number of days post transfer of transduced cells (x axis). Treatments include: no treatment (-Δ-), $1\times10^6$ untransduced pmel T cells with vaccine and IL-2 treatment (-X-), $1\times10^6$ untransduced pmel T cells with no vaccine or IL-2 treatment (-□-), $5\times10^5$ cells transduced with mscIL-12 without NFAT (-▲-) $5\times10^5$ cells transduced with SEQ ID NO: 11 (-●-), and $5\times10^5$ cells transduced with SEQ ID NO: 12 (-◆-).

Figure 2:
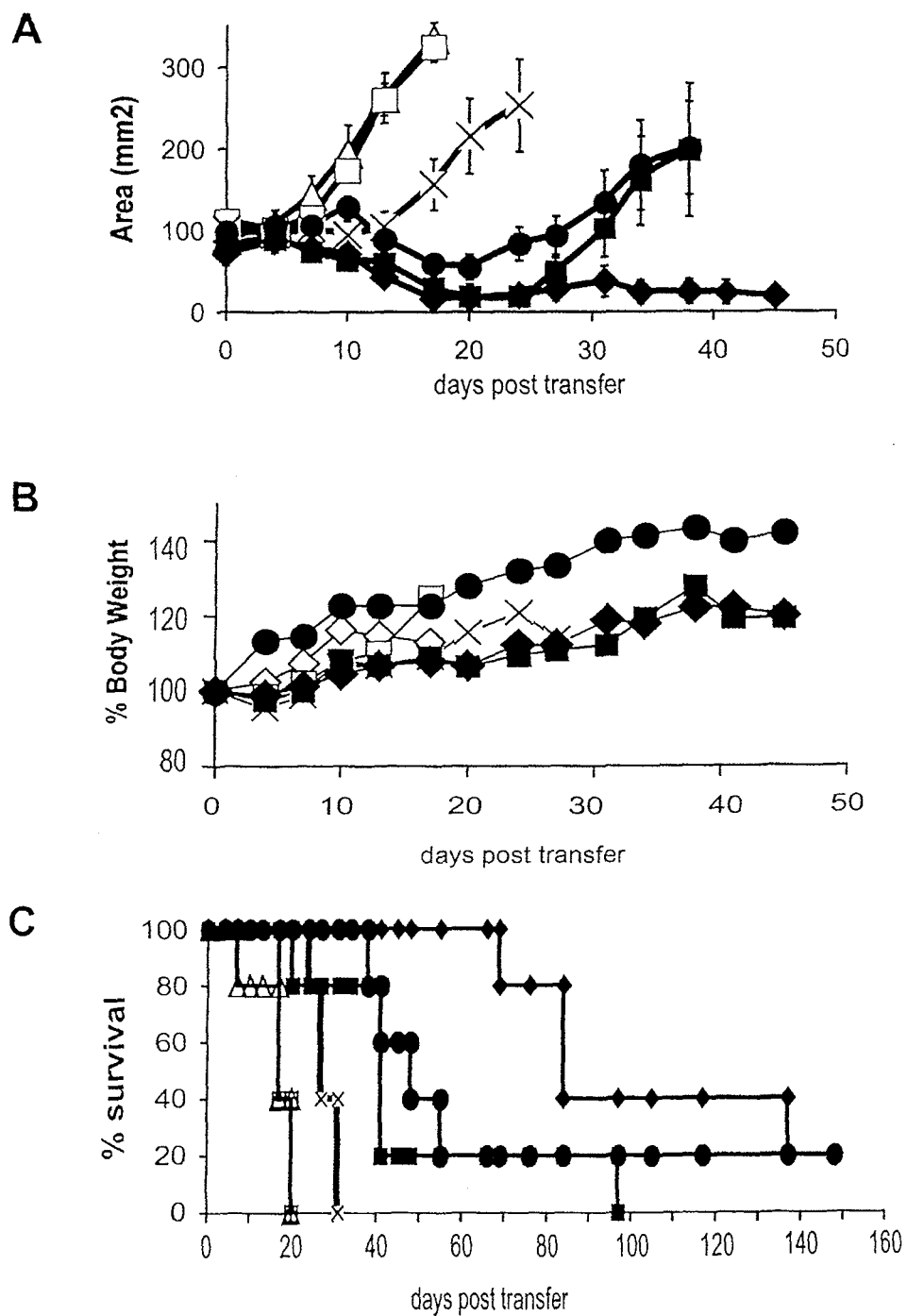

FIG. 2A is a graph of tumor size (area $mm^2$) (y axis) at the indicated number of days post transfer of transduced cells (x axis). Treatments include: no treatment (-Δ-), $1\times10^6$ untransduced pmel T cells with vaccine and IL-2 treatment (-X-), $1\times10^6$ untransduced pmel T cells with no vaccine or IL-2 treatment (-□-), $1\times10^5$ cells transduced with mscIL-12 without NFAT (-■-), $1\times10^5$ cells transduced with SEQ ID NO: 11 (-◆-), and $1\times10^5$ cells transduced with SEQ ID NO: 12 (-●-).

FIG. 2B is a graph of body weight (%) (y axis) at the indicated number of days post transfer of transduced cells (x axis). Treatments include: no treatment (-Δ-), $1\times10^6$ untransduced pmel T cells with vaccine and IL-2 treatment (-X-), $1\times10^6$ untransduced pmel T cells with no vaccine or IL-2 treatment (-□-), $1\times10^5$ cells transduced with mscIL-12 without NFAT (-■-), $1\times10^5$ cells transduced with SEQ ID NO: 11 (-◆-), and $1\times10^5$ cells transduced with SEQ ID NO: 12 (-●-).

FIG. 2C is a graph of survival (%) (y axis) at the indicated number of days post transfer of transduced cells (x axis).

Treatments include: no treatment (-△-), 1×10⁶ untransduced pmel T cells with vaccine and IL-2 treatment (-X-), 1×10⁶ untransduced pmel T cells with no vaccine or IL-2 treatment (-☐-), 1×10⁵ cells transduced with mscIL-12 without NFAT (-■-), 1×10⁵ cells transduced with SEQ ID NO: 11 (-◆-), and 1×10⁵ cells transduced with SEQ ID NO: 12 (-●-).

Figure 3:
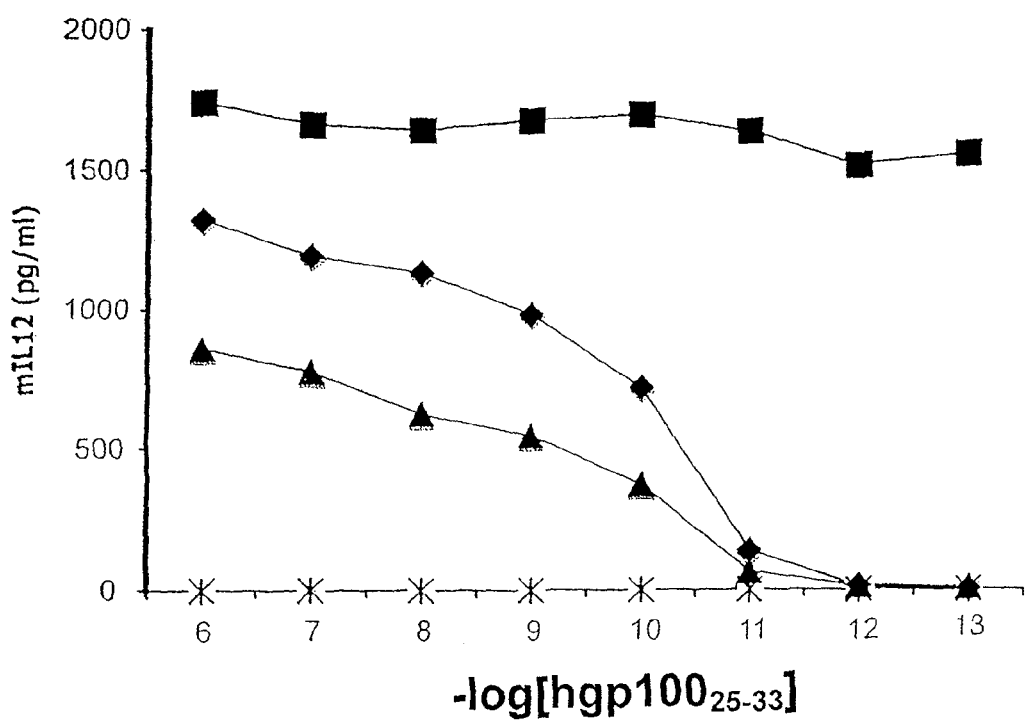

FIG. 3 is a graph of IL-12 production (pg/ml) (y axis) of transduced cells following co-culture with splenocyts pulsed with the indicated concentration (-log [hgp100$_{25-33}$]) of hgp100$_{25-33}$ peptide (x axis). Cells are transduced with SEQ ID NO: 11 (-◆-); SEQ ID NO: 12 (-▲-); MSGV1-GFP (*); or MSGV1-mflexIL12 (-■-).

DETAILED DESCRIPTION OF THE INVENTION

The invention provides a nucleic acid comprising a nucleotide sequence encoding a nuclear factor of activated T-cells (NFAT) promoter operatively associated with a nucleotide sequence encoding IL-12.

The invention provides a nucleic acid that encodes for inducible expression of IL-12 (or functional portion or functional variant thereof) with a nuclear factor of activated T-cells (NFAT) promoter or a functional portion or functional variant thereof. The nucleic acids of the invention advantageously make it possible to control the expression of IL-12 (or functional portion or functional variant thereof) to enhance cytolytic activity while also reducing or eliminating the toxicity of IL-12. In particular, cells comprising the nucleic acids of the invention advantageously express IL-12 (or functional portion or functional variant thereof) only when the cell (e.g., a T-cell receptor (TCR) expressed by the cell) is specifically stimulated by an antigen and/or the cell (e.g., the calcium signaling pathway of the cell) is non-specifically stimulated by, e.g., phorbol myristate acetate (PMA)/Ionomycin. Accordingly, the expression of IL-12 (or functional portion or functional variant thereof) can be controlled to occur only when and where it is needed, e.g., in the presence of an infectious disease-causing agent, cancer, or at a tumor site. Therefore, the production of unnecessary and/or excess IL-12 can be reduced or eliminated, which decreases or avoids IL-12 toxicity.

"Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleotide sequence encoding IL-12 encodes any suitable IL-12, including functional portions or functional variants thereof. The term "functional portion" refers to any part or fragment of the IL-12, which part or fragment retains the biological activity of the IL-12 of which it is a part (the parent IL-12). In reference to the parent IL-12, the functional portion can comprise, for instance, about 10%, 25%, 30%, 50%, 68%, 80%, 90%, 95%, or more, of the parent IL-12. The term "functional variant" as used herein refers to IL-12 having substantial or significant sequence identity or similarity to a parent IL-12, which functional variant retains the biological activity of the IL-12 of which it is a variant. In reference to the parent IL-12, the functional variant can, for instance, be at least about 30%, 50%, 75%, 80%, 90%, 98% or more identical in amino acid sequence to the parent IL-12. Functional portions and functional variants encompass, for example, those parts and variants, respectively, of IL-12 that retain the ability to induce the production of effector cytokines (e.g., IFN-γ, TNF-α, and/or GM-CSF), enhance the production of Th1 immunoglobulins, induce the differentiation of Th1 cells, or treat or prevent cancer, to a similar extent, the same extent, or to a higher extent, as the parent IL-12.

The nucleotide sequence encoding IL-12 (or functional portion or functional variant thereof) encodes any suitable mammalian IL-12 (or functional portion or functional variant thereof), e.g., human IL-12 or mouse IL-12. Preferably, the nucleotide sequence encoding IL-12 encodes human IL-12 (or functional portion or functional variant thereof). In this regard, the nucleotide sequence encoding IL-12 comprises or consists of SEQ ID NO: 2 (native, i.e., wild-type human IL-12) or functional portion or functional variant thereof.

In one embodiment, the nucleotide sequence encodes single chain IL-12. Alternatively, the nucleotide sequence encodes multiple chain IL-12. Preferably, the nucleotide sequence encodes no more than a single chain. Without being bound to a particular theory, it is believed that single chain IL-12 is transcribed and translated within the host cell more efficiently than multiple chain IL-12. Preferably, the nucleic acid encoding a single chain IL-12 comprises a nucleotide sequence encoding the p35 subunit of IL-12 linked to the p40 subunit of IL-12 with a linker sequence (e.g., a Gly6Ser linker sequence, a (Gly4Ser)3 linker sequence, or a furin SGSGP2A linker sequence). For example, SEQ ID NO: 3 comprises mouse single chain (msc) IL-12 with a (Gly4Ser)3 linker sequence. In this regard, the nucleotide sequence encoding IL-12 comprises or consists of SEQ ID NO: 3 or functional portion or functional variant thereof. In an especially preferred embodiment, the nucleic acid encoding a single chain IL-12 comprises a nucleotide sequence encoding the p35 subunit of IL-12 linked to the p40 subunit of IL-12 with a Gly6Ser linker sequence. In this regard, the nucleotide sequence encoding IL-12 comprises or consists of SEQ ID NO: 1 (human single chain (hsc) IL-12 with a Gly6Ser linker sequence) or functional portion or functional variant thereof.

In some embodiments, the nucleotide sequence may be optimized. Without being bound to a particular theory, it is believed that optimization of the nucleotide sequence increases the translation efficiency of the mRNA transcripts. Optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In this regard, the nucleotide sequence encoding IL-12 comprises or consists of SEQ ID NO: 1 (optimized human single chain IL-12) or functional portion or functional variant thereof.

The nucleic acid of the invention may comprise any suitable nucleotide sequence that encodes a NFAT promoter or a functional portion or functional variant thereof. "NFAT promoter" as used herein means one or more NFAT responsive elements linked to a minimal promoter of any gene expressed by T-cells. Preferably, the minimal promoter of a gene expressed by T-cells is a minimal human IL-2 promoter. The NFAT responsive elements may comprise, e.g., NFAT1, NFAT2, NFAT3, and/or NFAT4 responsive elements. The NFAT promoter (or functional portion or functional variant thereof) may comprise any number of binding motifs, e.g., at least two, at least three, at least four, at least five, or at least six, at least seven, at least eight, at least nine, at least ten, at least eleven, or up to twelve binding motifs. In a preferred embodiment, the NFAT promoter comprises six NFAT binding motifs. In an especially preferred embodiment, the NFAT promoter nucleotide sequence comprises or consists of SEQ ID NO: 4 or functional portion or functional variant thereof.

The NFAT promoter (or functional portion or functional variant thereof) is operatively associated with the nucleotide sequence encoding IL-12 (or functional portion or functional variant thereof). "Operatively associated with" means that the nucleotide sequence encoding IL-12 (or functional portion or functional variant thereof) is transcribed into IL-12 mRNA when the NFAT protein binds to the NFAT promoter sequence (or functional portion or functional variant thereof). Without being bound to a particular theory, it is believed that NFAT is regulated by a calcium signaling pathway. In particular, it is believed that TCR stimulation (by, e.g., an antigen) and/or stimulation of the calcium signaling pathway of the cell (by, e.g., PMA/Ionomycin) increases intracellular calcium concentration and activates calcium channels. It is believed that the NFAT protein is then dephosporylated by calmoduin and translocates to the nucleus where it binds with the NFAT promoter sequence (or functional portion or functional variant thereof) and activates downstream gene expression. By providing a NFAT promoter (or functional portion or functional variant thereof) that is operatively associated with the nucleotide sequence encoding IL-12 (or functional portion or functional variant thereof), the nucleic acids of the invention advantageously make it possible to express IL-12 (or functional portion or functional variant thereof) only when the host cell including the nucleic acid is stimulated by, e.g., PMA/Ionomycin and/or an antigen.

In an embodiment, the nucleic acid comprises the NFAT promoter (or functional portion or functional variant thereof) and IL-12 (or functional portion or functional variant thereof) sequences arranged in a "forward," i.e., from a 5' to 3' direction, respectively. In this regard, the NFAT promoter (or functional portion or functional variant thereof) is located 5' of the IL-12 (or functional portion or functional variant thereof) nucleotide sequence and the IL-12 (or functional portion or functional variant thereof) nucleotide sequence is located 3' of the NFAT promoter (or functional portion or functional variant thereof). In this regard, the nucleic acid comprises or consists of any of SEQ ID NO: 5 (hsc IL-12), SEQ ID NO: 6 (hsc IL-12), SEQ ID NO: 8 (hscIL-12), SEQ ID NO: 11 (msc IL-12), and functional portions or functional variants thereof. Moreover, the NFAT promoter (or functional portion or functional variant thereof) is located 5' of both the IL-12 (or functional portion or functional variant thereof) nucleotide sequence and any post-transcriptional regulatory element, (e.g., woodchuck hepatitis post-transcriptional regulatory element (WPRE)) and the IL-12 (or functional portion or functional variant thereof) nucleotide sequence is located 3' of the NFAT promoter (or functional portion or functional variant thereof) and 5' of the post-transcriptional regulatory element. In this regard, the nucleic acid comprises or consists of any of SEQ ID NO: 6 (hsc IL-12), SEQ ID NO: 11 (msc IL-12), and functional portions or functional variants thereof.

In another embodiment, the nucleic acid comprises the NFAT promoter (or functional portion or functional variant thereof) and IL-12 (or functional portion or functional variant thereof) sequences arranged in a "reverse," i.e., from a 3' to 5' direction, respectively. In this regard, the NFAT promoter (or functional portion or functional variant thereof) is located 3' of the IL-12 (or functional portion or functional variant thereof) nucleotide sequence and the IL-12 (or functional portion or functional variant thereof) nucleotide sequence is located 5' of the NFAT promoter (or functional portion or functional variant thereof). In this regard, the nucleic acid comprises or consists of any of SEQ ID NO: 7 (hsc IL-12), SEQ ID NO: 12 (msc IL-12), SEQ ID NO: 14 (hsc IL-12), and functional portions or functional variants thereof. Moreover, the NFAT promoter (or functional portion or functional variant thereof) is located 3' of both the IL-12 (or functional portion or functional variant thereof) nucleotide sequence and any post-transcriptional regulatory element, (e.g., a poly A tail (e.g., SV40 polyA tail, BGH polyA tail, polyA1 tail, poly A2 tail)), and the IL-12 (or functional portion or functional variant thereof) nucleotide sequence is located 5' of the NFAT promoter (or functional portion or functional variant thereof) and 3' of the post-transcriptional regulatory element. The arrangement of the NFAT promoter (or functional portion or functional variant thereof) and IL-12 (or functional portion or functional variant thereof) in a 3' to 5' direction, respectively, advantageously avoids expression of IL-12 until the nucleic acid is incorporated into the host cell genome and the host cell is stimulated by, e.g., PMA/Ionomycin and/or an antigen. Accordingly, the premature expression of IL-12 into the supernatant is advantageously reduced or eliminated.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl)uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides a functional variant of any of the nucleic acids described herein. The functional variant comprises a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleotide sequence encoding a NFAT promoter encodes any suitable NFAT promoter, including functional portions or functional variants thereof. The term "functional portion" refers to any part or fragment of the NFAT promoter, which part or fragment retains the biological activity of the NFAT promoter of which it is a part (the parent NFAT promoter). In reference to the parent NFAT promoter, the functional portion can comprise, for instance, about 10%, 25%, 30%, 50%, 68%, 80%, 90%, 95%, or more, of the parent NFAT promoter. Functional variants of a nucleotide sequence encoding a NFAT promoter, as used herein, refer to a NFAT promoter having substantial or significant sequence identity or similarity to a parent NFAT promoter, which functional variant retains the biological activity of the NFAT promoter of which it is a variant. Functional portions and functional variants encompass, for example, those parts and variants, respectively, of a NFAT promoter that retain the ability to bind NFAT protein, to a similar extent, the same extent, or to a higher extent, as the parent NFAT promoter.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand. It is generally appreciated that conditions can be rendered more stringent by the addition of increasing amounts of formamide.

The nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transduce any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the recombinant expression vector is a viral vector (e.g., adenoviral vector, adeno-associated viral (AAV) vector, herpes viral vector, retroviral vector, or lentiviral vector) or a transposon vector (e.g., Sleeping Beauty). In this regard, the recombinant expression vector comprises or consists of any of SEQ ID NO: 5 (lentiviral vector), SEQ ID NOs: 6-7, 11-12, and 14 (retroviral vectors), SEQ ID NO: 8 (Sleeping Beauty transposon vector), and functional portions or functional variants thereof.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based. Exemplary regulatory sequences include the WPRE and poly A tail sequences described herein.

The recombinant expression vector can include one or more marker genes, which allow for selection of transformed or transduced host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

Another embodiment of the invention further provides a host cell comprising any of the recombinant expression vectors described herein. As used herein, the term "host cell"

refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing IL-12 (or functional portion or functional variant thereof), the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells (TILs), memory T cells, naïve T cells, and the like. Preferably, the T cell is a CD8+ T cell or a CD4+ T cell.

The host cells can be transduced with the inventive nucleic acids using any suitable method. For example, host cells can be transduced with viral vectors using viruses (e.g., retrovirus or lentivirus) and host cells can be transduced with transposon vectors using electroporation.

In an embodiment, the host cell of the invention further comprises a nucleotide sequence encoding a TCR. The nucleotide sequence encoding a TCR encodes any suitable TCR, including functional portions or functional variants thereof. The term "functional portion" when used in reference to a TCR refers to any part or fragment of the TCR, which part or fragment retains the biological activity of the TCR of which it is a part (the parent TCR). In reference to the parent TCR, the functional portion can comprise, for instance, about 10%, 25%, 30%, 50%, 68%, 80%, 90%, 95%, or more, of the parent TCR. The term "functional variant" as used herein refers to a TCR, polypeptide, or protein having substantial or significant sequence identity or similarity to a parent TCR, which functional variant retains the biological activity of the TCR of which it is a variant. In reference to the parent TCR, polypeptide, or protein, the functional variant can, for instance, be at least about 30%, 50%, 75%, 80%, 90%, 98% or more identical in amino acid sequence to the parent TCR, polypeptide, or protein. Functional portions and functional variants encompass, for example, those parts and variants, respectively, of a parent TCR that retain the ability to specifically bind to the antigen, or treat or prevent cancer, to a similar extent, the same extent, or to a higher extent, as the parent TCR. The nucleotide sequence encoding a TCR may be included in any suitable recombinant expression vector, e.g., any of the recombinant expression vectors described herein.

The TCR (or functional portion or functional variant thereof) may be any suitable TCR (or functional portion or functional variant thereof), and may be a native (e.g., wild type) or non-native (e.g., substituted and/or chimeric) TCR (or functional portion or functional variant thereof). The TCR (or functional portion or functional variant thereof) has antigenic specificity for any antigen such as, for example, an infectious disease antigen (e.g., an HIV antigen, an influenza antigen, a Herpes virus antigen, a malaria antigen, a hepatitis antigen, etc.) or a cancer antigen. Preferably, the TCR (or functional portion or functional variant thereof) has antigenic specificity for a cancer antigen. The phrase having "antigenic specificity" as used herein means that the TCR (or functional portion or functional variant thereof) can specifically bind to and immunologically recognize an antigen, such that binding of the TCR (or functional portion or functional variant thereof) to the antigen elicits an immune response against the cell expressing the antigen. Nucleotide sequences encoding TCRs (or functional portions or functional variants thereof) are known in the art and may include, for example, those sequences disclosed in U.S. Pat. No. 5,830,755; U.S. patent application Ser. No. 11/575,077 (U.S. Patent Application Publication No. 2009/0053184); Ser. No. 12/196,833 (U.S. Patent Application Publication No. 2009/0042798); Ser. No. 12/298,927 (WO 2007/131092); and Ser. No. 12/443,111 (WO 2008/039818), which are incorporated herein by reference. An exemplary TCR is a human/mouse chimeric TCR (human TCR with a mouse constant region), DMF5 TCR (SEQ ID NO: 13) or a functional portion or functional variant thereof. Preferred TCRs include human gp100(154) TCR (SEQ ID NO: 9), human DMF4 TCR (SEQ ID NO: 10), and functional portions or functional variants thereof.

The term "cancer antigen" as used herein refers to any molecule (e.g., protein, peptide, lipid, carbohydrate, etc.) expressed by a tumor cell or cancer cell, such that the antigen is associated with the tumor or cancer. The cancer antigen can additionally be expressed by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult mammal. Alternatively, the cancer antigen can be additionally expressed by stem cells or precursor cells, which cells are not normally found in an adult mammal.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. Examples of cancer antigens include (but are not limited to) those antigens expressed by tumor suppressor genes (e.g., p53, RB), genes over expressed in tumors (e.g., Her2/neu, CEA, and PSMA), genes of the cancer/testis family (e.g., NY-ESO-1, and MAGE), or any gene known to elicit an antibody or T cell response in cancer. Other exemplary cancer antigens may include those disclosed in Neller et al. *Seminars in Immunol.*, 20: 286-295 (2008) and Parmiani et al., *J. Immunol.*, 178: 1975-79 (2007) and PSCA, HMW-MAA, CD19, VEGFR2, SSX, and EGFRvIII. In a preferred embodiment of the invention, the cancer antigen is a melanoma antigen. In a more preferred embodiment, the cancer antigen is a melanoma differentiation antigen, e.g., tyrosinase tumor antigen, gp100, TRP-1, TRP-2 or MART-1.

Also provided by an embodiment of the invention is a population of cells comprising at least one host cell described herein. The population of cells can be a heterogeneous population comprising the host cell comprising any of the recombinant expression vectors described herein, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The inventive nucleic acids, recombinant expression vectors, and host cells (including populations thereof) can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The inventive nucleic acids, recombinant expression vectors, and host cells (including populations thereof), all of which are collectively referred to as "inventive IL-12 materials" hereinafter, can be formulated into a composition, such as a pharmaceutical composition. In this regard, an embodiment of the invention provides a pharmaceutical composition comprising any of the nucleic acids, expression vectors, and host cells (including populations thereof) described herein, and a pharmaceutically acceptable carrier. The pharmaceutical composition can comprise an inventive IL-12 material in combination with other pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive IL-12 material, as well as by the particular method used to administer the inventive IL-12 material. Accordingly, there are a variety of suitable formulations of the pharmaceutical composition of the invention. The following formulations for parenteral, intratumoral, subcutaneous, intravenous, intramuscular, intraarterial, intrathecal, and interperitoneal administration are exemplary and are in no way limiting. More than one route can be used to administer the inventive IL-12 materials, and in certain instances, a particular route can provide a more immediate and more effective response than another route.

Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive IL-12 material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include, for example, petroleum, animal, vegetable, or synthetic oils. Specific examples of oils include peanut, soybean, sesame, cottonseed, corn, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Suitable soaps for use in parenteral formulations include, for example, fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.05% to about 50% by weight of the inventive IL-12 material in solution. Preservatives and buffers may be used. In order to minimize or eliminate irritation at the site of injection, such compositions may contain, for example, one or more nonionic surfactants having a hydrophile-lipophile balance (HLB) of from about 12 to about 17. The quantity of surfactant in such formulations will typically range, for example, from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)). Preferably, when administering cells, e.g., T cells, the cells are administered via injection.

It will be appreciated by one of skill in the art that, in addition to the above-described pharmaceutical compositions, the inventive IL-12 materials of the invention can be formulated as inclusion complexes, such as cyclodextrin inclusion complexes, nanoparticles, or liposomes.

For purposes of the invention, the amount or dose of the inventive IL-12 material administered should be sufficient to effect, e.g., a therapeutic or prophylactic response, in the subject or animal over a reasonable time frame. For example, the dose of the inventive IL-12 material should be sufficient to induce the production of effector cytokines (e.g., interferon-$\gamma$ (IFN-$\gamma$), TNF-$\alpha$, and/or granulocyte macrophage colony stimulating factor (GM-CSF)), enhance the production of Th1 immunoglobulins, induce the differentiation of Th1 cells, or, treat or prevent cancer in a period of from under about 30 minutes or about 30 minutes or longer, e.g., 12 to 24 or more hours, from the time of administration. In certain embodiments, the time period could be even longer. The dose will be determined by the efficacy of the particular inventive IL-12 material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-$\gamma$ is secreted by T cells comprising the inventive nucleic acid or recombinant expression vector upon administration of a given dose of such T cells to a mammal among a set of mammals of which each is given a different dose of the T cells, could be used to determine a starting dose to be administered to a mammal. The extent to which IFN-$\gamma$ is secreted upon administration of a certain dose can be assayed by methods known in the art, including, for instance, the methods described herein as Example 8.

The dose of the inventive IL-12 material also will be determined by the existence, nature and extent of any adverse side effects that might accompany the administration of a particular inventive IL-12 material. Typically, the attending physician will decide the dosage of the inventive IL-12 material with which to treat each individual patient, taking into consideration a variety of factors, such as age, body weight, general health, diet, sex, inventive IL-12 material to be administered, route of administration, and the severity of the condition being treated. By way of example and not intending to limit the invention, the dose of the inventive IL-12 material can be about 0.001 to about 1000 mg/kg body weight of the subject being treated/day, from about 0.01 to about 10 mg/kg body weight/day, about 0.01 mg to about 1 mg/kg body weight/day.

It is contemplated that the inventive pharmaceutical compositions, nucleic acids, recombinant expression vectors, host cells, or populations of cells can be used in methods of inducing IL-12 expression in a mammal or methods of treating or preventing cancer or an infectious disease. Without being bound to a particular theory, the nucleic acids of the invention advantageously make it possible to specifically induce the expression of IL-12 only when the host cell including the nucleic acid is stimulated by, e.g., (PMA)/Ionomycin and/or an antigen. Thus, the IL-12 expression can be controlled to occur only when and where it is needed, e.g., in the presence of cancer, an infectious disease-causing agent, or at a tumor site, thus reducing or eliminating the toxicity caused by the production of excess IL-12. Without being bound to a particular theory, it is believed that IL-12 is released specifically in the presence of cancer, an infectious disease-causing agent, or at a tumor site and little or no IL-12 will be released outside of the presence of cancer, an infectious disease-causing agent, or at a tumor site in order to reduce or eliminate the systemic toxicity of IL-12. IL-12 advantageously induces the production of effector cytokines (e.g., IFN-$\gamma$, TNF-$\alpha$, and/or GM-CSF), enhances the production of Th1 immunoglobulins, and/or induces the differentiation of T helper 1 (Th1) cells. In this regard, an embodiment of the invention provides a method of treating or preventing cancer in a mammal and a method of treating or preventing an infectious disease in a mammal, comprising administering to the mammal any of the pharmaceutical compositions, nucleic acids, recombinant expression vectors, host cells, or populations of cells described herein, in an amount effective to treat or prevent cancer or the infectious disease in the mammal.

Another embodiment of the invention provides a method of inducing IL-12 expression in a mammal. The method comprises isolating autologous T cells from a mammal and transducing the isolated T cells with any of the inventive recombinant expression vectors described herein. The method further comprises transducing the isolated T cells with a recombinant expression vector encoding a TCR or a functional portion or functional variant thereof to obtain expression of a TCR or a functional portion or functional variant thereof, administering the transduced cells to the mammal, and stimulating the TCR or a functional portion or functional variant thereof to induce IL-12 expression.

The TCR (or functional portion or functional variant thereof) of the methods of inducing IL-12 expression in a mammal may have antigenic specificity for any of the antigens, e.g., infectious disease antigens or cancer antigens, described herein. IL-12 expression may be measured using any of the methods described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer or an infectious disease in a mammal. Furthermore, the treatment or prevention provided by the inventive method can include treatment or prevention of one or more conditions or symptoms of the disease, e.g., cancer or an infectious disease, being treated or prevented. Also, for purposes herein, "prevention" can encompass delaying the onset of the disease, or a symptom or condition thereof.

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, ureter cancer, and urinary bladder cancer. Preferably, the cancer is skin cancer. More preferably, the cancer is melanoma.

With respect to the inventive methods, the infectious disease can be any infectious disease, including any of HIV, influenza, herpes, hepatitis, and malaria.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including *Felines* (cats) and *Canines* (dogs). It is more preferred that the mammals are from the order Artiodactyla, including *Bovines* (cows) and *Swines* (pigs) or of the order Perssodactyla, including *Equines* (horses). It is most preferred that the mammals are of the order Primates, Ceboids, or *Simoids* (monkeys) or of the order Anthropoids (humans and apes). An especially preferred mammal is the human.

An embodiment of the invention also provides a pharmaceutically active agent selected from the group consisting of any of the nucleic acids, recombinant expression vectors, host cells, populations of cells, or pharmaceutical compositions described herein, for the treatment or prevention of cancer or an infectious disease.

The following examples further illustrate the invention but, of course, should not be construed as in any way limiting its scope.

EXAMPLES

Patient PBMCs and Cell Lines

PBMCs used in these studies are from metastatic melanoma patients treated at the Surgery Branch, National Cancer Institute. The cell lines used in the experiments, including two HLA-A2+ restricted melanoma lines: Mel526, Mel624 and two HLA-A2-restricted: Mel888, and Mel938, are generated in the Surgery Branch from resected tumor lesions. Cell culture medium includes RPMI 1640 (Invitrogen™, Inc., Rockville, Md.) supplemented with 10% fetal calf serum (FCS) (Biofluid Inc., Gaithersburg, Md.), 100 U/ml penicillin, 100 µg/ml streptomycin, 2-mM L-glutamine, and 25 mM HEPES buffer solution (Invitrogen™).

FACS Analysis

IL-12 expression is determined using FITC-labeled human IL-12 Ab or PE-labeled mouse IL-12 (BD Pharmingen) for intracellular staining. The FACS intracellular staining is done with cytofix/cytoperm kit (BD Pharmingen). The cell apoptosis is measured by Annexin V-PE apoptosis detection kit I (BD Pharmingen). Immunofluorescence, analyzed as the relative log fluorescence of live cells, is measured using a FACScan flow cytometer (Becton Dickinson, Fullerton, Calif.). A combination of forward angle light scatter and propidium iodide (PI) staining is used to gate out dead cells. Approximately 1×10$^5$ cells are analyzed. Cells are stained in a FACS buffer made of PBS (Bio Whitaker, Walkersville, Md.) and 0.5% BSA. Immunofluorescence is analyzed using Flow Jo software (Tree Star, Inc., Ashland, Oreg.).

Example 1

Human single chain IL-12 (hscIL-12) is synthesized by the company GeneArt (codon optimized, SEQ ID NO: 1) and Epoch® Biolabs Inc. (wildtype, SEQ ID NO: 2) by linking the p40 subunit sequence and p35 subunit sequence with an amino acid linker of six Glycines and one Serine. The hscIL-12 is cloned into MSGV1 retrovirus vector using the Nco I and Xho I restriction sites to generate MSGV1-hIL12. The NFAT promoter, containing six repeating NFAT-binding motifs and a minimal IL-2 promoter (SEQ ID NO: 4), is cut from the pSIN-(NFAT)$_6$-GFP vector (Erik, H. et al., *Blood*, 96(2): 459-66(2000)) by Xho I and Bam HI and used to replace the PGK promoter of the pRRLSIN.cPPT.PGK.GFP lentivirus vector (Gregory L. et al., *Human Gene Ther.*, 14:497-507(2003)) digested with the same enzyme to generate a pRRLSIN.cPPT.NFAT.GFP vector.

The vector pRRLSIN.cPPT.NFAT.hscIL12 (SEQ ID NO: 5) is constructed by ligating three fragments: the NFAT promoter from the pRRLSIN.cPPT.NFAT.GFP vector cut with Xho I and Nco I, the hscIL12 fragment from the MSGV1-hIL12 vector cut with Nco I and Sac II, and the pRRLSIN.cPPT backbone from pRRLSIN.cPPT.PGK.GFP cut with Xho I and Sac II.

SEQ ID NO: 5 comprises the NFAT promoter located 5' of the IL-12 nucleotide sequence, and the IL-12 nucleotide sequence is located 3' of the NFAT promoter.

This example demonstrated a method of making a lentivirus vector comprising a nucleotide sequence encoding a nuclear factor of activated T-cells (NFAT) promoter operatively associated with a nucleotide sequence encoding human IL-12.

Example 2A

The pSERS11.NFAT.hIL12-F vector (SEQ ID NO: 6) is constructed by excising the GFP expression cassette from the pSERS11MP.GFP.Pre vector (Baum C. et al., *Mol. Ther.*, 13(2): 391-400 (2006); Baum C. et al., *Mol. Ther.*, 15(6): 1167-1173 (2007)) replacing the GFP expression cassette with the NFAT promoter and hscIL12 fragment of Example 1 using the Not I and Sal I enzyme sites.

SEQ ID NO: 6 comprises the NFAT promoter located 5' of both the IL-12 nucleotide sequence and WPRE, and the IL-12 nucleotide sequence is located 3' of the NFAT promoter and 5' of WPRE.

This example demonstrated a method of making a retrovirus vector comprising a nucleotide sequence encoding a nuclear factor of activated T-cells (NFAT) promoter operatively associated with a nucleotide sequence encoding human IL-12.

Example 2B

The self-inactivating γ-retroviral vector pSERS11MP.GFP (Schambach et al. *Mol Ther.* 13:391-400 (2006); Schambach et al. *Mol Ther.* 15:1167-1173 (2007)) is used to construct an inducible murine single chain IL-12 vector (mflexiIL12) (SEQ ID NO: 11). To create suitable enzyme sites in pSERS11MP.GFP, primers are designed to mutate Sal I at 2771 bp and create a new Sal I site at 1550 bp (upstream of MPSV promoter) in the vector. The primers are pSERS11MP.GFPa2774t-F (SEQ ID NO: 17), pSERS11MP.GFPa2774t-R (SEQ ID NO: 18), pSERS11MP.GFP1550M-F (SEQ ID NO: 19), and pSERS11MP.GFP1550M-R (SEQ ID NO: 20). The MPSV promoter in pSERS11MP.GFP (Sal I+Nco I) is replaced by the NFAT responsive promoter from LVV-NFAT.GFP (Nco I+Xho I) to generate pSER.NFAT.GFP.

The mflexiIL12 gene is amplified by PCR from MSGV1-mflexiIL12 to introduce NcoI and Xho I restriction enzyme sites and then cut and inserted into pSER.NFAT.GFP (cut with Nco I+Sal I) to generate the construct pSER.NFAT.m-flexiIL12-F. The primers are mflexiIL12-F (SEQ ID NO: 15) and mflexiIL12-R (SEQ ID NO: 16).

This example demonstrated a method of making a retrovirus vector comprising a nucleotide sequence encoding a nuclear factor of activated T-cells (NFAT) promoter operatively associated with a nucleotide sequence encoding human IL-12.

Example 3A

A PolyA sequence PA2 (57 bp) (SEQ ID NO: 21) is cloned into a pPB vector (synthesized by Epoch® Biolabs, Inc.) to yield pPB-PA2. An NFAT-GFP fragment is inserted into pPB-PA2 through the Sal I/Not I site to obtain pPB.NFAT.GF-P.PA2. The NFAT-GFP-PA2 fragment of pPB.NFAT.GF-P.PA2 is used to replace the GFP fragment of the pSERS11MP.GFP.Pre vector using Sal I and BamH I to obtain SERS11MP-NFAT-GFP-PA2. SEQ ID NO: 7 is constructed by replacing GFP expression cassette of the vector SERS11MP-NFAT-GFP-PA2 with the hscIL-12 fragment of SEQ ID NO: 6 produced in accordance with the methods described in Example 2A-2B using the Nco I and Not I enzyme sites.

SEQ ID NO: 7 comprises the NFAT promoter located 3' of both the IL-12 nucleotide sequence and poly A2 tail, and the IL-12 nucleotide sequence is located 5' of the NFAT promoter and 3' of the poly A2 tail.

This example demonstrated a method of making a retrovirus vector comprising a nucleotide sequence encoding a nuclear factor of activated T-cells (NFAT) promoter operatively associated with a nucleotide sequence encoding human IL-12.

Example 3B

SEQ ID NO: 12 is constructed by replacing GFP in vector pSER.NFAT.GFP.PA2 with mflexiIL12 from pSER.NFAT.m-flexiIL12-F described in Example 2B through the Nco I and Not I sites.

This example demonstrated a method of making a retrovirus vector comprising a nucleotide sequence encoding a nuclear factor of activated T-cells (NFAT) promoter operatively associated with a nucleotide sequence encoding human IL-12.

Example 4

On the day prior to the transduction of cells with retrovirus, $6 \times 10^6$ 293 GP cells (Clontech Laboratories, Inc., Mountain View, Calif.) are plated in 10 ml of DMEM (with 10% fetal calf serum (FCS) without antibiotics, Invitrogen™) supplemented with 10% FCS, 100 U/ml penicillin, 100 µg/ml streptomycin, 2-mM L-glutamine, and 25 mM HEPES buffer solution (Invitrogen™) on a 10 mm poly-D-lysine coated plate (Becton Dickinson, Fullerton, Calif.). On Day 0, mixtures are prepared as set forth in Table 1:

TABLE 1

| Mixture A | | Mixture B | |
|---|---|---|---|
| Retrovirus Vector (prepared according to the methods of any of Examples 2(A, B)-3(A, B)). | 9 µg | Lipofectamine 2000 (Invitrogen ™) | 60 µL |
| RD114 | 3-4 µg | OptiMEM ® medium | 1.5 mL |
| OptiMEM ® medium (Invitrogen ™) | 1.5 mL | — | |

Mixtures A and B are incubated separately for 5 minutes at room temperature. Mixtures A and B are gently mixed together and incubated for 20 minutes at room temperature. Three milliliters are added dropwise to 293 GP cells in a 10 mm plate (13 ml total).

The cells are incubated at 37° C. for 6-8 hours. The media is changed with 10 ml of DMEM medium supplemented with 10% FCS, 100 U/ml penicillin, 100 µg/ml streptomycin, 2-mM L-glutamine, and 25 mM HEPES buffer solution. The cells are incubated at 37° C. in 5% $CO_2$ for 48 hours. Retrovirus is harvested.

This example demonstrated a method of making a retrovirus comprising a recombinant expression vector comprising a nucleotide sequence encoding a nuclear factor of activated T-cells (NFAT) promoter operatively associated with a nucleotide sequence encoding IL-12.

Example 5

Peripheral blood lymphocytes (PBLs) are thawed from frozen stock stored at −180° C. and cultured in AIM-V medium (Invitrogen™ Life Technologies™) supplemented with 5% human AB serum (Gemini Bio-products, West Sacramento, Calif.), 50 ng/ml OKT3 (Ortho Biotech, Horsham, Pa.) and 300 IU/IL-2 (Novartis, Basel, Switzerland) at 37° C. and 5% $CO_2$ (Day 0). A non-tissue culture six-well plate (Becton Dickinson) is coated with 20 µg/ml RetroNectin (Takara Bio Inc., Otsu, Japan) for 2 hours at room temperature (RT) and blocked with PBS/2% BSA for 30 minutes at room temperature.

OKT3 activated PBLs are transduced with retroviral vectors on Days 2 and 3 using the coated plate. Retrovirus (prepared according to the method of Example 4) supernatant is spin-loaded onto the coated plates by centrifugation at 2000 g at 32° C. for 2 hours. The virus supernatant is removed and 4 ml of stimulated PBLs are loaded to each well at $0.5 \times 10^6$ cell/ml by centrifugation at 1000 g for 10 minutes and incubated at 37° C. and in 5% $CO_2$ overnight. The procedure is repeated the following day for a total of two transductions. On Day 4, the cells are expanded at 37° C. in a 5% $CO_2$ incubator and split as necessary to maintain cell density between 0.5 and $3 \times 10^6$ cells/ml.

This example demonstrated a method of transducing a host cell with a retroviral recombinant expression vector comprising a nucleotide sequence encoding a nuclear factor of activated T-cells (NFAT) promoter operatively associated with a nucleotide sequence encoding IL-12.

Example 6

On Day 0, 293FT cells (Invitrogen™) are plated onto 150 $mm^2$ poly-D-Lysine coated plates (Becton Dickinson labware, Fullerton, Calif.) in 15 ml medium (DMEM+10% fetal calf serum (without antibiotics)). On Day 1, mixtures are prepared as set forth in Table 2:

TABLE 2

| Mixture A | | Mixture B | |
|---|---|---|---|
| pMDLg/pRRE | 15 μg | Lipofectamine 2000 | 180 μL |
| pMD-G | 7.5 μg | OptiMEM ® medium | 2 mL |
| pRSV-Rev | 15 μg | — | |
| Lentivirus Vector (prepared according to the method of Example 1) | 22.5 μg | — | |
| OptiMEM ® medium | 2 mL | — | |

Mixtures A and B are incubated separately for 5 minutes at room temperature. Mixtures A and B are gently mixed together and incubated for 20 minutes at room temperature. Four milliliters are added dropwise to 293FT cells.

The cells are incubated at 37° C. for 6-8 hours. The cells are washed with phosphate buffered saline (PBS) 3 times. Media is changed with 20 mL of DMEM medium supplemented with 10% FCS, 100 U/ml penicillin, 100 μg/ml streptomycin, 2-mM L-glutamine, and 25 mM HEPES buffer. Lentivirus is harvested after 48 h. Cell debris is removed by centrifuge (6000 g for 10 min.). Lentivirus is used directly or stored at −80° C.

This example demonstrated a method of making a lentivirus comprising a recombinant expression vector comprising a nucleotide sequence encoding a nuclear factor of activated T-cells (NFAT) promoter operatively associated with a nucleotide sequence encoding IL-12.

Example 7

PBLs from donors are cultured in AIM-V medium supplemented with 300 IU/IL-2 at 37° C. in 5% $CO_2$ on Day 0. For transduction of activated PBLs, T cells are activated for 1 day (on Day 0) with OKT3 (50 ng/ml). Cells are plated ($1 \times 10^6$ per well) in a 24-well plate in 5 ml lentivirus (produced according to the method of Example 6) plus 1 ml AIM-V (IL-2 final 300 CU/ml) and centrifuged at 1000 g at 32° C. for 2 h in the presence of 10 μg/ml protamine sulfate (Abraxis, Schaumberg, Ill.). Following centrifuge, PBLs are placed in an incubator at 37° C. in 5% $CO_2$. The next day, the cells are transduced a second time by replacing 6 ml of supernatant with 5 ml of new lentivirus and 1 ml AIM-V medium and centrifuging at 1000 g at 32° C. for 2 h in the presence of 10 μg/ml protamine sulfate. Fresh AIM-V medium is changed on Day 3 to maintain cell density between 1 and $3 \times 10^6$ cell/ml.

This example demonstrated a method of transducing a host cell with a lentiviral recombinant expression vector comprising a nucleotide sequence encoding a nuclear factor of activated T-cells (NFAT) promoter operatively associated with a nucleotide sequence encoding IL-12.

Example 8

Human PBLs are obtained from a donor and are transduced with 1) a lentiviral vector encoding a gp100(154) TCR vector alone, 2) both a gp100(154) TCR vector and a lentiviral vector encoding a nuclear factor of activated T-cells (NFAT) promoter operatively associated with a nucleotide sequence encoding IL-12 (SEQ ID NO: 5), 3) a MART-1 TCR vector alone, or 4) both a MART-1 TCR vector and a lentiviral vector encoding a nuclear factor of activated T-cells (NFAT) promoter operatively associated with a nucleotide sequence encoding IL-12 (SEQ ID NO: 5), according to the method of Example 7. Transduced PBLs are treated by PMA (10 ng/ml) (Sigma Aldrich®, St. Louis, Mo.), Ionomycin (2.2 uM) (Sigma Aldrich®) overnight to stimulate IL-12 secretion.

On day 5, the co-transduced cells are co-cultured with target cells (tumor lines) Mel938 cells (HLA-A2−/gp100+), Mel888 cells (HLA-A2−/gp100+), Mel 624 cells (HLA-A2+/gp100+), or Mel526 cells (HLA-A2+/gp100+)) or PBL (control).

On day 6, PBL cultures are tested for reactivity in cytokine release assays using a commercially available ELISA kit (IFN-γ Endogen, Rockford, Ill.). For these assays, $1 \times 10^5$ responder cells (transduced PBLs) and $1 \times 10^5$ target cell (tumor lines) are incubated in a 0.2 ml culture volume in individual wells of 96-well plates overnight.

Cytokine secretion is measured in culture supernatants diluted as to be in the linear range of the assay. The results are set forth in Table 3.

TABLE 3

| | gp100(154) TCR alone (IFN-γ (pg/mL)) | gp100(154) TCR/SEQ ID NO: 5 (IFN-γ (pg/mL)) | MART-1 TCR alone (IFN-γ (pg/mL)) | MART-1 TCR/SEQ ID NO: 5 (IFN-γ (pg/mL)) |
|---|---|---|---|---|
| Mel526 | 3800 | 11000 | <500 | 7000 |
| Mel624 | 4100 | 9000 | 800 | 8100 |
| Mel888 | 0 | <500 | 0 | <500 |
| Mel938 | 0 | <500 | 0 | <500 |
| PBL | 0 | <500 | 0 | <500 |

As shown in Table 3, the tumor-antigen-mediated induction of IL-12 results in a concomitant 5- to 10-fold increase in IFN-γ production.

This example demonstrated that co-transduction of host cells with a gp100(154) TCR vector and a lentiviral vector comprising a nucleotide sequence encoding a nuclear factor of activated T-cells (NFAT) promoter operatively associated with a nucleotide sequence encoding IL-12 results in increased IFN-γ production.

Example 9

Donor PBL are transduced with a lentiviral vector encoding a gp100(154) TCR (SEQ ID NO: 9) alone, NFAT/hscIL-12 (SEQ ID NO: 5) alone, human DMF5 TCR (SEQ ID NO: 13) alone, or co-transduced with gp100(154) TCR (SEQ ID NO: 9) and SEQ ID NO: 5, or co-transduced with (SEQ ID NO: 5) and DMF5 TCR (SEQ ID NO: 13) as described in Example 7. The cells are co-cultured and stimulated to secrete IL-12 as described in Example 8. On day 6, PBL cultures are tested for reactivity in a cytokine release assay as described in Example 8 using a commercially available ELISA kit (human IL12; Endogen, Rockford, Ill.). The results are set forth in Table 4A.

TABLE 4A

| | NFAT/hscIL-12 (SEQ ID NO: 5) (IL-12 (pg/mL)) | gp100(154) TCR (IL-12 (pg/mL)) | gp100(154) TCR and NFAT/hscIL-12 (SEQ ID NO: 5) (IL-12 (pg/mL)) | DMF5 (SEQ ID NO: 13) (IL-12 (pg/mL)) | NFAT/hscIL-12 (SEQ ID NO: 5) and DMF5 (SEQ ID NO: 13) (IL-12 (pg/mL)) |
|---|---|---|---|---|---|
| Mel526 | 10 | 0 | 395 | 0 | 68 |
| Mel624 | 12 | 0 | 313 | 0 | 59 |

TABLE 4A-continued

| | NFAT/ hscIL-12 (SEQ ID NO: 5) (IL-12 (pg/mL)) | gp100(154) TCR (IL-12 (pg/mL)) | gp100(154) TCR and NFAT/ hscIL-12 (SEQ ID NO: 5) (IL-12 (pg/mL)) | DMF5 (SEQ ID NO: 13) (IL-12 (pg/mL)) | NFAT/ hscIL-12 (SEQ ID NO: 5) and DMF5 (SEQ ID NO: 13) (IL-12 (pg/mL)) |
|---|---|---|---|---|---|
| Mel888 | 22 | 0 | 0 | 0 | 0 |
| Mel938 | 22 | 0 | 0 | 0 | 0 |
| PBL | 19 | 0 | 0 | 0 | 0 |

As shown in Table 4A, IL-12 is only detected in the culture when double-engineered PBLs are co-cultured with HLA-A2 matched and antigen positive tumor targets (mel624 and mel526).

Transduced PBL cultures are also tested for reactivity in a cytokine release assay as described in Example 8 using a commercially available ELISA kit (human IL2; Endogen, Rockford, Ill.). The results are set forth in Table 4B (IL-2, pg/ml).

TABLE 4B

| | gp100(154) TCR (IL-2 (pg/mL)) | gp100(154) TCR and NFAT/hscIL-12 (SEQ ID NO: 5) (IL-2 (pg/mL)) | DMF5 (SEQ ID NO: 13) (IL-2 (pg/mL)) | NFAT/hscIL-12 (SEQ ID NO: 5) and DMF5 (SEQ ID NO: 13) (IL-2 (pg/mL)) |
|---|---|---|---|---|
| Mel526 | 150 | 190 | 90 | 100 |
| Mel624 | 350 | 400 | 50 | 60 |
| Mel888 | <50 | <50 | <50 | <50 |
| Mel938 | <50 | <50 | <50 | <50 |
| PBL | <50 | <50 | <50 | <50 |

As shown in FIG. 4B, IL-12 production does not affect IL-2 synthesis.

This example demonstrated that co-transduction of host cells with a TCR vector and a lentiviral vector comprising a nucleotide sequence encoding a nuclear factor of activated T-cells (NFAT) promoter operatively associated with a nucleotide sequence encoding IL-12 results in IL-12 production when co-cultured with Mel526 and Mel624 cells.

Example 10

Donor PBL are transduced, co-cultured, and stimulated to secrete IL-12 as described in Example 9. On day 6, PBL cultures are tested for reactivity in a cytokine release assay as described in Example 8 using a commercially available ELISA kit (TNF-α; Endogen, Rockford, Ill.). The results are set forth in Table 5.

TABLE 5

| | NFAT/ hscIL-12 (SEQ ID NO: 5) (TNF-α (pg/mL)) | gp100(154) TCR (TNF-α (pg/mL)) | gp100(154) TCR and NFAT/ hscIL-12 (SEQ ID NO: 5) (TNF-α (pg/mL)) | DMF5 (SEQ ID NO: 13) (TNF-α (pg/mL)) | NFAT/ hscIL-12 (SEQ ID NO: 5) and DMF5 (SEQ ID NO: 13) (TNF-α (pg/mL)) |
|---|---|---|---|---|---|
| Mel526 | 0 | 359 | 497 | 177 | 450 |
| Mel624 | 6 | 396 | 733 | 106 | 346 |
| Mel888 | 10 | 34 | 12 | 19 | 13 |
| Mel938 | 11 | 37 | 16 | 16 | 8 |
| PBL | 11 | 56 | 9 | 30 | 8 |

As shown in Table 5, the tumor-antigen-mediated induction of IL-12 results in a concomitant 2-fold increase in TNF-α production.

This example demonstrated that co-transduction of host cells with a TCR vector and a lentiviral vector comprising a nucleotide sequence encoding a nuclear factor of activated T-cells (NFAT) promoter operatively associated with a nucleotide sequence encoding IL-12 results in increased TNF-α production.

Comparative Example 11A

To examine the effect on cell proliferation by the constitutive expression of IL-12 and IFN-γ, PBLs are transduced with the hscIL12(G6S)-co vector (lacking NFAT) or a control vector tLNGFR, and cell growth is determined. The IL-12 transduced cells grow for approximately 7 days after transduction, but then decrease in number while control-vector-engineered cells continue to grow. The decline in cell numbers can not be attributed solely to the loss of IL-12 expressing cells, because only 25% are gene transduced, as measured by FACS using IL-12-FITC antibody. FACS analysis with 7-AAD/Annexin V staining demonstrates that more cells are undergoing apoptosis (positive for annexin V, but not 7-AAD) in the IL-12 engineered PBL culture compared with the control culture (17% vs. 6%). The percentage of cells undergoing apoptosis is decreased but not eliminated by treatment with anti-IL12R β2 antibody or anti-IFN-γ antibody (10% and 8.4% respectively versus 15% for control IgG). These data suggest that the induction of IL-12 and/or IFN-γ synthesis in hscIL12 (i.e., lacking NFAT) engineered T cells is inducing T cell apoptosis.

This comparative example demonstrated that cells transduced with a vector encoding IL-12 but lacking NFAT undergo apoptosis.

Example 11B

Donor PBL are transduced with a vector encoding GFP alone, co-transduced with a vector encoding GFP and a lentiviral vector SEQ ID NO: 5, co-transduced with a vector encoding gp100(154) TCR and a vector encoding GFP, or co-transduced with a vector encoding GFP and lentiviral vector SEQ ID NO: 5, as described in Example 7. The cells are co-cultured and stimulated to secrete IL-12 as described in Example 8. Expression of GFP and mouse Vβ (gp100(154) TCR) is confirmed in the various cells by FACS analysis.

In contrast to results with vectors constitutively expressing IL-12 but lacking NFAT (Comparative Example 11A), the NFAT regulated IL-12 vector-engineered PBL cultures expand up to 40-fold 11 days after stimulation and there is no statistical difference compared with cells transduced with control vectors (GFP only and gp100+GFP) (p=0.38).

Next, a rapid expansion protocol (REP) is performed on the transduced cells. (the REP methodology is used to produce large numbers of T cells often used in clinical applications). The cells are rapidly expanded on Day 7 or Day 12. On Day 0 of the rapid expansion protocol, a T25 flask is prepared with 25 ml complete medium (864 ml RPMI 1640, 100 ml 10% human AB Serum, 25 ml HEPES (1M), 10 ml Penicillin/Streptomycin, 1 ml 2-Mercaptoethanol, 1000 CU/ml IL-2), feeder cells ($2\times10^7$ irradiated PBMC, 4000 rads), 30 ng/ml (final concentration) anti-CD3 mAb (OKT3), and $1\times10^5$ CTL. The flask is placed in the incubator at 37° C., 5% $CO_2$. On Day 5 of the rapid expansion protocol, most of the media is removed from each flask; the media is replaced with CM containing IL-2 (1000 CU/ml). On Day 7-10, cells are counted and media is changed, if necessary. Fold expansion is determined. The results are shown in Table 6.

TABLE 6

| | Day 7 (fold expansion) | Day 12 (fold expansion) |
|---|---|---|
| GFP alone | 213 | 320 |
| gp100(154) TCR and SEQ ID NO: 5 | 180 | 224 |
| gp100(154) TCR and GFP | 167 | 500 |
| GFP and SEQ ID NO: 5 | 167 | 384 |

As shown in Table 6, the cells expand more than 150-fold in 7 days.

This example demonstrated that cells that are co-transduced with a TCR vector and a vector comprising a nucleotide sequence encoding a nuclear factor of activated T-cells (NFAT) promoter operatively associated with a nucleotide sequence encoding IL-12 can be rapidly expanded in vitro.

Example 12

Donor PBL are transduced or co-transduced as described in Example 11, co-cultured, and stimulated to secrete IL-12 as described in Example 8. Expression of GFP and mouse Vβ (gp100(154) TCR) is confirmed in the various cells by FACS analysis.

PBL cultures are tested for reactivity in a cytokine release assay as described in Example 8 using a commercially available ELISA kit (IFN-γ; Endogen, Rockford, Ill.) before and after rapid expansion (day 12), as described in Example 11.

Prior to rapid expansion, cells transduced with SEQ ID NO: 5 and a gp100(154) TCR vector secrete approximately 35000 pg/mL of IFN-γ when co-cultured with Mel526 cells and approximately 45000 pg/ml of IFN-γ when co-cultured with Mel624 cells (co-culture with each of PBL, Mel888 and Mel 938 yield less than approximately 5000 pg/mL of IFN-γ). Cells co-transduced with GFP and gp100(154) TCR or co-transduced with SEQ ID NO: 5 and GFP each yield less than approximately 5000 pg/ml IFN-γ in all co-cultures. Cells transduced with GFP alone yield 0 pg/mL IFN-γ in all co-cultures.

After rapid expansion (day 12), cells transduced with SEQ ID NO: 5 and a gp100(154) TCR vector secrete approximately 40000 pg/ml of IFN-γ when co-cultured with Mel526 or Mel624 cells (co-culture with each of PBL, Mel888 and Mel 938 yield less than approximately 6000 pg/mL of IFN-γ). Cells co-transduced with GFP and gp100(154) TCR or co-transduced with SEQ ID NO: 5 and GFP each yield less than approximately 5000 pg/ml IFN-γ in all co-cultures. Cells transduced with GFP alone yield 0 pg/mL IFN-γ in all co-cultures.

This example demonstrated that cells co-transduced with a TCR vector and a vector comprising a nucleotide sequence encoding a nuclear factor of activated T-cells (NFAT) promoter operatively associated with a nucleotide sequence encoding IL-12 maintain reactivity following rapid expansion in vitro.

Example 13

Donor PBL are untransduced (UT) or co-transduced with a retroviral vector encoding gp100(154) TCR and truncated low affinity nerve growth factor receptor (LNGFR); gp100(154) TCR and hscIL-12 without NFAT; gp100(154) TCR and SEQ ID NO: 6 (comprises NFAT located 5' of hscIL-12); or gp100(154) TCR and SEQ ID NO: 7 (comprises NFAT located 3' of hscIL-12) as described in Example 5. On day 7, the cells are co-cultured and stimulated to secrete IL-12 as described in Example 8. PBL cultures are tested for reactivity in a cytokine release assay as described in Example 8 using a commercially available ELISA kit (IFN-γ; Endogen, Rockford, Ill.). The results are set forth in Table 7.

TABLE 7

| | UT (IFN-γ (pg/mL)) | gp100(154) TCR and LNGFR (IFN-γ (pg/mL)) | gp100(154) TCR and hscIL-12 without NFAT (IFN-γ (pg/mL)) | gp100(154) TCR and SEQ ID NO: 6 (IFN-γ (pg/mL)) | gp100(154) TCR and SEQ ID NO: 7 (IFN-γ (pg/mL)) |
|---|---|---|---|---|---|
| Mel526 | 0 | 8766 | 52870 | 48320 | 60866 |
| Mel624 | 0 | 13272 | 57700 | 82920 | 77426 |
| Mel888 | 0 | 0 | 1192 | 178 | 696 |
| Mel938 | 0 | 0 | 675 | 411 | 0 |
| PBL | 0 | 0 | 0 | 0 | 0 |

As shown in Table 7, cells co-transduced with a gp100(154) TCR vector and either SEQ ID NO: 6 or SEQ ID NO: 7 secrete higher levels of IFN-γ than cells that were co-transduced with a gp100(154) TCR vector and a vector encoding hscIL-12 without the NFAT promoter when co-cultured with Mel624 cells.

This example demonstrated that co-transduction of host cells with a TCR vector and a retroviral vector comprising a nucleotide sequence encoding a nuclear factor of activated T-cells (NFAT) promoter operatively associated with a nucleotide sequence encoding IL-12 results in increased IFN-γ production as compared to cells co-transduced with a TCR vector and a vector encoding IL-12 but lacking NFAT.

Example 14

Donor PBL are co-transduced with a retroviral vector encoding gp100(154) TCR and LNGFR; gp100(154) TCR and hscIL-12 without NFAT; gp100(154) TCR and SEQ ID NO: 6 (comprises NFAT located 5' of hscIL-12); or gp100(154) TCR and SEQ ID NO: 7 (comprises NFAT located 3' of hscIL-12) as described in Example 5. The cells are co-cultured and stimulated to secrete IL-12 as described in Example 8 on day 7. PBL cultures are tested for reactivity in a cytokine release assay as described in Example 8 using a commercially available ELISA kit (human IL12; Endogen, Rockford, Ill.). The results are set forth in Table 8.

TABLE 8

| | gp100(154) TCR and LNGFR (IL-12 (pg/mL)) | gp100(154) TCR and hscIL-12 without NFAT (IL-12 (pg/mL)) | gp100(154) TCR and SEQ ID NO: 6 (IL-12 (pg/mL)) | gp100(154) TCR and SEQ ID NO: 7 (IL-12 (pg/mL)) |
|---|---|---|---|---|
| Mel526 | 0 | 4886 | 6104 | 2189 |
| Mel624 | 0 | 4474 | 6251 | 2038 |
| Mel888 | 0 | 2856 | 89 | 0 |
| Mel938 | 0 | 3090 | 80 | 0 |
| PBL | 0 | 5684 | 85 | 0 |

As shown in Table 8, cells co-transduced with a gp100 (154) TCR and SEQ ID NO: 6 or SEQ ID NO: 7 secrete IL-12 when co-cultured with Mel526 or Mel624 cells. Cells co-transduced with a gp100(154) TCR and SEQ ID NO: 7 secrete less IL-12 than cells co-transduced with gp100(154) TCR and hscIL-12 (without NFAT) when co-cultured with Mel526 or Mel624 cells.

IL-12 is detected in the viral supernatant as follows: gp100 (154) TCR and hscIL-12 without NFAT (4143 pg/ml); gp100 (154) TCR and SEQ ID NO: 6 (2542 pg/mL); and gp100(154) TCR and SEQ ID NO: 7 (742 pg/mL).

This example demonstrated that co-transduction of cells with a TCR vector and a vector comprising NFAT located 3' of hscIL-12 produces less IL-12 than cells co-transduced with gp100(154) TCR and hscIL-12 (without NFAT).

Example 15

Donor PBLs ($2 \times 10^6$/well) are transduced with retrovirus as described in Example 5 using the amounts set forth in Table 9.

TABLE 9

| GFP | Retrovirus comprising SEQ ID NO: 6 | TCR (DMF5 (SEQ ID NO: 13) or gp100(154) (SEQ ID NO: 9)) | Media |
|---|---|---|---|
| 1 ml | — | — | 3 ml |
| — | 1 ml | — | 3 ml |
| — | — | 1 ml | 3 ml |
| 1 ml | — | 1 ml | 2 ml |
| 0.5 ml | — | 1 ml | 2.5 ml |
| 0.25 ml | — | 1 ml | 2.75 ml |
| 0.125 ml | — | 1 ml | 2.9 ml |
| 0.0625 ml | — | 1 ml | 3.0 ml |
| — | 1 ml | 1 ml | 2 ml |
| — | 0.5 ml | 1 ml | 2.5 ml |
| — | 0.25 ml | 1 ml | 2.75 ml |
| — | 0.125 ml | 1 ml | 2.9 ml |
| — | 0.0625 ml | 1 ml | 3 ml |

Transduced cell apoptosis is measured by FACS analysis using Annexin V-PE apoptosis detection kit I (BD Pharmingen). As the amount of SEQ ID NO: 6 retrovirus added to cells is reduced, lower amounts of SEQ ID NO: 6 transduced cells stain positive for annexin, suggesting that lower amounts of SEQ ID NO: 6 retrovirus causes less apoptosis among transduced cells. Percent of cells staining positive for annexin is set forth in Table 10.

TABLE 10

| | 1 ml | 0.5 ml | 0.25 ml | 0.125 ml | 0.0625 ml |
|---|---|---|---|---|---|
| GFP | 1.76 | 1.35 | 1.7 | 1.36 | 2.19 |
| SEQ ID NO: 6 | 13 | 15.4 | 8.59 | 3.95 | 2.1 |

The transduced cells are co-cultured and stimulated to secrete IL-12 as described in Example 8. PBL cultures are tested for reactivity in a cytokine release assay as described in Example 8 using a commercially available ELISA kit (human IL12 and IFN-γ); Endogen, Rockford, Ill.).

The results of the IL-12 ELISA show that smaller amounts of retrovirus comprising SEQ ID NO: 6 result in smaller amounts of IL-12 being secreted by transduced cells when co-cultured with Mel526 and Mel624. When co-cultured with Mel526, cells co-transduced with DMF5 TCR and 1 ml, 0.5 ml, 0.25 ml, 0.125 ml, and 0.0625 ml of retrovirus comprising SEQ ID NO: 6 secrete approximately 800, 400, 300, 300, and 100 pg/ml of IL-12, respectively (co-cultures with Mel888, Mel938, and PBL yield 0 pg/ml IL-12). When co-cultured with Mel624, cells co-transduced with DMF5 TCR and 1 ml, 0.5 ml, 0.25 ml, 0.125 ml, and 0.0625 ml of retrovirus comprising SEQ ID NO: 6 secrete approximately 600, 300, 200, 150, and 50 pg/ml of IL-12, respectively. Cells transduced with SEQ ID NO: 6 alone secrete less than approximately 50 pg/ml of IL-12 in all co-cultures.

Conversely, the results of the IFN-γ show that smaller amounts of retrovirus comprising SEQ ID NO: 6 result in larger amounts of IFN-γ being secreted by transduced cells when co-cultured with Mel526 and Mel624. When co-cultured with Mel526, cells co-transduced with DMF5 TCR and 1 ml, 0.5 ml, 0.25 ml, 0.125 ml, and 0.0625 ml of retrovirus comprising SEQ ID NO: 6 secrete approximately 6000, 6000, 9000, 13000, and 14000 pg/ml of IFN-γ, respectively (co-cultures with Mel888, Mel938, and PBL yield less than 700 pg/ml IFN-γ). When co-cultured with Mel624, cells co-transduced with DMF5 TCR and 1 ml, 0.5 ml, 0.25 ml, 0.125 ml, and 0.0625 ml of retrovirus comprising SEQ ID NO: 6 secrete approximately 5000, 6000, 7000, 10000, and 8000 pg/ml of IFN-γ, respectively. Cells transduced with GFP alone secrete 0 pg/ml of IFN-γ, and cells transduced with SEQ ID NO: 6 alone secrete less than approximately 300 pg/ml of IFN-γ, in all co-cultures.

When co-cultured with Mel526, cells transduced with DMF5 TCR alone and cells co-transduced with DMF5 TCR and 1 ml, 0.5 ml, 0.25 ml, 0.125 ml, and 0.0625 ml of retrovirus comprising GFP secrete approximately 2000, 1000, 2000, 3000, 1000, and 2000 pg/ml of IFN-γ, respectively (co-cultures with Mel888, Mel938, and PBL yield less than 400 pg/ml IFN-γ). When co-cultured with Mel624, cells transduced with DMF5 TCR and co-transduced with DMF5 TCR and 1 ml, 0.5 ml, 0.25 ml, 0.125 ml, and 0.0625 ml of retrovirus comprising SEQ ID NO: 6 secrete approximately 2000, 1000, 1000, 1000, 800, and 2000 pg/ml of IFN-γ, respectively.

This example demonstrates that the smaller the amount of retrovirus comprising NFAT located 5' to IL-12, the healthier the cells, the larger the yield of IFN-γ, and the smaller the yield of IL-12.

Example 16

Donor PBLs ($2 \times 10^6$/well) are transduced with retrovirus as described in Example 5 using the amounts set forth in Table 9, except that SEQ ID NO: 7 is used in place of SEQ ID NO: 6.

Transduced cell apoptosis is measured by a propidium iodide (PI) uptake assay. Lower amounts of SEQ ID NO: 7 retrovirus take up PI, suggesting that lower amounts of SEQ ID NO: 7 retrovirus caused less apoptosis among transduced cells. Percent of cells taking up PI is set forth in Table 11.

TABLE 11

|  | 1 ml | 0.5 ml | 0.25 ml | 0.125 ml | 0.0625 ml |
|---|---|---|---|---|---|
| GFP | 10.4 | 8.65 | 8.96 | 9.04 | 9.16 |
| SEQ ID NO: 6 | 30 | 17.3 | 12.7 | 10.2 | 8.42 |

The transduced cells are co-cultured and stimulated to secrete IL-12 as described in Example 8. PBL cultures are tested for reactivity in a cytokine release assay as described in Example 8 using a commercially available ELISA kit (human IL12 and IFN-γ); Endogen, Rockford, Ill.).

The results of the IL-12 ELISA show that smaller amounts of retrovirus comprising SEQ ID NO: 7 result in smaller amounts of IL-12 being secreted by transduced cells when co-cultured with Mel526 and Mel624. When co-cultured with Mel526, cells co-transduced with DMF5 TCR and 1 ml, 0.5 ml, 0.25 ml, 0.125 ml, and 0.0625 ml of retrovirus comprising SEQ ID NO: 7 secrete approximately 600, 500, 200, 150, and 40 pg/ml of IL-12, respectively (co-cultures with Mel888, Mel938, and PBL yield 0 pg/ml IL-12). When co-cultured with Mel624, cells co-transduced with DMF5 TCR and 1 ml, 0.5 ml, 0.25 ml, 0.125 ml, and 0.0625 ml of retrovirus comprising SEQ ID NO: 7 secrete approximately 1200, 1000, 300, 150, and 50 pg/ml of IL-12, respectively. Cells transduced with SEQ ID NO: 7 alone secrete approximately 20 pg/ml or less of IL-12 in all co-cultures.

The results of the IFN-γ show that smaller amounts of retrovirus comprising SEQ ID NO: 7 result in smaller amounts of IFN-γ being secreted by transduced cells when co-cultured with Mel526 and Mel624. When co-cultured with Mel526, cells co-transduced with DMF5 TCR and 1 ml, 0.5 ml, 0.25 ml, 0.125 ml, and 0.0625 ml of retrovirus comprising SEQ ID NO: 7 secrete approximately 120000, 150000, 70000, 50000, and 50000 pg/ml of IFN-γ, respectively (co-cultures with Mel888, Mel938, and PBL yield less than 2000 pg/ml IFN-γ). When co-cultured with Mel624, cells co-transduced with DMF5 TCR and 1 ml, 0.5 ml, 0.25 ml, 0.125 ml, and 0.0625 ml of retrovirus comprising SEQ ID NO: 7 secrete approximately 150000, 230000, 110000, 100000, and 50000 pg/ml of IFN-γ, respectively. Cells transduced with GFP alone secrete 0 pg/ml of IFN-γ, and cells transduced with SEQ ID NO: 7 alone secrete less than approximately 3000 pg/ml of IFN-γ, in all co-cultures.

When co-cultured with Mel526, cells transduced with DMF5 TCR alone and cells co-transduced with DMF5 TCR and 1 ml, 0.5 ml, 0.25 ml, 0.125 ml, and 0.0625 ml of retrovirus comprising GFP secrete approximately 1000 pg/ml of IFN-γ, each (co-cultures with Mel888, Mel938, and PBL yield negligible amounts of IFN-γ). When co-cultured with Mel624, cells transduced with DMF5 TCR and co-transduced with DMF5 TCR and 1 ml, 0.5 ml, 0.25 ml, 0.125 ml, and 0.0625 ml of retrovirus comprising SEQ ID NO: 7 secrete approximately 2000 pg/ml of IFN-γ, each.

The experiments of this example are repeated using gp100 (154) TCR instead of DMF5 TCR, and similar trends are observed for IFN-γ and IL-12 secretion versus amount of retrovirus.

This example demonstrates that the smaller the amount of retrovirus comprising NFAT located 3' to IL-12, the healthier the cells and the smaller the yield of IL-12.

Example 17

Donor PBLs (2×10⁶/well) are transduced with retrovirus as described in Example 5 using the amounts set forth in Table 9, except that SEQ ID NO: 7 is used in place of SEQ ID NO: 6. On day 7, the cells are rapidly expanded, as described in Example 11.

Cells transduced with SEQ ID NO: 7 alone and cells co-transduced with DMF5 TCR and 1 ml, 0.5 ml, 0.25 ml, 0.125 ml, and 0.0625 ml of retrovirus comprising SEQ ID NO: 7 demonstrate approximately 30, 20, 30, 40, 50, 70-fold expansion, respectively.

Cells transduced with GFP alone and DMF5 TCR alone demonstrate approximately 60 and 70-fold expansion, respectively. Cells transduced with DMF5 TCR and 1 ml, 0.5 ml, 0.25 ml, 0.125 ml, and 0.0625 ml of retrovirus comprising GFP demonstrate approximately 55, 60, 70, 75, and 60-fold expansion, respectively.

The experiments of this example are repeated using gp100 (154) TCR instead of DMF5 TCR, and rapidly expanding transduced cells on Day 10, and a similar trend is observed for rapid expansion of the transduced cells versus amount of retrovirus.

This example demonstrates that, in general, the smaller the amount of retrovirus comprising NFAT located 3' to IL-12, the greater the expansion of cells.

Example 18

Three days prior to transduction, 293 GP cells are plated. The following day, the cells are transfected and retrovirus is produced as described in Example 4 including recombinant expression vectors SEQ ID NO: 11 (mscIL-12 with the NFAT promoter located 5' of IL-12), SEQ ID NO: 12 (mscIL-12 with the NFAT promoter located 3' of IL-12), a vector encoding mscIL-12 lacking an NFAT promoter, or a vector encoding GFP. The retrovirus is harvested and are Pmel T cells are transduced (Day 0). On Day 4, expression of mscIL-12 is confirmed by FACS analysis and mIL-12 secretion is measured by ELISA (5×10⁵ transduced cells treated with PMA) as described in Example 8. The results are set forth in Table 12.

TABLE 12

| Retroviral Vector | PBL mIL-12 (pg/ml) | Treated with PMA/Ionomycin: mIL-12 (pg/ml) |
|---|---|---|
| GFP | 0 | 0 |
| mscIL-12 (lacking NFAT) | 3150 | 3523 |
| SEQ ID NO: 11 | 2 | 197 |
| SEQ ID NO: 12 | 1 | 141 |

As shown in Table 12, cells transduced with SEQ ID NOs: 11 or 12 secrete IL-12 when stimulated with PMA/Ionomycin and do not secrete IL-12 when not stimulated with PMA/Ionomycin.

C57BL/6 and pmel-transgenic mice (Jackson Laboratory, Bar Harbor, Me.) are housed at the National Institute of Health (NIH). B16 (H-2$^b$), a spontaneous gp100+ murine melanoma, is maintained in RPMI with 10% FBS.

C57BL/6 mice at 6 to 12 weeks of age are injected with 2×10⁵ to 5×10⁵ B16 melanoma cells. Ten days later, groups of tumor bearing mice (N=5) are treated as set forth in Table 13. Mice are treated with 5Gy lymphodepleting irradiation followed by cell transfer through tail vein injection. Mice are vaccinated on the day of transfer with 2×10⁷ PFU of recombinant fowlpox virus expressing human gp100 (rFPhgp100; Therion Biologics, Cambridge, Mass.) and 600,000 IU IL-2 intraperitoneally once daily for 3 days. The perpendicular diameters of the tumors are measured with a caliper by a blinded investigator twice a week. The change in percentage of body weight from the start of treatment is recorded for each treatment group. The NCI Animal Ethics Committee of the NIH approved all animal experiments.

TABLE 13

| Group | No. of Pmel T cells | Vector | Vaccine | IL-2 |
|---|---|---|---|---|
| 1. | | No treatment. | | |
| 2. | $1 \times 10^6$ | None | Yes | Yes |
| 3. | $1 \times 10^6$ | None | None | None |
| 4. | $5 \times 10^5$ | mscIL-12 without NFAT | None | None |
| 5. | $5 \times 10^5$ | SEQ ID NO: 11 | None | None |
| 6. | $5 \times 10^5$ | SEQ ID NO: 12 | None | None |
| 7. | $1 \times 10^5$ | mscIL-12 without NFAT | None | None |
| 8. | $1 \times 10^5$ | SEQ ID NO: 11 | None | None |
| 9. | $1 \times 10^5$ | SEQ ID NO: 12 | None | None |

The results are set forth in FIGS. 1A-1C and 2A-2C. As shown in FIG. 1A, administration of T cells transduced with SEQ ID NO: 11 ($5 \times 10^5$ cells) or SEQ ID NO: 12 ($5 \times 10^5$ cells) to tumor-bearing mice, without administration of IL-2 or vaccine, results in greatly enhanced tumor regression compared with the administration of pmel-1 T cells only (i.e., lacking SEQ ID NO: 11 or 12). The body weight of mice receiving T cells transduced with SEQ ID NO: 11 or SEQ ID NO: 12 also increases during the study (FIG. 1B). In addition, as shown in FIG. 1C, tumor bearing mice receiving T cells transduced with SEQ ID NO: 11 ($5 \times 10^5$ cells) or SEQ ID NO: 12 ($5 \times 10^5$ cells) have a prolonged survival compared to mice that do not receive T cells transduced with SEQ ID NO: 11 ($5 \times 10^5$ cells) or SEQ ID NO: 12 ($5 \times 10^5$ cells). These results are observed in two independent experiments.

Similar treatment efficacy is observed using $1 \times 10^5$ cells pmel-1 cells transduced with SEQ ID NO: 11. As shown in FIG. 2A, administration of T cells transduced with SEQ ID NO: 11 ($1 \times 10^5$ cells) or SEQ ID NO: 12 ($1 \times 10^5$ cells) to tumor-bearing mice, without administration of IL-2 or vaccine, results in greatly enhanced tumor regression compared with the administration of pmel-1 T cells only (i.e., lacking SEQ ID NO: 11 or 12). The body weight of mice receiving T cells transduced with SEQ ID NO: 11 or SEQ ID NO: 12 also increases during the study (FIG. 2B). In addition, as shown in FIG. 2C, tumor bearing mice receiving T cells transduced with SEQ ID NO: 11 ($1 \times 10^5$ cells) or SEQ ID NO: 12 ($1 \times 10^5$ cells) have a prolonged survival compared to mice that do not receive T cells transduced with SEQ ID NO: 11 ($1 \times 10^5$ cells) or SEQ ID NO: 12 ($1 \times 10^5$ cells).

The production of IL-12 in these inducible vectors (SEQ ID NO: 11 and 12) is compared to a γ-retroviral vector that constitutively expresses murine IL-12 (MSGV1-mflexiIL12) (i.e., lacking NFAT). Pmel-1 T cells are primed with $hgp_{25-33}$ 100 peptide for 24 hours and transduced with the three different vectors (SEQ ID NO: 11, SEQ ID NO: 12, MSGV1-mflexiIL12 (i.e., lacking NFAT), or a vector encoding GFP only. After 48 hours, the transduced cells are co-cultured with C57BL/6 splenocytes pulsed with $hgp100_{25-33}$ peptide at various concentrations. While the LTR-driven MSGV1-mflexiIL12 vector (lacking NFAT) produces a constant amount of cytokine, the IL12 production driven by the human NFAT responsive promoter is induced by TCR recognition of the specific antigen peptide ($hgp100_{25-33}$) in a dose dependent manner (FIG. 3).

This example demonstrated that adoptive transfer of cells transduced with a nucleic acid comprising a nucleotide sequence encoding an NFAT promoter operatively associated with a nucleotide sequence encoding IL-12 causes regression of large established B16 melanomas without administration of IL-2 or vaccine.

Example 19

Cells are centrifuged at 100 g for 15 minutes and the supernatant is removed. The cells are suspended with 96-well nucleofector solution (Lonza, Walkersville, Md.) at $1 \times 10^6$ cells/20 µl aliquot in a 96 well plate (20 µl per well). Transposon vector (SEQ ID NO: 8) (1 µg) and 1 µg transposase is added to each well (2 µg in 4 µl maximum). The electroporation plate is placed into a Nucleofector 96-well shuttle (Lonza, Walkersville, Md.) and the nucleofection process is started.

After electroporation, 80 µl prewarmed AIM-V medium (without IL-2) is added to the plate and the plate is incubated at 37° C. for 10 minutes. The cells are transferred into a pre-warmed, 96-well plate with 160 µl AIM-V medium (without IL-2) and incubated at 37° C. in 5% $CO_2$ for 4 hours. The cells are spun down at 100 g for 15 minutes and resuspended with AIM-V medium (with IL2 300 IU/ml) and incubated at 37° C. in 5% $CO_2$. Gene expression is measured 48 hours later.

This example demonstrated a method of transducing cells with a transposon vector comprising a nucleotide sequence encoding a nuclear factor of activated T-cells (NFAT) promoter operatively associated with a nucleotide sequence encoding IL-12 by electroporation.

Example 20

Human PBLs are obtained from a donor and are co-transduced with a DMF4 TCR vector (SEQ ID NO: 10) and one of GFP, SEQ ID NO: 6, or SEQ ID NO: 7, according to the method of Example 7. Transduced PBLs are treated by PMA (10 ng/ml) (Sigma Aldrich®, St. Louis, Mo.), Ionomycin (2.2 uM) (Sigma Aldrich®) overnight to stimulate IL-12 secretion.

On day 5, the co-transduced cells are co-cultured with target cells (tumor lines) Mel938 cells (HLA-A2–/gp100+), Mel888 cells (HLA-A2–/gp100+), Mel 624 cells (HLA-A2+/gp100+), or Mel526 cells (HLA-A2+/gp100+)) or PBL (control).

On day 6, PBL cultures are tested for reactivity in cytokine release assays using a commercially available ELISA kit (IFN-γ Endogen, Rockford, Ill.). For these assays, $1 \times 10^5$ responder cells (transduced PBLs) and $1 \times 10^5$ target cell (tumor lines) are incubated in a 0.2 ml culture volume in individual wells of 96-well plates overnight.

Cytokine secretion is measured in culture supernatants diluted as to be in the linear range of the assay. The results are set forth in Table 14.

TABLE 14

| | DMF4 (SEQ ID NO: 10) and GFP (IFN-γ pg/ml) | DMF4 (SEQ ID NO: 10) and SEQ ID NO: 6 (IFN-γ pg/ml) | DMF4 (SEQ ID NO: 10) and SEQ ID NO: 7 (IFN-γ pg/ml) |
|---|---|---|---|
| Mel526 | 7110 | 80076 | 84401 |
| Mel624 | 7973 | 83644 | 85340 |
| Mel888 | 0 | 6209 | 2485 |
| Mel938 | 0 | 3974 | 1604 |
| PBL | 0 | 4957 | 1419 |

As shown in Table 14, the PBLs co-transduced with DMF4 TCR and SEQ ID NO: 6 or SEQ ID NO: 7 secreted higher levels of IFN-γ than cells that were transduced with TCR and GFP for the co-cultures with Mel526 and Mel624 cells.

The transduced cells are rapidly expanded as described in Example 11. Cells co-transduced with DMF4 TCR and GFP demonstrate approximately 170-fold expansion, cells co-transduced with DMF4 TCR and SEQ ID NO: 6 demonstrate approximately 130-fold expansion, and cells co-transduced with DMF4 TCR and SEQ ID NO: 7 demonstrate approximately 160-fold expansion.

This example demonstrated that co-transduction of host cells with a DMF4 TCR vector and a retroviral vector comprising a nucleotide sequence encoding a nuclear factor of activated T-cells (NFAT) promoter operatively associated with a nucleotide sequence encoding IL-12 results in increased IFN-γ production.

Example 21

Human PBLs are obtained from a donor and are co-transduced with a DMF4 TCR vector (SEQ ID NO: 10) and one of GFP, SEQ ID NO: 11, or SEQ ID NO: 12, according to the method of Example 7. Transduced PBLs are treated by PMA (10 ng/ml) (Sigma Aldrich®, St. Louis, Mo.), Ionomycin (2.2 uM) (Sigma Aldrich®) overnight to stimulate IL-12 secretion.

On day 5, the co-transduced cells are co-cultured with target cells (tumor lines) Mel938 cells (HLA-A2−/gp100+), Mel888 cells (HLA-A2−/gp100+), Mel 624 cells (HLA-A2+/gp100+), or Mel526 cells (HLA-A2+/gp100+)) or PBL (control).

On day 6, PBL cultures are tested for reactivity in cytokine release assays using a commercially available ELISA kit (IFN-γ Endogen, Rockford, Ill.). For these assays, $1 \times 10^5$ responder cells (transduced PBLs) and $1 \times 10^5$ target cell (tumor lines) are incubated in a 0.2 ml culture volume in individual wells of 96-well plates overnight.

Cytokine secretion is measured in culture supernatants diluted as to be in the linear range of the assay. The results are set forth in Table 15.

TABLE 15

| | DMF4 (SEQ ID NO: 10) and GFP (IFN-γ pg/ml) | DMF4 (SEQ ID NO: 10) and SEQ ID NO: 11 (IFN-γ pg/ml) | DMF4 (SEQ ID NO: 10) and SEQ ID NO: 12 (IFN-γ pg/ml) |
|---|---|---|---|
| Mel526 | 7110 | 65468 | 68519 |
| Mel624 | 7973 | 71206 | 68853 |
| Mel888 | 0 | 4828 | 3473 |
| Mel938 | 0 | 3071 | 2600 |
| PBL | 0 | 4519 | 2725 |

As shown in Table 15, the PBLs co-transduced with DMF4 TCR and SEQ ID NO: 11 or SEQ ID NO: 12 secreted higher levels of IFN-γ than cells that were transduced with TCR and GFP for the co-cultures with Mel526 and Mel624 cells.

The transduced cells are rapidly expanded as described in Example 11. Cells co-transduced with DMF4 TCR and GFP demonstrate approximately 170-fold expansion, cells co-transduced with DMF4 TCR and SEQ ID NO: 11 demonstrate approximately 150-fold expansion, and cells co-transduced with DMF4 TCR and SEQ ID NO: 12 demonstrate approximately 170-fold expansion.

This example demonstrated that co-transduction of host cells with a DMF4 TCR vector and a retroviral vector comprising a nucleotide sequence encoding a nuclear factor of activated T-cells (NFAT) promoter operatively associated with a nucleotide sequence encoding IL-12 results in increased IFN-γ production.

Example 22

A series of human single chain IL-12 (hscIL12) genes are designed for expression of IL-12 fusion proteins, where the gene encoding IL-12 p40 is followed by the p35 subunit in which the p35 leader sequence is deleted. The two subunits are joined with different linkers and inserted into the MSGV-1 γ-retroviral vector. Two hscIL12 vectors are assembled using the G6S linker where one hscIL12 gene is the native gene sequence, hscIL12 (G6S)-wt (SEQ ID NO: 2), and the other is a codon-optimized gene, hscIL12 (G6S)-co (SEQ ID NO: 1). Another two vectors are produced using codon-optimized genes; one that utilizes a $(G4S)_3$ linker, hscIL12 $(G4S)_3$ or a vector where the subunits are linked using a picornavirus ribosomal skip element, hscIL12 (P2A).

To compare the ability of these vectors to produce bioactive IL-12, human PBLs are co-transduced with a vector expressing a TCR recognizing melanoma antigen MART-1, (Hughes et al. *Hum Gene Ther.* 16:457-472 (2005)) and the IL-12 retroviral vectors: hscIL12 (G6S)-wt, hscIL12 (G6S)-co, hscIL12 $(G_4S)3$, and hscIL12 (P2A). The vector encoding tLNGFR (truncated low affinity nerve growth factor receptor) is used as an experimental control. The expression of IL-12 is measured by flow cytometry analysis (FACS) using FITC-anti-human IL-12 antibody. The results are shown in Table 16.

TABLE 16A

| Construct | Cells expressing IL-12 (%) |
|---|---|
| IgG | 0 |
| tLNGFR | 0 |
| hscIL12 (wt) (SEQ ID NO: 2) & MART-1 TCR | 13 |
| hscIL12 (G6S) (SEQ ID NO: 1) & MART-1 TCR | 24 |
| hscIL12(G4S)3 & MART-1 TCR | 10 |
| hscIL12(FurinP2A) & MART-1 TCR | 20 |

As shown in Table 16, codon-optimized human single chain IL-12 linked by G6S (SEQ ID NO: 1) yields the highest amount of IL-12 as measured by FACS (24%). These results are confirmed by ELISA assay.

The biologic impact of IL-12 is determined by increased IFN-γ production (measured by ELISA) when engineered PBLs are co-cultured with MART-1 expressing melanoma lines (Mel526, Mel624, Mel888, Mel938). The results are shown in Table 16B (IFN-γ in pg/ml).

TABLE 16B

| | Mel526 | Mel624 | Mel888 | Mel938 | PBL |
|---|---|---|---|---|---|
| tLNGFR | <5000 | <5000 | 0 | 0 | 0 |
| hscIL12 (wt) (SEQ ID NO: 2) & MART-1 TCR | 17000 | 16000 | <5000 | <5000 | <5000 |
| hscIL12 (G6S) (SEQ ID NO: 1) & MART-1 TCR | 18000 | 17000 | <5000 | <5000 | <5000 |
| hscIL12(G4S)3 & MART-1 TCR | 15000 | 17000 | <5000 | <5000 | <5000 |
| hscIL12(FurinP2A) & MART-1 TCR | 14000 | 17000 | <5000 | <5000 | <5000 |

This example demonstrated that codon-optimized human single chain IL-12 linked by G6S (SEQ ID NO: 1) yields the highest amount of IL-12 as compared to hscIL12 (G6S)-wt (SEQ ID NO: 2), hscIL12(G4S)$_3$ or hscIL12 (P2A).

Example 23

Human PBLs are obtained from a donor and are transduced with vector(s): 1) tLNGFR, 2) gp100 TCR and tLNGFR, 3) SEQ ID NO: 5, or 4) SEQ ID NO: 5 and gp100 TCR, according to the method of Example 7. Transduced PBLs are treated by PMA (10 ng/me (Sigma Aldrich®, St. Louis, Mo.), Ionomycin (2.2 uM) (Sigma Aldrich®) overnight to stimulate IL-12 secretion.

On day 5, the co-transduced cells are co-cultured with target cells (tumor lines) Mel938 cells (HLA-A2–/gp100+), or Mel 624 cells (HLA-A2+/gp100+). Cytokines and chemokines produced in the co-culture media are measured by Searchlight analysis. The results are set forth in Table 17 (values in pg/ml).

tured with the target cells. IL-12 production does not affect the production of other cytokines, including IL-4, IL-10, or IL-7. PBLs transduced with SEQ ID NO: 5 produce more IL12p40 and IL-23 when co-cultured with the target cells.

This example demonstrated that co-transduction of host cells with a gp100 TCR vector and a lentiviral vector comprising a nucleotide sequence encoding a NFAT promoter operatively associated with a nucleotide sequence encoding IL-12 results in increased GM-CSF, G-CSF, hMIP1b, IL12p40 and IL-23 production as compared to cells transduced with TCR and tLNGFR.

Example 24

Donor PBL are stimulated with OKT3 on Day 0 and transduced with gp100(154) TCR on Day 2. On Day 3, the cells are transduced with vector(s): 1) MSGV1-GFP, 2) hscIL-12 without NFAT, 3) SEQ ID NO: 14, or 4) SEQ ID NO: 7, as described in Example 5. On day 7, the cells are co-cultured

TABLE 17

| | | hIFNg | hTNFa | hGMCSF | hGCSF | hIL2 | hIL4 | hIL10 | hIL12p70 | hIL7 | hIL12p40 | hIL17 |
|---|---|---|---|---|---|---|---|---|---|---|---|---|
| Mel 624 | tLNGFR | 5.3 | 2.1 | 48.6 | 2.5 | 9.7 | 0.4 | 0.2 | 1.0 | 0.3 | <1.2 | 5.7 |
| | gp100 TCR & tLNGFR | 12983.4 | 986.9 | 31400.1 | 664.7 | 946.5 | 16.2 | 31.5 | 2.5 | 1.3 | 0.9 | 2782.9 |
| | SEQ NO: 5 | 320.5 | 12.8 | 402.7 | 2.9 | 42.2 | 2.7 | 1.8 | 13837.0 | 0.9 | 202.9 | 19.8 |
| | gp100 TCR & SEQ NO 5 | 64198.3 | 2719.0 | 62271.8 | 1446.0 | 799.9 | 40.2 | 42.9 | 15698.5 | 1.4 | 181.6 | 4110.8 |
| Mel 938 | tLNGFR | 4.0 | 2.9 | 57.2 | 1.8 | 15.2 | 0.9 | 0.8 | 0.6 | 2.3 | <1.2 | 4.9 |
| | gp100 TCR & tLNGFR | 2.8 | 0.8 | 36.1 | 1.3 | 17.7 | 0.9 | 0.8 | 0.2 | 1.0 | <1.2 | 3.2 |
| | SEQ NO: 5 | 619.2 | 18.4 | 474.7 | 1.1 | 39.3 | 3.1 | 3.3 | 19983.3 | 3.9 | 269.7 | 25.5 |
| | gp100 TCR & SEQ NO: 5 | 819.9 | 19.0 | 563.9 | 2.0 | 50.7 | 3.4 | 4.2 | 16477.6 | 3.1 | 232.5 | 36.4 |

| | | hIL23 | hRANTES | hI309 | hIP10 | hMCP4 | hMIG | hMIP1b | hGROg | hHCC4 |
|---|---|---|---|---|---|---|---|---|---|---|
| Mel 624 | tLNGFR | 3.7 | 434.2 | 14.5 | 12.1 | 0.3 | 36.8 | 418.7 | 1423.3 | 1.3 |
| | gp100 TCR & tLNGFR | 18.6 | 1860.8 | 1808.9 | 65199.6 | 3.7 | 63664.5 | 31372.3 | 26661.3 | 13.6 |
| | SEQ NO: 5 | 559.2 | 269.3 | 18.1 | 608.2 | 0.3 | 984.1 | 1013.2 | 1491.0 | 9.8 |
| | gp100 TCR & SEQ NO 5 | 569.7 | 1088.8 | 1174.0 | 61715.5 | 3.3 | 66648.9 | 60347.5 | 28055.5 | 16.0 |
| Mel 938 | tLNGFR | 23.6 | 506.6 | 5.9 | 7.1 | 1.1 | 28.9 | 175.6 | 144.1 | 2.7 |
| | gp100 TCR & tLNGFR | <39.1 | 495.1 | 10.2 | 2.9 | <0.8 | 25.6 | 189.6 | 127.6 | <9.8 |
| | SEQ NO: 5 | 524.5 | 390.2 | 19.6 | 805.7 | 0.5 | 1187.7 | 1516.7 | 314.2 | 5.4 |
| | gp100 TCR & SEQ NO: 5 | 506.9 | 573.1 | 22.3 | 1253.0 | 0.6 | 2000.6 | 1539.3 | 350.7 | <9.8 |

Compared with PBLs transduced with gp100 TCR and tLNGFR, cells transduced with gp100 TCR and SEQ ID NO: 5 release more granulocyte-macrophage colony stimulating factor (GM-CSF) (2-fold increase), granulocyte colony-stimulating factor (G-CSF) (2-fold increase), and human macrophage inflammatory protein (hMIP1b) when co-culand stimulated to secrete IL-12 as described in Example 8. PBL cultures are tested for reactivity in a cytokine release assay as described in Example 8 using a commercially available ELISA kit (IFN-γ or IL-12; Endogen, Rockford, Ill.). The results are set forth in Table 18 (IFN-γ, pg/ml) and Table 19 (IL-12, pg/ml).

TABLE 18

| | Mel526 | | Mel624 | | Mel888 | | Mel938 | | PBL alone | |
|---|---|---|---|---|---|---|---|---|---|---|
| | Donor 1 | Donor 2 | Donor 1 | Donor 2 | Donor 1 | Donor 2 | Donor 1 | Donor 2 | Donor 1 | Donor 2 |
| gp 100(154) TCR only | 9479 | 6039 | 4682 | 3908 | 0 | 0 | 531 | 119 | 65 | 0 |
| gp100(154) TCR and MSGV1-GFP | 6896 | 5223 | 3670 | 3319 | 90 | 0 | 0 | 0 | 0 | 0 |
| gp100(154) TCR and hscIL-12 without NFAT | 24720 | 36716 | 28640 | 31377 | 199 | 52 | 49 | 0 | 271 | 1105 |
| gp100(154) TCR and SEQ ID NO: 14 | 38492 | 26878 | 26858 | 24559 | 110 | 0 | 90 | 0 | 80 | 30 |

TABLE 18-continued

| | Mel526 | | Mel624 | | Mel888 | | Mel938 | | PBL alone | |
|---|---|---|---|---|---|---|---|---|---|---|
| | Donor 1 | Donor 2 | Donor 1 | Donor 2 | Donor 1 | Donor 2 | Donor 1 | Donor 2 | Donor 1 | Donor 2 |
| gp100(154) TCR and SEQ ID NO: 7 | 29597 | 27988 | 25264 | 23256 | 143 | 0 | 0 | 0 | 0 | 0 |

As shown in Table 18, cells co-transduced with a TCR and SEQ ID NO: 14 secrete IFN-γ when the cells are co-cultured with Mel624 or Mel526.

TABLE 19

| | Mel526 | | Mel624 | | Mel888 | | Mel938 | | PBL alone | |
|---|---|---|---|---|---|---|---|---|---|---|
| | Donor 1 | Donor 2 | Donor 1 | Donor 2 | Donor 1 | Donor 2 | Donor 1 | Donor 2 | Donor 1 | Donor 2 |
| gp100(154) TCR and hscIL-12 without NFAT | >3000 | >3000 | >3000 | >3000 | >3000 | >3000 | >3000 | >3000 | >3000 | >3000 |
| gp100(154) TCR and SEQ ID NO: 14 | >3000 | 2330 | >3000 | 1581 | 6 | 0 | 0 | 0 | 0 | 0 |
| gp100(154) TCR and SEQ ID NO: 7 | 1227 | 638 | 770 | 375 | 0 | 0 | 2 | 0 | 0 | 0 |

As shown in Table 19, cells co-transduced with a TCR and SEQ ID NO: 14 secrete IL-12 when the cells are co-cultured with Mel624 or Mel526.

This example demonstrated that the NFAT responsive promoter of SEQ ID NO: 14 directs IL-12 expression through TCR recognition of specific tumor antigen.

Example 25

Donor PBLs ($2 \times 10^6$/well) are transduced as described in Example 5 with a vector encoding a gp100(154) TCR alone or with one of the vectors described in Example 24. On day 11, the cells are rapidly expanded, as described in Example 11. The results are shown in Table 20.

TABLE 20

| | Fold Expansion (approximate) | |
|---|---|---|
| Vector(s) | Donor 1 | Donor 2 |
| gp100(154) TCR only | 325 | 525 |
| gp100(154) TCR and MSGV1-GFP | 350 | 500 |
| gp100(154) TCR and hscIL-12 without NFAT | 175 | 50 |
| gp100(154) TCR and SEQ ID NO: 14 | 330 | 75 |
| gp100(154) TCR and SEQ ID NO: 7 | 410 | 75 |

This example demonstrated that the proliferation of cells transduced with a TCR and either SEQ ID NO: 7 or SEQ ID NO: 14 varies among different donors.

Example 26

To select a clone suitable for clinical virus production, PG13 packaging cells are transduced with retrovirus comprising a vector comprising SEQ ID NO: 14. Six stable clones (IL12-C4, IL12-D3, IL12-F2, IL12-F4, IL12-F8, and IL12-G11) are selected and tested for efficient transduction of PBLs. Transduced PBLs are co-cultured with tumor target cells and tested for IFN-γ and IL-12 production by ELISA as described in Example 8. All six clones can efficiently transduce PBLs. IL-12 production is induced and IFN-γ production is enhanced upon co-culture of transduced PBLs with tumor target cells. IL12-D3 and IL12-F4 are selected for further testing because they express lower amounts of background IL-12 and the transduced cells are able to proliferate. A modest reduction in cell proliferation is observed in TILs transduced with SEQ ID NO: 14. Clones IL12-D3 and IL12-F4 can both efficiently transduce CD8+ TILs, with the production of IL-12 being slightly higher in the cells transduced with IL12-D3.

This example demonstrated the selection of a packaging cell clone suitable for clinical virus production.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a nuclear factor of activated T-cells (NFAT) promoter operatively associated with a nucleotide sequence encoding IL-12.

2. A nucleic acid comprising a nucleotide sequence encoding a nuclear factor of activated T-cells (NFAT) promoter operatively associated with a nucleotide sequence encoding IL-12, wherein the NFAT promoter is located 3' of the nucleotide sequence encoding IL-12.

3. The nucleic acid of claim 1, wherein the IL-12 is human IL-12.

4. The nucleic acid of claim 1, wherein the IL-12 is single chain IL-12.

5. The nucleic acid of claim 1, wherein the IL-12 comprises a sequence selected from the group consisting of SEQ NOs: 1-3.

6. The nucleic acid of claim 1, wherein the NFAT promoter comprises SEQ ID NO: 4.

7. A nucleic acid comprising a nucleotide sequence that is complementary to the nucleic acid of claim 1.

8. A nucleic acid comprising a nucleotide sequence that hybridizes to the nucleic acid of claim 1 at a temperature of 50-70° C. and an NaCl concentration of 0.02-0.1 M.

9. A recombinant expression vector comprising the nucleic acid of claim 1.

10. A recombinant expression vector comprising the nucleic acid of claim 1, wherein the recombinant expression vector comprises a sequence selected from the group consisting of SEQ NOs: 5-8, 11-12, and 14.

11. A recombinant expression vector comprising the nucleic acid of claim 2, wherein the recombinant expression vector comprises a sequence selected from the group consisting of SEQ ID NOs: 7 and 14.

12. The recombinant expression vector of claim 9, wherein the vector is selected from the group consisting of a retroviral vector, a lentiviral vector, a herpes viral vector, an adeno-associated viral vector, a transposon vector and an adenoviral vector.

13. A host cell comprising the recombinant expression vector of claim 9.

14. The host cell of claim 13, further comprising a recombinant expression vector comprising a nucleotide sequence encoding a T cell receptor (TCR).

15. The host cell of claim 14, wherein the TCR has antigenic specificity for an infectious disease antigen.

16. The host cell of claim 15, wherein the infectious disease antigen is selected from the group consisting of an HIV antigen, an influenza antigen, a Herpes virus antigen, a hepatitis antigen, and a malaria antigen.

17. The host cell of claim 14, wherein the TCR has antigenic specificity for a cancer antigen.

18. The host cell of claim 17, wherein the cancer antigen is a melanoma antigen.

19. The host cell of claim 17, wherein the cancer antigen is selected from the group consisting of p53, RB, Her2/neu, CEA, PSMA, NY-ESO-1, MAGE, gp100, TRP-1, MART-1, tyrosinase tumor antigen, PSCA, HMW-MAA, CD19, VEGFR2, SSX, and EGFRvIII.

20. The host cell of claim 19, wherein the nucleotide sequence encoding the TCR is selected from the group consisting of SEQ ID NO: 9, SEQ ID NO: 10, and SEQ ID NO: 13.

21. A population of cells comprising at least one host cell of claim 13.

22. A pharmaceutical composition comprising the nucleic acid of claim 1 and a pharmaceutically acceptable carrier.

23. A method of treating a mammal with a cancer or an infectious disease, wherein the mammal expresses a cancer antigen or an infectious disease antigen, the method comprising:
  (a) isolating autologous T cells from the mammal, wherein the T cell expresses a T cell receptor (TCR) specific for the cancer antigen or the infectious disease antigen;
  (b) transducing the T cells with the recombinant expression vector of claim 9; and
  (c) administering the T cells of (b) to the mammal, wherein upon administering the T cells to the mammal, the cancer antigen or the infectious disease antigen stimulates expression of the nucleotide sequence encoding IL-12 and treats the mammal with the cancer or infectious disease.

24. A method of inducing IL-12 expression in a mammal expressing an antigen, the method comprising:
  a) isolating autologous T cells from a mammal;
  b) transducing the isolated T cells with the recombinant expression vector of claim 9;
  c) transducing the isolated T cells with a second recombinant expression vector comprising a nucleotide sequence encoding a TCR specific for the antigen, wherein the nucleotide sequence encoding the TCR is operably linked to a promoter;
  d) administering the transduced cells to the mammal; and
  e) stimulating the TCR by the antigen, wherein the transduced T cell expresses the TCR specific for the antigen and the stimulating induces IL-12 expression.

25. A method of treating a mammal with a cancer or an infectious disease, the method comprising:
  a) isolating autologous T cells from the mammal, wherein the T cell expresses a T cell receptor (TCR) specific for an antigen;
  b) transducing the T cells with the recombinant expression vector of claim 9;
  c) administering the T cells of b) to the mammal; and
  d) administering the antigen to the mammal, wherein upon administering the antigen to the mammal, the antigen stimulates expression of the nucleotide sequence encoding IL-12 and treats the mammal with the cancer or the infectious disease.

26. A method of inducing IL-12 expression in a mammal, the method comprising:
  a) isolating autologous T cells from a mammal;
  b) transducing the isolated T cells with the recombinant expression vector of claim 9;
  c) transducing the isolated T cells with a second recombinant expression vector comprising a nucleotide sequence encoding a TCR specific for an antigen, wherein the nucleotide sequence encoding the TCR is operably linked to a promoter;
  d) administering the transduced T cells to the mammal; and
  e) stimulating the TCR by administering the antigen, wherein the transduced T cell expresses the TCR specific for the antigen and the stimulating induces IL-12 expression.

* * * * *